(12) United States Patent
Merali et al.

(10) Patent No.: US 11,596,615 B2
(45) Date of Patent: *Mar. 7, 2023

(54) COMPOSITIONS AND METHODS FOR TREATMENT OF INSULIN RESISTANCE

(71) Applicant: Temple University—Of The Commonwealth System Of Higher Education, Philadelphia, PA (US)

(72) Inventors: Salim Merali, Philadelphia, PA (US); Carlos A. Barrero, Philadelphia, PA (US); Wayne E. Childers, New Hope, PA (US); George C. Morton, Collegeville, PA (US)

(73) Assignee: TEMPLE UNIVERSITY—OF THE COMMONWEALTH SYSTEM OF HIGHER EDUCATION, Philadelphia, PA (US)

(*) Notice: Subject to any disclaimer, the term of this patent is extended or adjusted under 35 U.S.C. 154(b) by 12 days.

This patent is subject to a terminal disclaimer.

(21) Appl. No.: 16/932,236

(22) Filed: Jul. 17, 2020

(65) Prior Publication Data

US 2021/0046030 A1 Feb. 18, 2021

Related U.S. Application Data

(63) Continuation of application No. 16/331,489, filed as application No. PCT/US2017/050462 on Sep. 7, 2017, now Pat. No. 10,729,670.

(60) Provisional application No. 62/384,390, filed on Sep. 7, 2016.

(51) Int. Cl.
*A61K 31/198* (2006.01)
*A61P 3/08* (2006.01)

(52) U.S. Cl.
CPC ............ *A61K 31/198* (2013.01); *A61P 3/08* (2018.01)

(58) Field of Classification Search
CPC .................................................. A61K 31/198
See application file for complete search history.

(56) References Cited

U.S. PATENT DOCUMENTS

| | | | |
|---|---|---|---|
| 5,059,595 A | 10/1991 | Le Grazie | |
| 5,073,543 A | 12/1991 | Marshall et al. | |
| 5,120,548 A | 6/1992 | McClelland et al. | |
| 5,344,846 A | 9/1994 | Jakus et al. | |
| 5,591,767 A | 1/1997 | Mohr et al. | |
| 5,639,476 A | 6/1997 | Oshiack et al. | |
| 5,674,533 A | 10/1997 | Santus et al. | |
| 5,733,566 A | 3/1998 | Lewis | |
| 6,958,325 B2 | 10/2005 | Domb | |
| 7,799,782 B2 | 9/2010 | Munson et al. | |
| 10,729,670 B2 * | 8/2020 | Merali | ...................... A61P 3/08 |
| 2009/0253641 A1 | 10/2009 | Neufer et al. | |
| 2013/0030007 A1 | 1/2013 | Penninger et al. | |
| 2014/0286909 A1 | 9/2014 | Garcia-Rodenas | |
| 2014/0294774 A1 | 10/2014 | Nieuwdorp et al. | |
| 2015/0182483 A1 | 7/2015 | Goldberg | |
| 2016/0038542 A1 | 2/2016 | Riordan et al. | |
| 2016/0113951 A1 | 4/2016 | Dhurandhar et al. | |

FOREIGN PATENT DOCUMENTS

| | | |
|---|---|---|
| CN | 103833623 A | 3/2014 |
| CN | 103833623 B | 7/2016 |
| WO | WO-1997/032862 | 9/1997 |
| WO | WO 2009/100363 A2 | 8/2009 |
| WO | WO-2009/100363 A2 | 8/2009 |
| WO | WO-2015/161448 A1 | 10/2015 |
| WO | WO-2015/187942 A1 | 12/2015 |
| WO | WO 2017/044933 A1 | 3/2017 |
| WO | WO 2017/208232 A1 | 12/2017 |
| WO | WO-2019/173633 A1 | 9/2019 |
| WO | WO-2019/173640 A1 | 9/2019 |
| WO | WO 2020/061232 A1 | 3/2020 |

OTHER PUBLICATIONS

National Center for Biotechnology Information. "PubChem Compound Summary for CID 194196" PubChem, https://pubchem.ncbi.nlm.nih.gov/compound/2S_-2-amino-5-_3-aminopropylamino_pentanoic-acid. Published Aug. 9, 2005. Accessed Feb. 23, 2021.

Ascaso et al., "Diagnosing insulin resistance by simple quantitative methods in subjects with normal glucose metabolism," *Diabetes Care*, 26: 3320-3325, (2003).

Bey et al., "Analogs of ornithine as inhibitors of ornithine decarboxylase. New deductions concerning the topography of the enzyme's active site", Journal of Medicinal Chemistry, pp. 50-55, (1978).

Beyaz et al., "High-Fat Diet Enhances Sternness and Tumorigenicity of Intestinal Progenitors," Nature 531:55-58 plus Supplementary Information, (2016).

Boden et al., "Excessive caloric intake acutely causes oxidative stress, GLUT4 carbonylation, and insulin resistance in healthy men," Science Translational Medicine, 7(304): 304re7, (2015).

Boden et al., 7(304): 304re7, Supplementary Materials, (2015).

Datta et al., "Glutamate metabolism in HIV-1 infected macrophages: Role of HIV-1 Vpr. Cell Cycle," *Cell Cycle*. 15(17):2288-98, (Epub May 31, 2016).

Demozay et al., "FALDH reverses the deleterious action of oxidative stress induced by lipid peroxidation product 4-hydroxynonenal on insulin signaling in 3T3-L1 adipocytes," Diabetes 57(5):1216-26, (Epub Jan. 3, 2008.).

Dietmair et al., "Towards quantitative metabolomics of mammalian cells: development of a metabolite extraction protocol," *Anal Biochem.*, 404:155-64; Abstract only, (2010).

ISR and Written Opinion dated Dec. 21, 2017 in PCT/US17/50462, filed Sep. 7, 2017.

(Continued)

Primary Examiner — Rei Tsang Shiao
(74) Attorney, Agent, or Firm — Proskauer Rose LLP

(57) ABSTRACT

Compounds of Formula (I), and pharmaceutically effective salts thereof; wherein $R^1$-$R^{14}$, m, n, o, p, q and r are as defined herein, are provided for treatment of for increasing insulin sensitivity, reducing insulin resistance, preventing insulin resistance and treating insulin resistance disorders.

29 Claims, 18 Drawing Sheets
Specification includes a Sequence Listing.

(56) References Cited

OTHER PUBLICATIONS

ISR and Written Opinion dated Jun. 3, 2019 in PCT/US2019/021220, filed Mar. 7, 2019.
ISR and Written Opinion dated Jun. 10, 2019 in PCT/US2019/021230, filed Mar. 7, 2019.
Kastle et al., "Protein oxidative modification in the aging organism and the role of the ubiquitin proteasomal system." *Curr. Pharm. Des.* 17(36): 4007-4022. Abstract only, (2011).
Maier et al., "Hypusine: a New Target for Therapeutic Intervention in Diabetic Inflammation," Discovery Medicine 10(50): 18-23, (2010).
Nathan, "International Expert Committee Report on the Role of the A1C Assay in the Diagnosis of Diabetes The International Expert Committee" *Diabetes Care* 32 (7) 1327-1334, (2009).
Nathan, "International Expert Committee Report on the Role of the A1C Assay in the Diagnosis of Diabetes David M. Nathan, on behalf of the International Expert Committee" Diabetes Care 32 (12) e160, (2009).
Paoletti, et al., "Metabolic syndrome, inflammation and atherosclerosis," *Vasc Health Risk Manag* 2(2):145-152, (2006).
PubChem-CID-65396, Create Date: Aug. 8, 2005 (Aug. 8, 2005).
PubChem-CID-122083, Downloaded Oct. 22, 2017 from the Internet https://pubchem.ncbi.nlm.nih.gov/compound/5122083#section=Top, Create Date: Sep. 18, 2005 (Sep. 18, 2005).
PubChem-CID-21878230, Create Date: Dec. 5, 2007 (Dec. 5, 2007).
PubChem-CID-18674791, Create Date: Dec. 4, 2007 (Dec. 4, 2007).
PubChem-CID-42552857, Create Date: May 30, 2009 (May 30, 2009).
PubChem-CID-54059533, Downloaded Oct. 26, 2017 from the Internet https://pubchem.ncbi.nlm.nih.gov/compound/54059533#section=Top, Create Date: Dec. 2, 2011 (Dec. 4, 2011).
Reaven, "Role of insulin resistance in human disease," *Diabetes*, 37(12): 1595-1607 (reprinted 1997 Nutrition 13: 64-66), (1988).
Robbins et al., "Inhibition of Deoxyhypusine Synthase Enhances Islet ? Cell Function and Survival in the Setting of Endoplasmic Reticulum Stress and Type 2 Diabetes," JBC 285(51):39943-39952, (2010).
Schaur et al., "4-Hydroxy-nonenal—A Bioactive Lipid Peroxidation Product," Biomolecues 5:2247-2337, (2015).
Schaur, "Basic Aspects of the Biochemical Reactivity of 4-hydroxynonenal," Mol Aspects Med. 24(4-5):149-159. Abstract only, (2003).
Supplementary European Search Report for EP17849523 (dated Mar. 20, 2020).
Tersey et al., "Protective effects of polyamine depletion in mouse models of type 1 diabetes: implications for therapy", Amino Acids, vol. 46, No. 3, pp. 633-643, (2013).
Xu et al., "Chapter 14—Detecting protein carbonylation in adipose tissue and in cultured adipocytes." Methods in Enzymology 538, 249-261. Abstract only, (2014).
Zhai et al., "Structural Analysis and Optimization of Context-Independent Anti-Hypusine Antibodies," J Mol Bio. 428:603-617, (2016).
Extended European Search Report for EP19763756.4, dated Nov. 23, 2021 (7 pages).
Extended European Search Report for EP19763857.0, dated Nov. 30, 2021 (8 pages).

\* cited by examiner

COMPOSITIONS AND METHODS FOR TREATMENT OF INSULIN RESISTANCE

CROSS-REFERENCE TO RELATED APPLICATIONS

This application is a continuation of U.S. patent application Ser. No. 16/331,489, filed Mar. 7, 2019, now U.S. Pat. No. 10,729,670, issued Aug. 4, 2020, which is a National Stage Application under 35 U.S.C. § 371 of International Application No. PCT/US2017/050462, filed Sep. 7, 2017, and claims the benefit of U.S. Provisional Application No. 62/384,390, filed Sep. 7, 2016, the entire disclosure of which is incorporated herein by reference.

REFERENCE TO GOVERNMENT GRANT

The invention was made with government support under grant no. RO1-DK90588 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 6, 2017 is named 35926_0495_WO_565205_SL.txt and is 1,200 bytes in size.

FIELD OF THE INVENTION

The invention relates to the field of metabolic diseases. Particularly, the invention relates to treatment of insulin resistance.

BACKGROUND OF THE INVENTION

In Type 1 diabetes, also known as insulin-dependent diabetes mellitus (IDDM), or juvenile diabetes, the pancreas produces little or no insulin. Type 1 diabetes is believed to result in part from the autoimmune attack on the insulin producing beta-cells of the pancreas.

Type 2 diabetes mellitus (T2DM), also known as Non-Insulin Dependent Diabetes Mellitus (NIDDM), or adult-onset diabetes, is mostly caused by insulin resistance and eventually results in beta-cell exhaustion, leading to beta-cell destruction. Insulin resistance is associated with impairment of peripheral tissue response to insulin. T2DM is primarily due to obesity and not insufficient exercise in people who are genetically predisposed. It makes up about 90% of cases of diabetes. Rates of T2DM have increased markedly since 1960 in parallel with obesity. It is believed to afflict approximately 18.2 million people in the US. T2DM typically begins in middle or older age. However, as a result of the obesity epidemic, substantially younger patients are diagnosed with this condition. Type 2 diabetes is associated with a ten-year-shorter life expectancy.

Insulin resistance is generally regarded as a pathological condition in which cells fail to respond to the normal actions of the hormone insulin. When the body produces insulin under conditions of insulin resistance, the cells in the body are resistant to the insulin and are unable to use it as effectively, leading to high blood sugar.

In the early stage of T2DM, the predominant abnormality is reduced insulin sensitivity. At this stage hyperglycemia can be reversed by a variety of measures and medications known in the art. In reaction to increasing insulin resistance, beta-cells are forced to produce more insulin, or are triggered to proliferate and/or granulate, producing even more insulin. The overproduction of insulin or over activity of beta-cells can then lead to beta-cell exhaustion, leading to destruction of the beta-cell population. The pancreas can thus no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure, and blindness.

Insulin resistance is present in almost all obese individuals (Paoletti et al., *Vasc Health Risk Manag* 2:145-152). Obesity-linked insulin resistance greatly increases the risk for T2DM, hypertension, dyslipidemia, and nonalcoholic fatty liver disease, together known as the metabolic or insulin resistance syndrome (Reaven, *Diabetes,* 37: 1595-1607 (1988)).

Insulin resistance and T2DM are associated to increased risk of heart attacks, strokes, amputation, diabetic retinopathy, and kidney failure. For extreme cases, circulation of limbs is affected, potentially requiring amputation. Loss of hearing, eyesight, and cognitive ability has also been linked to these conditions.

Management of insulin resistance in children and adults is essentially based on dietary and lifestyle changes, including healthier dietary habits and increased exercise. These practices can be very efficient in improving insulin sensitivity and in slowing the progression of the disease, but they are difficult to apply and actually not followed by most patients. T2DM can be treated with drugs promoting insulin sensitivity, e.g., thiazolidinedionesthes, but their efficacy in reducing the rate of progression of the disease is quite low. Insulin treatment is required during the most advanced phases of the disease.

Thiazolidinediones, such as troglitazone, rosiglitazone and pioglitazone, bind to peroxisome proliferator-activated receptors, a group of receptor molecules inside the cell nucleus. The normal ligands for these receptors are free fatty acids (FFAs) and eicosanoids. When activated, the receptor migrates to the DNA, activating transcription of a number of specific genes. The activation of these different genes results in 1) decreasing insulin resistance, 2) modifying adipocyte differentiation, 3) inhibiting VEGF-induced angiogenesis, 4) decreasing leptin levels (leading to an increased appetite), 5) decreasing certain interleukins (e.g., IL-6) levels, and 6) increasing adiponectin levels. However, thiazolidinedione intake is usually associated with a weight gain. Efficacy in reducing the rate of disease progression is low. Thus, there is a still a need for more effective therapies for insulin resistance.

How obesity promotes insulin resistance remains incompletely understood, although several potential mechanisms have been proposed. Plasma concentrations of free fatty acids and pro-inflammatory cytokines, endoplasmic reticulum (ER) stress, and oxidative stress are all elevated in obesity and have been shown to induce insulin resistance. However, they may be late events that only develop after chronic excessive nutrient intake.

In overnutrition, excessive glucose is consumed and a large amount of glucose is metabolized via glycolysis and the TCA cycle leading to increased NADH and FADH2 production in the mitochondrial electron transport chain and increased reactive oxygen species (ROS). When the generation of ROS exceeds their detoxification, oxidative stress occurs. Oxidative stress may cause reversible or irreversible changes in proteins. Reversible changes occur in cysteine residues and can be repaired by antioxidant proteins. On the other hand, oxidative stress can directly or indirectly induce irreversible damage to the proteins by formation of reactive carbonyl groups, mainly aldehydes and ketones. Direct protein carbonylation of lysine or arginine residues occurs through a Fenton reaction of metal cations with hydrogen peroxide, forming glutamic semialdehyde. Indirect carbonylation can occur by reactive α,β-unsaturated aldehydes, which are products of oxidative modification of polyunsaturated fatty acids (PUFA).

The most common reactive aldehyde is 4-hydroxynonenal (4-HNE). 4-HNE reacts with cysteine, lysine, and histidine residues of proteins via Michael addition and Schiff base formation. The introduction of carbonyl derivatives (i.e. aldehydes and ketones) alters the conformation of the polypeptide chain, resulting in the partial or total inactivation of proteins. Because protein carbonylation is an irreversible process, it is deleterious to the cells. 4-HNE increases have been reported in T2DM and in the liver of diabetic rats.

In a study reported in 2015, healthy men were fed with ~6000 kcal/day of the common U.S. diet [~50% carbohydrate (CHO), ~35% fat, and ~15% protein] for 1 week. The diet produced a rapid weight gain of 3.5 kg and the rapid onset (after 2 to 3 days) of systemic and adipose tissue insulin resistance and oxidative stress but no inflammatory or ER stress. Boden et al., *Science Translation Medicine*, 7 (304): 304re7 (9 Sep. 2015). In adipose tissue, the oxidative stress was associated with several GLUT4 posttranslational modifications, including extensive GLUT4 carbonylation as well as adduction of HNE and glutamic semialdehyde in close proximity to the glucose transport channel. Id. GLUT4 is the major insulin-facilitated glucose transporter in adipose tissue. Carbonylation typically causes protein cross-linking and loss or alteration of protein function (Schaur, *Mol. Aspects Med.* 24: 149-159 (2003) and can target the affected proteins for selective degradation by the 26S proteasome (Kastle et al., *Curr. Pharm. Des.* 17: 4007-4022 (2011)).

Notwithstanding these advances, what is still needed are therapeutic agents for the prevention and treatment of insulin resistance, particularly in obese patients who typically suffer from insulin resistance or are most susceptible to the development of insulin resistance, and ultimately, type 2 diabetes.

SUMMARY OF THE INVENTION

In an embodiment, a method for increasing insulin sensitivity, reducing insulin resistance and/or preventing insulin resistance in a subject in need thereof comprises administering to the subject an effective amount of a compound according to Formula I, or pharmaceutically effective salt thereof:

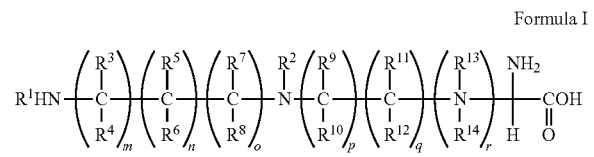

Formula I wherein:

$R^1$ is selected from the group consisting of hydrogen, $-(C_1-C_8)$alkyl, $-(C_1-C_8)$alkenyl, $-(C_1-C_8)$alkynyl, unsubstituted or substituted -ara$(C_1-C_6)$alkyl, unsubstituted or substituted -heteroara$(C_1-C_6)$alkyl, where the substituents on said substituted ara$(C_1-C_6)$alkyl and substituted heteroara$(C_1-C_6)$alkyl are selected from the group consisting of halogen, $-CN$, $-NO_2$, $-NH_2$, $-NH(C_1-C_6)$alkyl, $-N[(C_1-C_6)$alkyl$)]_2$, $-OH$, halo$(C_1-C_6)$alkyl, $-(C_1-C_6)$alkoxy, halo$(C_1-C_6)$alkoxy, $-SH$, thio$(C_1-C_6)$alkyl, $-SONH_2$, $-SO_2NH_2$, $-SO-(C_1-C_6)$alkyl, $-SO_2-(C_1-C_6)$alkyl, $-NHSO_2(C_1-C_6)$alkyl, and $-NHSO_2NH_2$;

$R^2$ is selected from the group consisting of hydrogen, $-(C_1-C_8)$alkyl, $-(C_1-C_8)$alkenyl, $-(C_1-C_8)$alkynyl, unsubstituted or substituted -ara$(C_1-C_6)$alkyl, unsubstituted or substituted -heteroara$(C_1-C_6)$alkyl, where the substituents on said substituted ara$(C_1-C_6)$alkyl and substituted heteroara$(C_1-C_6)$alkyl are selected from the group consisting of halogen, $-CN$, $-NO_2$, $-NH_2$, $-OH$, halo$(C_1-C_6)$alkyl, $-(C_1-C_6)$alkoxy, halo$(C_1-C_6)$alkoxy, $-SH$, thio$(C_1-C_6)$alkyl, $-SONH_2$, $-SO_2NH_2$, $-SO-(C_1-C_6)$alkyl, $-SO_2-(C_1-C_6)$alkyl, $-NHSO_2(C_1-C_6)$alkyl, and $-NHSO_2NH_2$;

$R^3$, $R^4$, $R^7$, $R^8$, $R^9$, $R^{10}$, $R^{13}$, and $R^{14}$ are independently selected from the group consisting of hydrogen and $-(C_1-C_6)$alkyl;

$R^5$ and $R^6$ are independently selected from the group consisting of hydrogen, $-(C_1-C_6)$alkyl and $-OH$, provided that both $R^5$ and $R^6$ cannot be $-OH$;

$R^{11}$ and $R^{12}$ are independently selected from the group consisting of hydrogen, $-(C_1-C_6)$alkyl and $-OH$, provided that both $R^{11}$ and $R^{12}$ cannot be $-OH$;

m is an integer from 1 to 4;
n is an integer from zero to 4
o is an integer from 0 to 4;
p is an integer from 1 to 4;
q is an integer from zero to 4; and
r is an integer from 0 to 4.

Also provided is a method of treating insulin resistance in a subject in need thereof comprising administering to the patient an effective amount of a compound according to Formula I, or pharmaceutically effective salt thereof.

Also provided is a method of treating an insulin resistance disorder in a subject in need thereof comprising administering to the individual an effective amount of a compound according to Formula I, or pharmaceutically effective salt thereof.

Also provided is a method of alleviating an insulin resistance disorder in a subject in need thereof comprising administering to the individual an effective amount of a compound according to Formula I, or pharmaceutically effective salt thereof. Insulin resistance disorders include, by way of example and not limitation, diabetes, obesity, metabolic syndrome, insulin resistance, insulin-resistance syndromes, syndrome X, high blood pressure, hypertension, high blood cholesterol, hyperlipidemia, dyslipidemia, atherosclerotic disease, hyperglycemia, hyperinsulinemia, hyperproinsulinemia, impaired glucose tolerance, delayed insulin release, coronary heart disease, angina pectoris, congestive heart failure, stroke, cognitive dysfunction, retinopathy, peripheral neuropathy, nephropathy, glomerulonephritis, glomerulosclerosis, nephrotic syndrome, hypertensive nephrosclerosis, endometrial cancer, breast cancer, prostate cancer, colon cancer, complications of pregnancy, menstrual irregularities, infertility, irregular ovulation, polycystic ovarian syndrome (PCOS), lipodystrophy, cholesterol related disorders, gout, obstructive sleep apnea, osteoarthritis, and osteoporosis.

In certain embodiments, the subject is afflicted with insulin resistance, reduced insulin sensitivity or an insulin resistance disorder. In other embodiments, the patient is at risk of developing these conditions, and a compound of Formula I is administered prophylactically, to delay the onset of such conditions, or reduce the severity when the conditions are experienced.

Also provided are compounds according to Formula I, and pharmaceutically effective salts thereof, for use in increasing insulin sensitivity, reducing insulin resistance and/or preventing insulin resistance in a subject. Also provided are compounds according to Formula I, and pharmaceutically effective salts thereof, for use in treating insulin resistance in a subject. Also provided are compounds according to Formula I, and pharmaceutically effective salts thereof, for use in treating an insulin resistance disorder in a subject. Also provided are compounds according to Formula I, and pharmaceutically effective salts thereof, for use in alleviating an insulin resistance disorder in a subject.

Also provided is a medicament for increasing insulin sensitivity, reducing insulin resistance and/or preventing insulin resistance in a subject, containing a compound according to Formula I, or pharmaceutically effective salt thereof. Also provided is a medicament for treating insulin resistance in a subject, containing a compound according to Formula I, or pharmaceutically effective salt thereof. Also provided is a medicament for in treating an insulin resistance disorder in a subject, containing a compound according to Formula I, or pharmaceutically effective salt thereof. Also provided is a medicament for alleviating an insulin resistance disorder in a subject.

In certain embodiments of the aforesaid methods and uses of a compound according to Formula I, or pharmaceutically effective salt thereof, $R^1$ and $R^2$ are independently selected from the group consisting of hydrogen and —$(C_1$-$C_8)$alkyl.

In certain embodiments of the aforesaid methods and uses of a compound according to Formula I, or pharmaceutically effective salt thereof, each of $R^3$, $R^4$, $R^5$, $R^6$, $R^7$, and $R^8$ is independently selected from hydrogen and —$(C_1$-$C_8)$alkyl. In certain such embodiments, each of $R^9$, $R^{10}$, $R^{11}$, $R^{12}$, $R^{13}$, and $R^{14}$ is also independently selected from hydrogen and —$(C_1$-$C_8)$alkyl.

In certain embodiments of the aforesaid methods and uses of a compound according to Formula I, or pharmaceutically effective salt thereof, each of $R^9$, $R^{10}$, $R^{11}$, $R^{12}$, $R^{13}$, and $R^{14}$ is independently selected from hydrogen and —$(C_1$-$C_8)$alkyl.

In certain embodiments of the aforesaid methods and uses of a compound according to Formula I, or pharmaceutically effective salt thereof, the sum of m+n+o is in the range of from 2 to 10, and the sum of p+q+r is in the range of from 1 to 10.

In certain embodiments of the aforesaid methods and uses of a compound according to Formula I, or pharmaceutically effective salt thereof, m is 3; p is 4; each of n, o, q and r is zero. In certain such embodiments, $R^3$, $R^4$, $R^9$, and $R^{10}$ are independently selected from hydrogen and —$(C_1$-$C_8)$alkyl. In certain such embodiments, $R^1$ and $R^2$ are independently selected from the group consisting of hydrogen and —$(C_1$-$C_8)$alkyl. In certain such embodiments, $R^1$, $R^2$, $R^3$, $R^4$, $R^9$ and $R^{10}$ are hydrogen.

In certain embodiments, the compound of Formula I is (S)-2-amino-6-((3-aminopropyl)amino)hexanoic acid, or a pharmaceutically effective salt thereof.

In certain embodiments of the aforesaid methods and uses of a compound according to Formula I, or pharmaceutically effective salt thereof, m is 4; n is 2; o is zero; p is 3; q is 1; and r is zero. In certain such embodiments, $R^3$, $R^4$, $R^5$, $R^6$, $R^9$, $R^{10}$, $R^{11}$, and $R^{12}$ are independently selected from hydrogen and —$(C_1$-$C_8)$alkyl. In certain such embodiments, $R^1$ and $R^2$ are independently selected from the group consisting of hydrogen and —$(C_1$-$C_8)$alkyl. In certain such embodiments, $R^1$, $R^2$, $R^3$, $R^4$, $R^5$, $R^6$, $R^9$, $R^{10}$, $R^{11}$, and $R^{12}$, are hydrogen.

In certain embodiments, the compound of Formula I is (S)-2-amino-5-((6-aminohexyl)amino)pentanoic acid, or a pharmaceutically effective salt thereof.

In certain embodiments of the aforesaid methods and uses of a compound according to Formula I, or pharmaceutically effective salt thereof, m is 4; n is 1; o is zero; p is 3; q is 1; and r is zero. In certain such embodiments, $R^3$, $R^4$, $R^5$, $R^6$, $R^9$, $R^{10}$, $R^{11}$ and $R^{12}$ are independently selected from hydrogen and —$(C_1$-$C_8)$alkyl. In certain such embodiments, $R^1$ and $R^2$ are independently selected from the group consisting of hydrogen and —$(C_1$-$C_8)$alkyl. In certain such embodiments, $R^1$, $R^2$, $R^3$, $R^4$, $R^5$, $R^6$, $R^9$, $R^{10}$, $R^{11}$, and $R^{12}$ are hydrogen.

In certain embodiments, the compound of Formula I is (S)-2-amino-5-((5-aminopentyl)amino)pentanoic acid, or a pharmaceutically effective salt thereof.

Also provided are compounds according to Formula I', or pharmaceutically effective salt thereof:

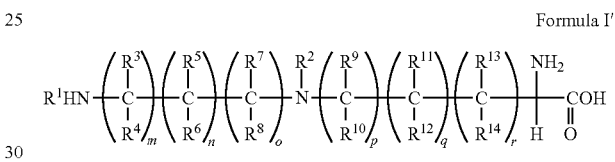

Formula I' wherein:

$R^1$ is selected from the group consisting of hydrogen, —$(C_1$-$C_8)$alkyl, —$(C_1$-$C_8)$alkenyl, —$(C_1$-$C_8)$alkynyl, unsubstituted or substituted -ara$(C_1$-$C_6)$alkyl, unsubstituted or substituted -heteroara$(C_1$-$C_6)$alkyl, where the substituents on said substituted ara$(C_1$-$C_6)$alkyl and substituted heteroara$(C_1$-$C_6)$alkyl are selected from the group consisting of halogen, —CN, —$NO_2$, —$NH_2$, —NH$(C_1$-$C_6)$alkyl, —N[$(C_1$-$C_6)$alkyl)]$_2$, —OH, halo$(C_1$-$C_6)$alkyl, —$(C_1$-$C_6)$alkoxy, halo$(C_1$-$C_6)$alkoxy, —SH, thio$(C_1$-$C_6)$alkyl, —$SONH_2$, —$SO_2NH_2$, —SO—$(C_1$-$C_6)$alkyl, —$SO_2$—$(C_1$-$C_6)$alkyl, —$NHSO_2(C_1$-$C_6)$alkyl, and —$NHSO_2NH_2$;

$R^2$ is selected from the group consisting of hydrogen, —$(C_1$-$C_8)$alkyl, —$(C_1$-$C_8)$alkenyl, —$(C_1$-$C_8)$alkynyl, unsubstituted or substituted -ara$(C_1$-$C_6)$alkyl, unsubstituted or substituted -heteroara$(C_1$-$C_6)$alkyl, where the substituents on said substituted ara$(C_1$-$C_6)$alkyl and substituted heteroara$(C_1$-$C_6)$alkyl are selected from the group consisting of halogen, —CN, —$NO_2$, —$NH_2$, —OH, halo$(C_1$-$C_6)$alkyl, —$(C_1$-$C_6)$alkoxy, halo$(C_1$-$C_6)$alkoxy, —SH, thio$(C_1$-$C_6)$alkyl, —$SONH_2$, —$SO_2NH_2$, —SO—$(C_1$-$C_6)$alkyl, —$SO_2$—$(C_1$-$C_6)$alkyl, —$NHSO_2(C_1$-$C_6)$alkyl, and —$NHSO_2NH_2$;

$R^3$, $R^4$, $R^7$, $R^8$, $R^9$, $R^{10}$, $R^{13}$, and $R^{14}$ are independently selected from the group consisting of hydrogen and —$(C_1$-$C_6)$alkyl;

$R^5$ and $R^6$ are independently selected from the group consisting of hydrogen, —$(C_1$-$C_6)$alkyl and —OH, provided that both $R^5$ and $R^6$ cannot be —OH;

$R^{11}$ and $R^{12}$ are independently selected from the group consisting of hydrogen, —$(C_1$-$C_6)$alkyl and —OH, provided that both $R^{11}$ and $R^{12}$ cannot be —OH;

m is an integer from 1 to 4;
n is an integer from zero to 4
o is an integer from zero to 4;
p is an integer from 1 to 4;

q is an integer from zero to 4; and
r is an integer from zero to 4;
provided:
(i) when the sum of p+q+r is 1, then sum of m+n+o is 5 or greater;
(ii) when the sum of p+q+r is 2, then sum of m+n+o is 5 or greater;
(iii) when the sum of p+q+r is 3, the sum of m+n+o is 3, or is 5 or greater; and
(iv) when the sum of p+q+r is 4, the sum of m+n+o is either 3, or is 6 or greater.

According to certain embodiments of the compound according to Formula I', $R^1$ and $R^2$ are independently selected from the group consisting of hydrogen and —($C_1$-$C_8$)alkyl.

According to certain embodiments of the compound according to Formula I', or pharmaceutically effective salt thereof, each of $R^3$, $R^4$, $R^5$, $R^6$, $R^7$, and $R^8$ is independently selected from hydrogen and —($C_1$-$C_8$)alkyl. In certain such embodiments, each of $R^9$, $R^{10}$, $R^{11}$, $R^{12}$, $R^{13}$, and $R^{14}$ is independently selected from hydrogen and —($C_1$-$C_8$)alkyl.

According to certain embodiments of the compound according to Formula I', or pharmaceutically effective salt thereof, each of $R^9$, $R^{10}$, $R^{11}$, $R^{12}$, $R^{13}$, and $R^{14}$ is independently selected from hydrogen and —($C_1$-$C_8$)alkyl.

According to certain embodiments of the compound according to Formula I', or pharmaceutically effective salt thereof, the sum of m+n+o is in the range of from 2 to 10, and the sum of p+q+r is in the range of from 1 to 10.

According to certain embodiments of the compound according to Formula I', or pharmaceutically effective salt thereof, m is 3; p is 4; each of n, o, q and r is zero. According to certain such embodiments $R^3$, $R^4$, $R^9$, and $R^{10}$ are independently selected from hydrogen and —($C_1$-$C_8$)alkyl. According to certain such embodiments, $R^1$ and $R^2$ are independently selected from the group consisting of hydrogen and —($C_1$-$C_8$)alkyl. In certain such embodiments, $R^1$, $R^2$, $R^3$, $R^4$, $R^9$, and $R^{10}$ are hydrogen.

In certain embodiments, the compound of Formula I' is (S)-2-amino-6-((3-aminopropyl)amino)hexanoic acid, or a pharmaceutically effective salt thereof.

According to certain embodiments of the compound according to Formula I', or pharmaceutically effective salt thereof, m is 4; n is 2; o is zero; p is 3; q is 1; and r is zero. In certain such embodiments, $R^3$, $R^4$, $R^5$, $R^6$, $R^9$, $R^{10}$, $R^{11}$, and $R^{12}$ are independently selected from hydrogen and —($C_1$-$C_8$)alkyl. In certain such embodiments, $R^1$ and $R^2$ are independently selected from the group consisting of hydrogen and —($C_1$-$C_8$)alkyl. In certain such embodiments, $R^1$, $R^2$, $R^3$, $R^4$, $R^5$, $R^6$, $R^9$, $R^{10}$, $R^{11}$, and $R^{12}$ are hydrogen.

In certain embodiments, the compound of Formula I' is (S)-2-amino-5-((6-aminohexyl)amino)pentanoic acid, or a pharmaceutically effective salt thereof.

According to certain embodiments of the compound according to Formula I', or pharmaceutically effective salt thereof, m is 4; n is 1; o is zero; p is 3; q is 1; and r is zero. In certain such embodiments, $R^3$, $R^4$, $R^5$, $R^6$, $R^9$, $R^{10}$, $R^{11}$, and $R^{12}$ are independently selected from hydrogen and —($C_1$-$C_8$)alkyl. In certain such embodiments, $R^1$ and $R^2$ are independently selected from the group consisting of hydrogen and —($C_1$-$C_8$)alkyl. In certain such embodiments, $R^1$, $R^2$, $R^3$, $R^4$, $R^5$, $R^6$, $R^9$, $R^{10}$, $R^{11}$, and $R^{12}$ are hydrogen.

In certain embodiments, the compound of Formula I' is (S)-2-amino-5-((5-aminopentyl)amino)pentanoic acid, or a pharmaceutically effective salt thereof.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

in reducing overnutrition-induced GLUT4 carbonylation in adipose tissue of treated individuals. Animals received high fat diet (HFD) with and without (S)-2-amino-6-((3-aminopropyl)amino)hexanoic acid dihydrochloride ("APL"). Error bars represent mean±s.e.m. Statistics were performed using a two-tail Students t-test. The significance level is **p<0.02.

Figure 8A:
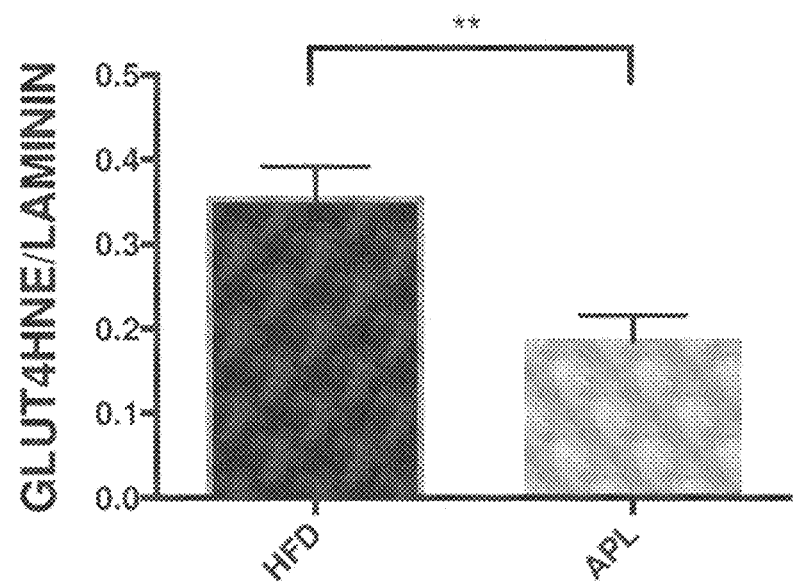
FIG. 8A is a graph of the effect of (S)-2-amino-6-((3-aminopropyl)amino)hexanoic acid dihydrochloride ("APL")
Figure 8B:
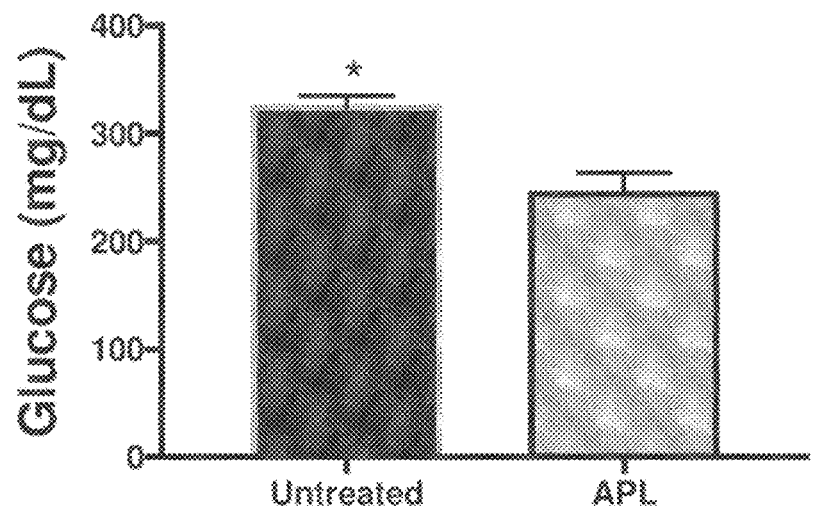

FIG. 8B is a graph of the effect of S)-2-amino-6-((3-aminopropyl)amino)hexanoic acid dihydrochloride ("APL") in reduced fasting glucose levels in animals receiving a high fat diet. Animals received high fat diet (HFD) with and without (S)-2-amino-6-((3-aminopropyl)amino)hexanoic acid dihydrochloride ("APL"). Error bars represent mean±s.e.m. Statistics were performed using a two-tail Students t-test. The significance level is *p<0.05. "Untreated" received HFD and vehicle.

Figure 8C:
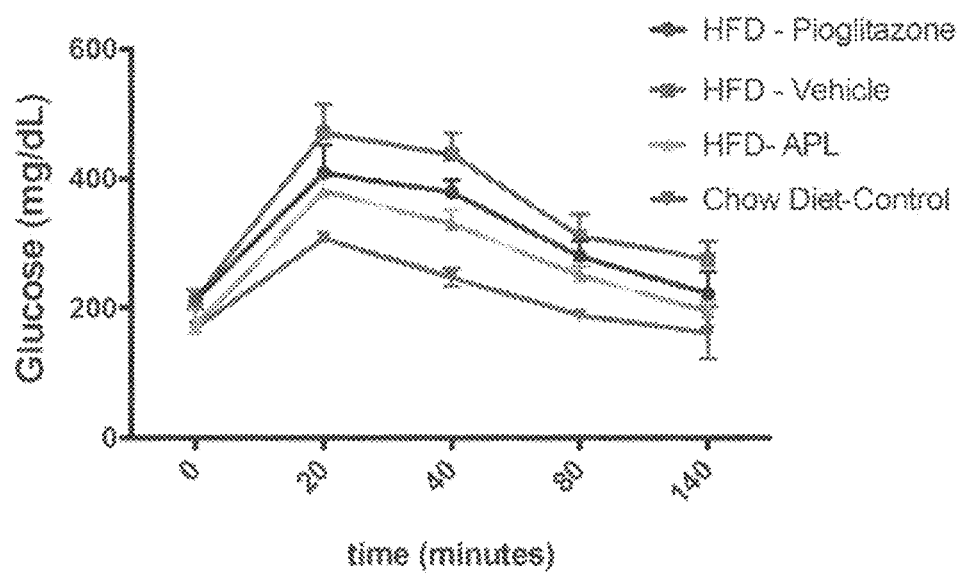

FIG. 8C is a plot of a glucose time test on mice receiving the following treatments: (i) high fat diet (HFD)+poglitazone, (ii) HFD+vehicle, (iii) HFD+(S)-2-amino-6-((3-aminopropyl)amino)hexanoic acid dihydrochloride and (HFD-APL) and (iv) Chow Diet-Control. Data points represent mean±s.e.m.

Figure 8D:
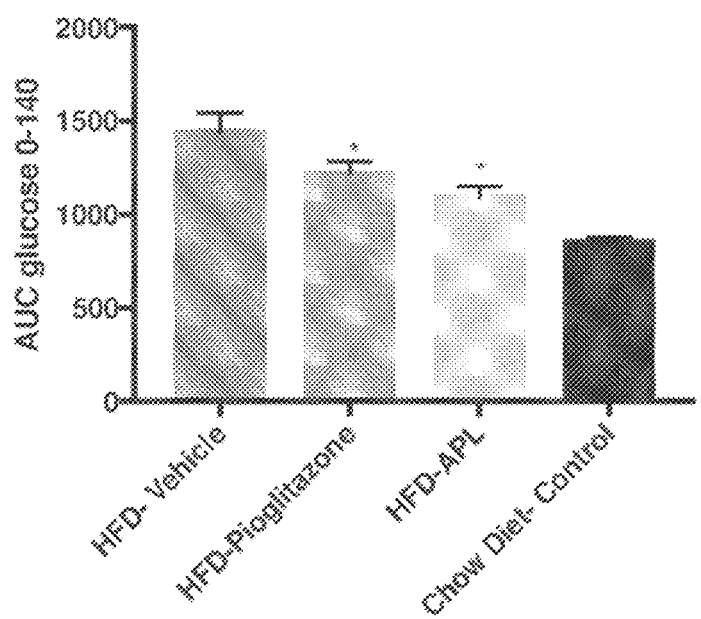

FIG. 8D shows the areas under the curves calculated from the curves of FIG. 8C. Error bars represent mean±s.e.m. Statistics were performed using a two-tail Students t-test. The significance level is *p<0.05.

Figure 9:
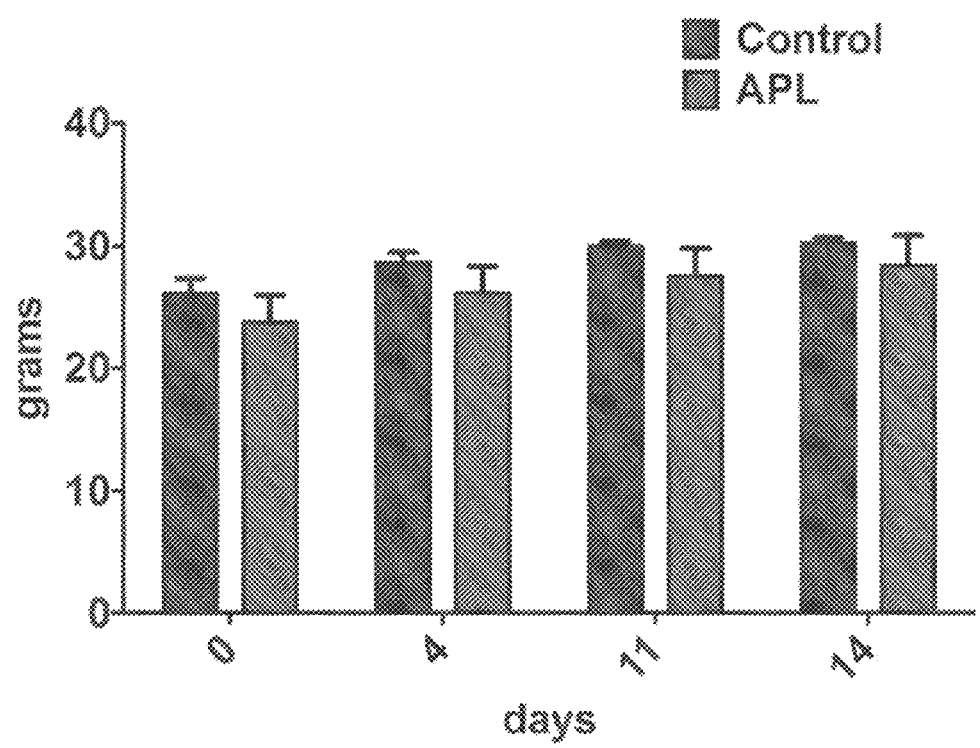

FIG. 9 is a graph of the body weight of diet-induced (HFD) obese mice over two weeks during treatment with (10 mg/kg/day) and without ("Control") the drug (S)-2-amino-6-((3-aminopropyl)amino)hexanoic acid dihydrochloride ("APL").

Figure 10:
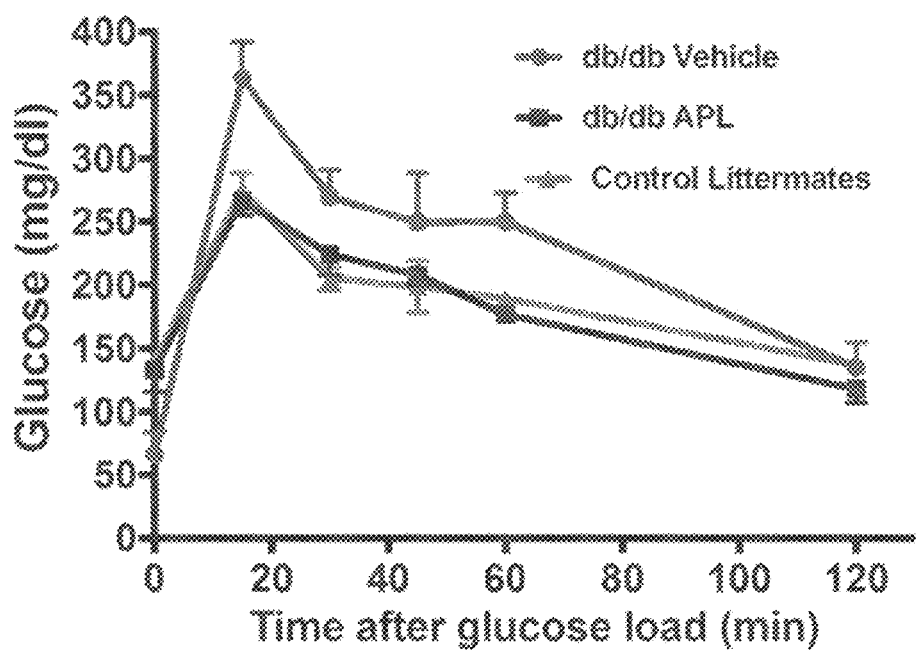

FIG. 10 is plot of a glucose tolerance test in (i) db/db mice receiving 50 mg/kg b.i.d p.o. (S)-2-amino-6-((3-aminopropyl)amino)hexanoic acid dihydrochloride ("db/db APL"); (ii) db/db vehicle control-treated mice ("db/db Vehicle"); or (iii) metformin heterozygous littermate control mice ("Control Littermates"). The treatment period was for 7 days.

Figure 11:
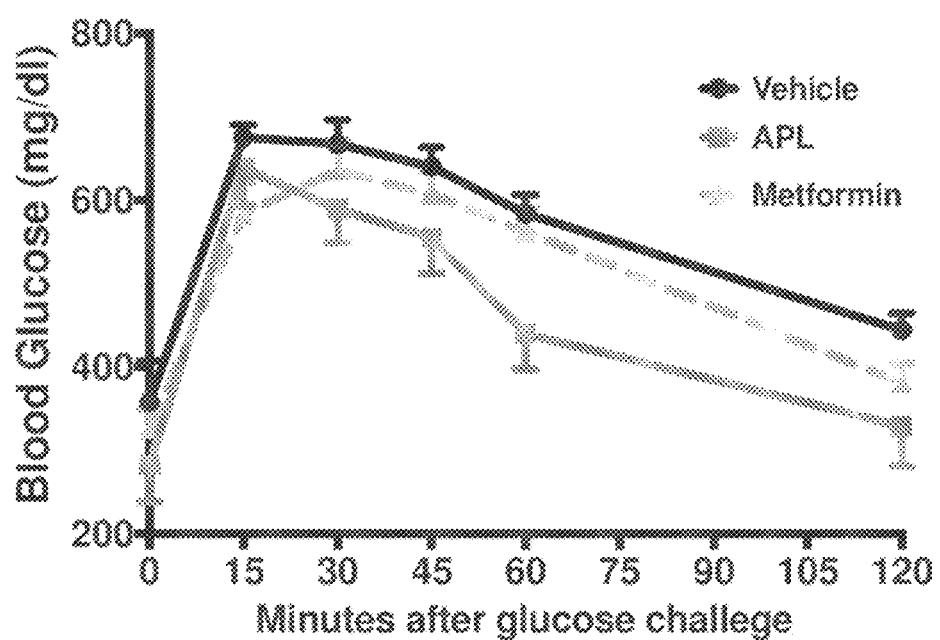

FIG. 11 is a plot of a glucose tolerance test in 6 week old db/db mice treated with (i) 50 mg/kg b.i.d p.o. (S)-2-amino-6-((3-aminopropyl)amino)hexanoic acid dihydrochloride ("APL"); (ii) vehicle ("Vehicle"); or (iii) 50 mg/kg b.i.d. p.o. metformin ("Metformin").

Figure 12:
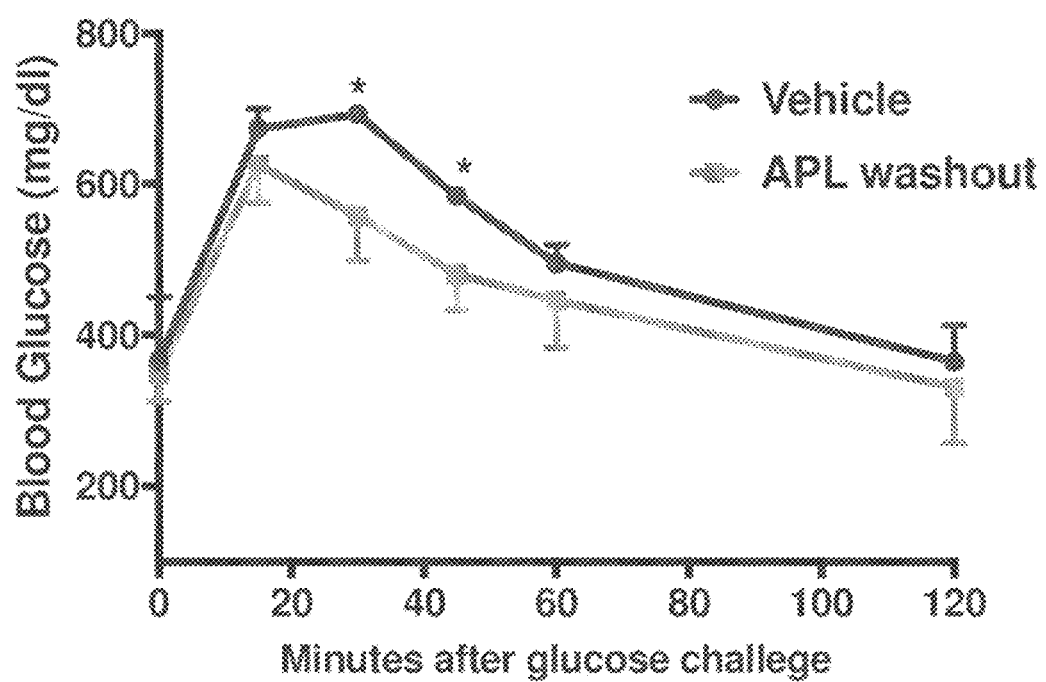

FIG. 12 is a plot of a glucose tolerance test in 6 week old db/db mice treated for 14 days as in FIG. 11, but followed by a no treatment period for an additional 14 days. The glucose tolerance test was conducted at the conclusion of the no treatment period: (i) 50 mg/kg b.i.d p.o. (S)-2-amino-6-((3-aminopropyl)amino)hexanoic acid dihydrochloride ("APL washout"); (ii) vehicle ("Vehicle"); and (iii) 50 mg/kg b.i.d p.o. metformin (data not shown). Statistics were performed using a two-tail Students t-test. The significance level is *p<0.05.

Figure 13:
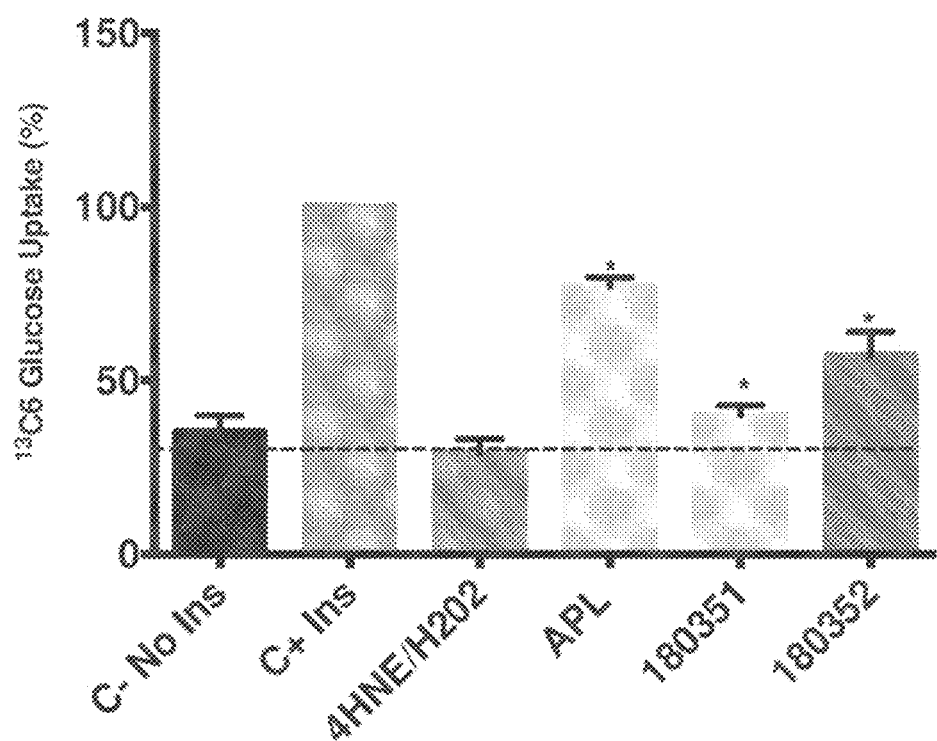

FIG. 13 is a graph of the effect of the drug (S)-2-amino-6-((3-aminopropyl)amino)hexanoic acid dihydrochloride ("APL"), (S)-2-amino-5-((6-aminohexyl)amino)pentanoic acid trihydrochloride (MC180351), and (S)-2-amino-5-((5-aminopentyl)amino)pentanoic acid trihydrochloride (MC180352) in restoring glucose uptake in insulin-stimulated 3T3-L1 cells exposed to 4-HNE and $H_2O_2$: Control cells, no insulin (C− No Ins); control cells, with insulin (C+ Ins); 4HNE+$H_2O_2$-treated cells (4HNE/H2O2); cells treated with APL+4HNE+$H_2O_2$ ("APL"); cells treated with MC80351+4HNE+$H_2O_2$ ("MC180351"); and cells treated with MC180352+4HNE+$H_2O_2$ ("MC180352"). Statistics were performed using ANOVA analysis. The significance level is *p<0.05.

DEFINITIONS

Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

The term "alkyl", by itself or as part of another substituent means, unless otherwise stated, a straight or branched chain hydrocarbyl having the designated number of carbon atoms (i.e., $C_1$-$C_6$ means one to six carbons). Examples include: methyl, ethyl, propyl, isopropyl, butyl, isobutyl, tert-butyl, pentyl, neopentyl, and hexyl. Most preferred is ($C_1$-$C_6$)alkyl, more preferably ($C_1$-$C_3$)alkyl, particularly methyl and ethyl.

The term "alkenyl" employed alone or in combination with other terms, means, unless otherwise stated, a straight chain or branched chain hydrocarbyl having the stated number of carbon atoms, and containing one or more double bonds. Examples include ethenyl (vinyl), propenyl (allyl), crotyl, isopentenyl, butadienyl, 1,3-pentadienyl, and 1,4-pentadienyl. A functional group representing an alkenyl is exemplified by —$CH_2$—CH=$CH_2$—.

The term "alkynyl" employed alone or in combination with other terms, means, unless otherwise stated, a straight chain or branched chain hydrocarbyl having the stated number of carbon atoms, and containing on or more triple bonds.

The term "alkoxy" employed alone or in combination with other terms means, unless otherwise stated, an alkyl group, as defined above, connected to the rest of the molecule via an oxygen atom, such as, for example, methoxy, ethoxy, 1-propoxy, 2-propoxy (isopropoxy) and the higher homologs and isomers. The alkyl portion of the alkoxy group can have a designated number of carbon atoms as defined for alkyl groups above. Preferred are ($C_1$-$C_6$)alkoxy, more preferably ($C_1$-$C_3$)alkoxy, particularly methoxy and ethoxy.

The term "aromatic" refers to a carbocycle or heterocycle having one or more polyunsaturated rings having aromatic character (i.e. having (4n+2) delocalized π (pi) electrons where n is an integer).

The term "aryl" refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "aralkyl" group refers to an alkyl group substituted with an aryl group.

An "effective amount" as used herein, means an amount which provides the indicated therapeutic or prophylactic benefit, i.e., an amount that results in the treatment and/or prevention of insulin resistance and/or an increase in insulin sensitivity, or treatment and/or prevention if insulin resistance disorder. It is understood, however, that the full therapeutic effect does not necessarily occur by administration of one dose, and may occur only after administration of a series of doses. Thus, an effective amount may be administered in one or more administrations. In the context of therapeutic or prophylactic applications, the amount of active agent administered to the subject will depend on the type and severity of the disease or condition and on the characteristics of the subject, such as general health, age, sex, body weight and tolerance to drugs. It will also depend on the degree, severity and type of disease or condition. The skilled artisan will be able to determine appropriate dosages depending on these and other factors. The compounds of Formula I can also be administered in combination with one or more additional therapeutic compounds.

The terms "halo" or "halogen" by themselves or as part of another substituent mean, unless otherwise stated, a fluorine, chlorine, bromine, or iodine atom. Preferably, a halogen includes fluorine, chlorine, or bromine, more preferably, fluorine or chlorine.

The term "heteroaralkyl" group refers to an alkyl group substituted with a heteroaryl group.

The term "heterocycle" or "heterocyclyl" or "heterocyclic" by itself or as part of another substituent means, unless otherwise stated, an unsubstituted or substituted, mono- or multi-cyclic heterocyclic ring system which consists of carbon atoms and at least one heteroatom selected from the group consisting of N, O, and S. The heterocycle typically contains from five to ten ring atoms. The heterocycle system may be attached to another atom, unless otherwise stated, at any heteroatom or carbon atom of the heterocyclic system which affords a structural isomer.

The term "heteroaryl" or "heteroaromatic" refers to a heterocycle having aromatic character.

The term "hydrocarbyl", by itself or as part of another substituent means, unless otherwise stated, a straight or branched chain hydrocarbon having the number of carbon atoms designated (i.e. $C_1$-$C_6$ means one to six carbons). Examples include: methyl, ethyl, propyl, isopropyl, butyl, isobutyl, tert-butyl, pentyl, neopentyl, and hexyl. Most preferred is ($C_1$-$C_6$) alkyl, more preferably ($C_1$-$C_3$) particularly methyl and ethyl. The term "unsaturated hydrocarbyl" means a hydrocarbyl that contains at least one double or triple bond.

As used herein, "individual" or "patient" or "subject" (as in the subject of the treatment) means both mammals and non-mammals. Mammals include, for example, humans; non-human primates, e.g. apes and monkeys; dogs; cats; cattle; horses; sheep; and goats. Non-mammals include, for example, fish and birds. The individual is, in one embodiment, a human being. In another embodiment, the individual is a dog.

The term "insulin resistance" has its common meaning in the art. Insulin resistance is a physiological condition where the natural hormone insulin becomes less effective at lowering blood sugars. The resulting increase in blood glucose may raise levels outside the normal range and cause adverse health effects such as metabolic syndrome, dyslipidemia and subsequently type 2 diabetes mellitus.

An "insulin resistance disorder" refers to any disease or condition that is caused by or contributed to by insulin resistance.

The term "haloalkyl" means an alkyl group wherein at least one hydrogen atom is replaced by a halogen atom. The term "perhaloalkyl" means a haloalkyl group wherein all the hydrogen atoms are replaced by halogen atoms. A preferred perhaloalkyl is perfluoroalkyl, particularly —($C_1$-$C_6$)perfluoroalkyl; more preferred is —($C_1$-$C_3$)perfluoroalkyl; most preferred is —$CF_3$.

The term "haloalkoxy" means an alkoxy group wherein at least one hydrogen atom is replaced by a halogen atom. The term "perhaloalkoxy" means a haloalkoxy group wherein all the hydrogen atoms are replaced by halogen atoms. A preferred perhaloalkoxy is perfluoroalkoxy, particularly —($C_1$-$C_6$)perfluoroalkoxy; more preferred is —($C_1$-$C_3$)perfluoroalkoxy; most preferred is —$OCF_3$.

As used herein, the term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. Substituents may include, for example, one of the moieties from the group of halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, alkylsilyl, cycloalkyl, cycloalkylalkyl, heterocycloalkyl, heteroaryl, alkenyl, alkynyl, aryl, and amino groups. Substituents comprising carbon chains preferably contain 1-6, more preferably 1-3, most preferably 1-2, carbon atoms.

To "treat" a disease as the term is used herein, means to reduce the frequency or severity of at least one sign or symptom of a disease or disorder experienced by a subject. Treating may include the postponement of further disease progression, or reduction in the severity of symptoms that have or are expected to develop, ameliorating existing symptoms and preventing additional symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DETAILED DESCRIPTION OF THE INVENTION

Embodiments of the present invention are described below. It is, however, expressly noted that the present invention is not limited to these embodiments, but rather the intention is that modifications that are apparent to the person skilled in the art and equivalents thereof are also included.

Figure 1A:
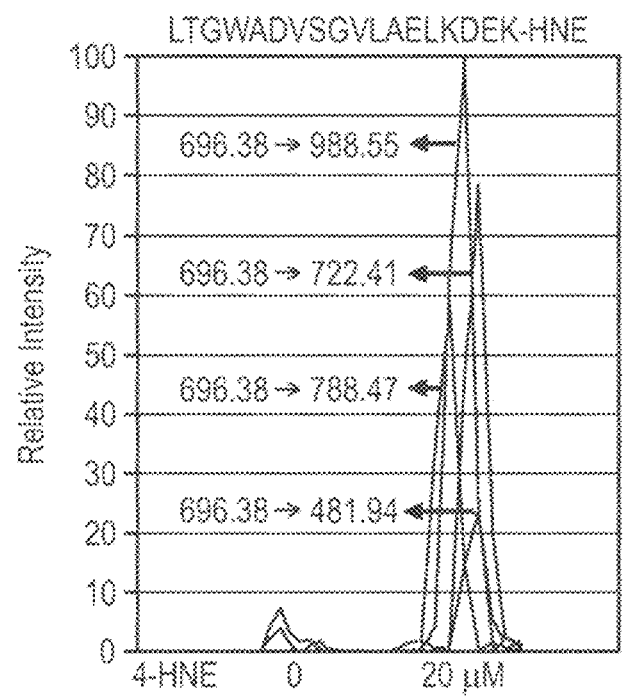
FIG. 1A presents multiple reaction monitoring (MRM) data showing an increase in the transitions of HNE-induced K264-HNE adducts in 3T3-L1 cells overexpressing GLUT4. The cells were treated with 20 μM 4-HNE for 4 hours. The MRM data was then used to calculate the amounts of carbonylated GLUT4.
Figure 1B:
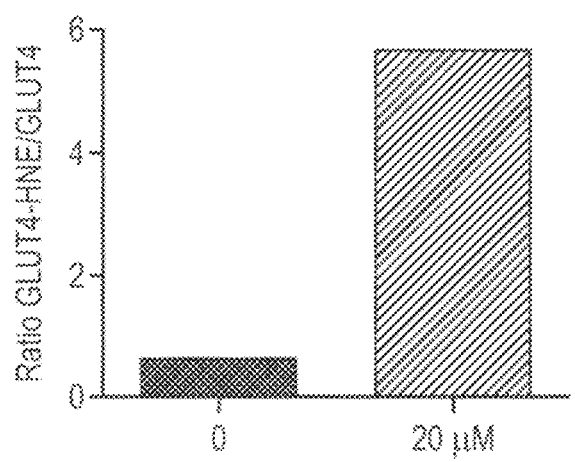
FIG. 1B shows the carbonylated GLUT4 data calculated from the MRM data in FIG. 1A. Four transitions of the GLUT4 peptide found in humans were used for quantitation.
Figure 3A:
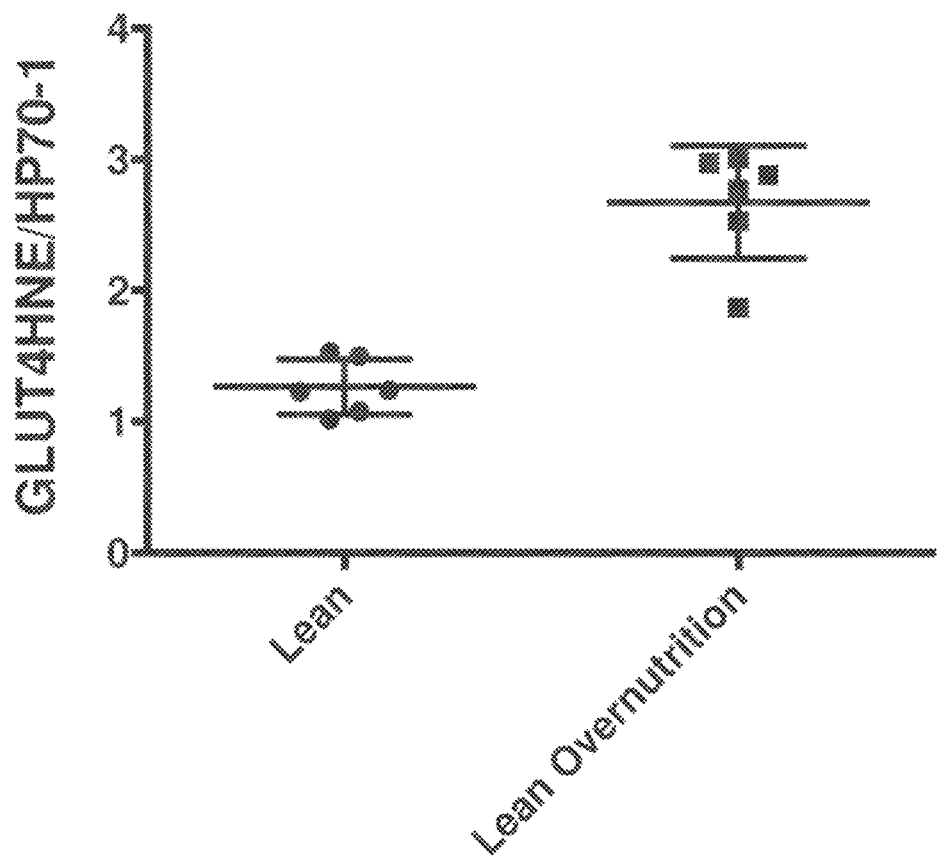
FIG. 3A is a plot of the level of GLUT4 carbonylation as determined by detection of the adducted GLUT4 fragment LTGWADVSGVLAELKDEK-4HNE (SEQ ID NO:2), constituting GLUT4 amino acids 247-264 (LTGWADVSGVLAELKDEK, SEQ ID NO: 1), in adipose tissue from lean individuals, and from lean over-nourished insulin-resistant individuals. HP70-1 was utilized as an internal control.
Figure 3B:
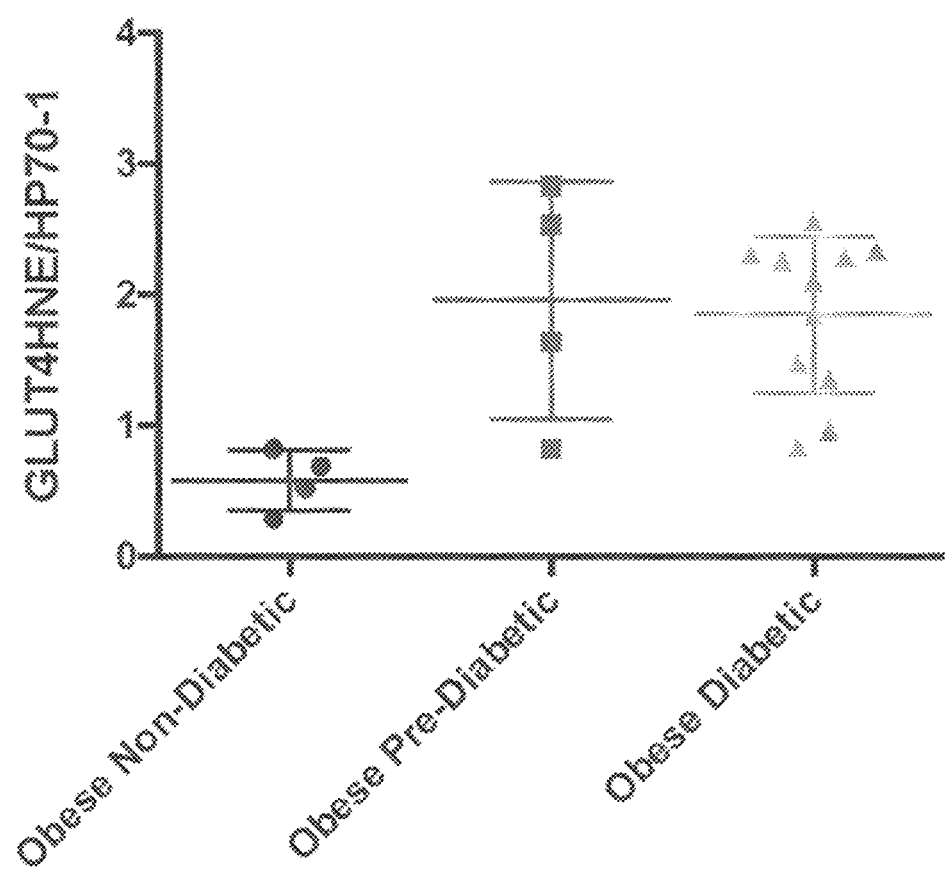
FIG. 3B is a plot of the level GLUT4 carbonylation as determined by detection of the adducted GLUT4 fragment LTGWADVSGVLAELKDEK-4HNE (SEQ ID NO:2), in adipose tissue from obese non-diabetic, obese pre-diabetic, and obese diabetic individuals. HP70-1 was utilized as an internal control.
Figure 3C:
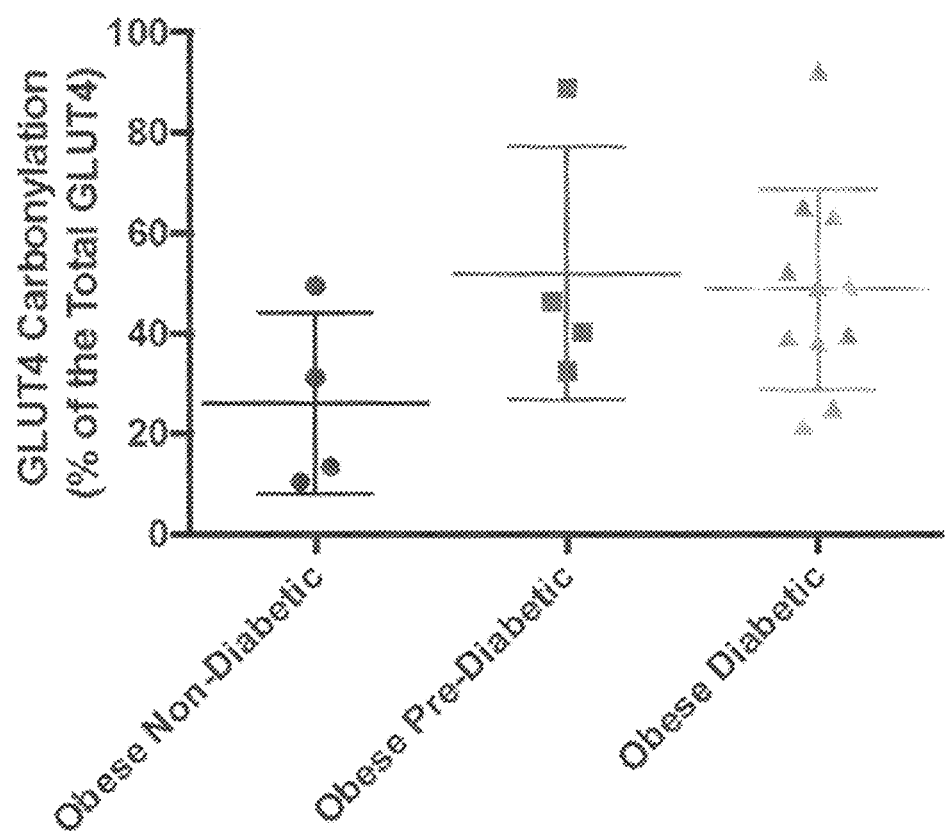
FIG. 3C shows the percentage of GLUT 4 that is carbonylated in adipose tissue of the obese non-diabetic, obese pre-diabetic, and obese diabetic groups of individuals of FIGS. 3A-3B.

Certain conditions such as overnutrition can lead to oxidative stress, and the generation of reactive aldehydes such as 4-HNE, which react with cysteine, lysine and histidine residues of proteins via Michael addition and Schiff base formation. 4-HNE can form HNE-Michaels adducts on GLUT4, the major insulin-facilitated glucose transporter in adipose tissue. As shown in FIG. 1A, 3T3-L1 adipocytes retrovirally transduced to overexpress the GLUT4-SNAP protein formed a K264-HNE GLUT4 adduct upon treatment with 4-HNE. The amounts of carbonylated protein is shown in FIG. 1B. The same K264-HNE GLUT4 adduct is elevated in the fat tissue of human pre-diabetic and diabetic individuals (FIG. 3B, 3C).

Figure 2:
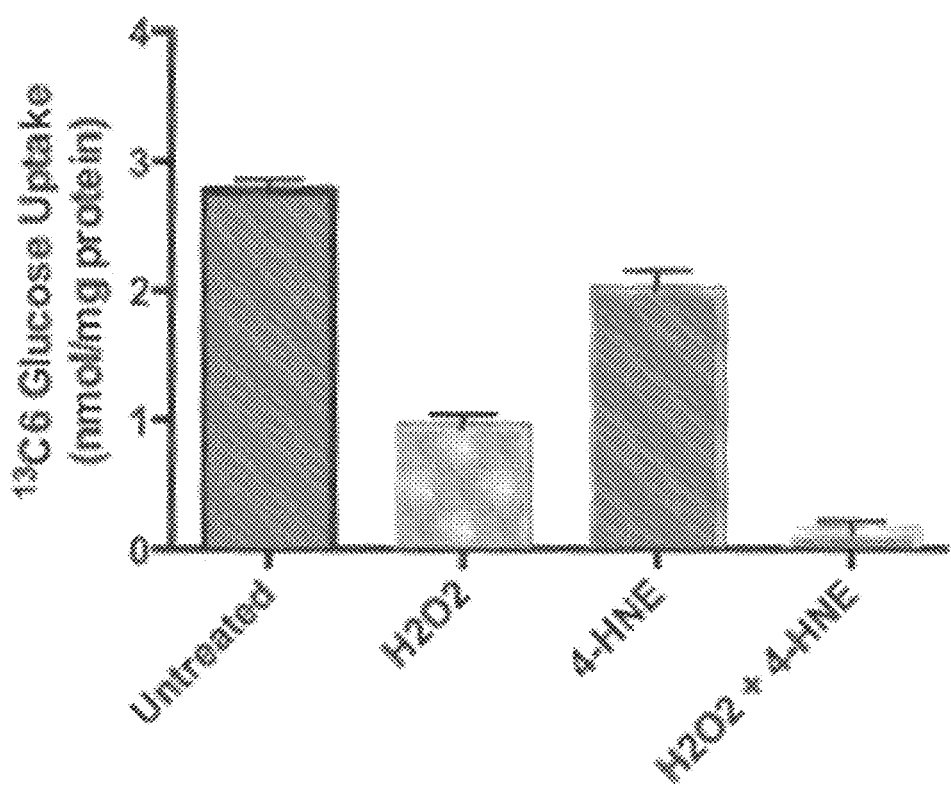
FIG. 2 shows the effect of 4-HNE and $H_2O_2$ on insulin-induced glucose uptake by 3T3-L1 adipocytes. Glucose uptake was reduced by 32% and 66% with 4-HNE and $H_2O_2$ treatment, respectively. The combination of both 4-HNE and $H_2O_2$ resulted in a 98% decrease in glucose uptake.

HNE-adduction leads to loss of GLUT-4 function, and development of adipocyte insulin resistance, as indicated by the reduction of adipocyte glucose uptake upon insulin stimulation. As shown in FIG. 2, glucose uptake by 3T3-L1 adipocytes was reduced upon 4-HNE and $H_2O_2$ treatment, followed by insulin stimulation.

It has been surprisingly found that compounds of Formula I are effective in increasing insulin sensitivity and/or reducing insulin resistance.

Figure 6A:
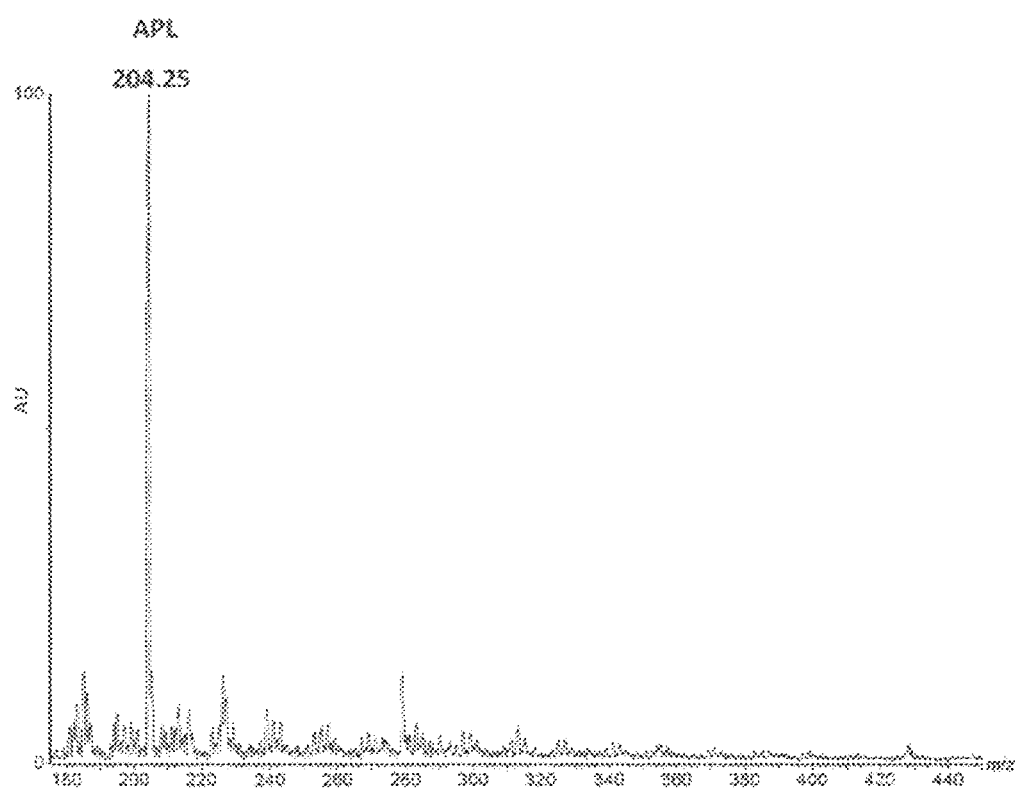
FIG. 6A depicts mass spectrometry data for APL prior to incubation with 4-NHE.
Figure 6B:
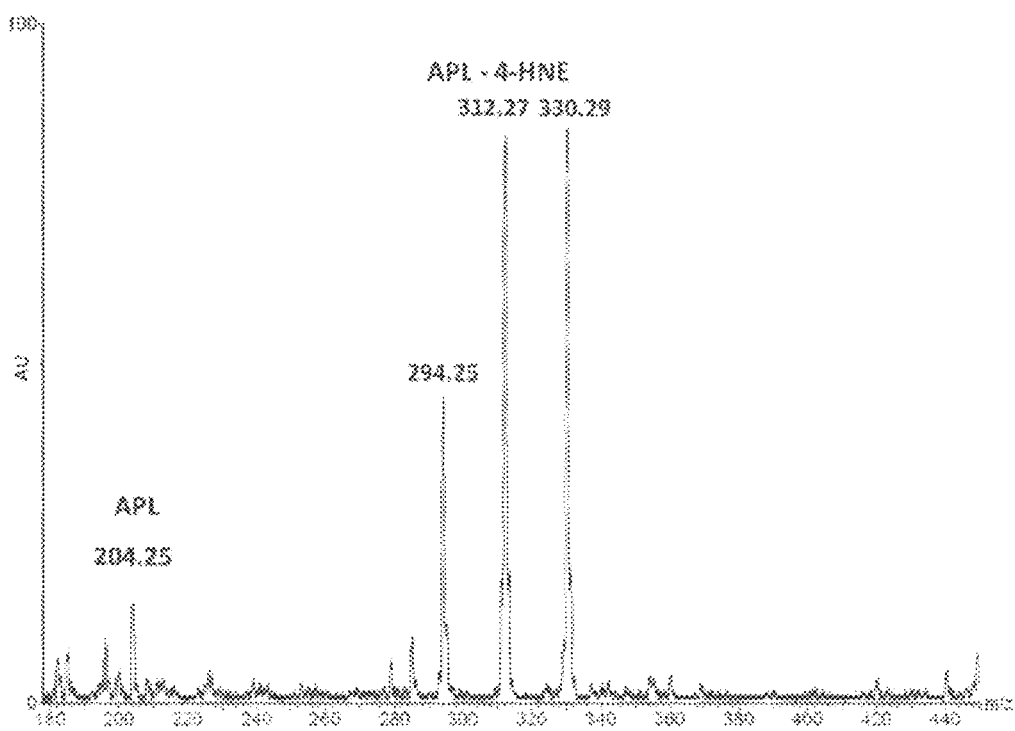
FIG. 6B depicts mass spectrometry data for APL after 1 hr incubation with 4-NHE. The data show that APL forms an adduct with 4-NHE.

Compounds of Formula I have been found to overcome adipocyte glucose uptake impairment by restoring insulin sensitivity. Without wishing to be bound by any theory, compounds of Formula I form adducts with reactive aldehydes such as 4-HNE, thereby diverting 4-HNE from damaging proteins such as GLUT-4, by carbonylation. As shown in FIGS. 6A and 6B, the compound (S)-2-amino-6-((3-aminopropyl)amino)hexanoic acid dihydrochloride, a compound of Formula I, forms an adduct with 4-HNE, thereby diverting 4-HNE from damaging GLUT-4 by carbonylation. It has the effect of reversing overnutrition-induced glucose uptake impairment. Restoration of GLUT-4 function results in enhancement or restoration of adipocyte insulin sensitivity and the resumption or enhancement of glucose uptake.

Impaired glucose tolerance as measured by glucose tolerance tests is dramatically improved in comparison to the only moderate glucose tolerance-improving effect of pioglitazone (Example 11). The compound is also better in reducing impaired glucose tolerance than metformin (Examples 12-13). Metformin is a first-line medication for the treatment of type 2 diabetes.

The compounds reduction impaired glucose tolerance in both pre-diabetes and diabetes stages, indicating that the compounds may be used to treat both pre-diabetes (Example 12), and diabetes wherein the diabetic phenotype has been established.

Studies that follow (Example 13) indicate that the compounds are diabetes-modulating, and do not merely mask the disease.

Compounds of Formula I can be used to treat both pre-diabetes, and diabetes wherein the diabetic phenotype has been established. The compounds are believed effective in counteracting glucose uptake impairment in cells induced by overnutrition.

The compounds of Formula I are administered to increase insulin sensitivity and/or reduce insulin resistance in subjects in need of such treatment.

Insulin is produced in the body upon the initiation of glucose release into the bloodstream from carbohydrate digestion. Under normal circumstances, the cells of the body respond to stimulus by insulin by taking up glucose, for use as energy. The major cell types that require insulin to absorb glucose are fat cells and muscle cells. When the body produces insulin under conditions of insulin resistance, these cells in the body are resistant to stimulation by insulin, leading to high blood sugar. Beta cells in the pancreas increase their production of insulin, further contributing to a high blood insulin level. Elevated blood insulin level, left may lead to reduced insulin sensitivity. T2DM, in particular, develops from insulin resistance, meaning that the normally secreted dose of insulin is no longer sufficient to control blood glucose levels.

According to the present invention, any of the pathologies flowing from reduced insulin sensitivity (or insulin resistance) may be treated. The compounds of Formula I are thus useful for treating any condition associated with the loss of the relevant target cell's sensitivity to regulation by insulin. The compounds of Formula I are thus believed useful in the treatment of insulin resistance disorders. An "insulin resistance disorder" refers to refers to any disease or condition that is caused by or contributed to by insulin resistance. Examples include: diabetes, obesity, metabolic syndrome, insulin resistance, insulin-resistance syndromes, syndrome X, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis.

In addition to pathological conditions associated with insulin resistance, the compounds of Formula I may be administered for treatment of conditions of low insulin production, e.g. cases of IDDM where some finite level of insulin production remains, albeit at reduced amounts.

Compounds

Compounds for use in a method for treating insulin resistance have the structure of Formula I, Formula I

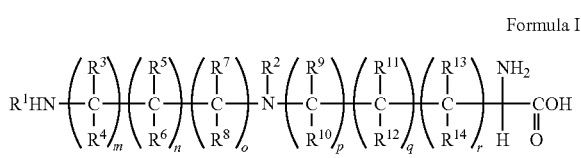

and pharmaceutically acceptable salts thereof,
wherein:
$R^1$ is selected from the group consisting of hydrogen, —$(C_1$-$C_8)$alkyl, —$(C_1$-$C_8)$alkenyl, —$(C_1$-$C_8)$alkynyl, unsubstituted or substituted -ara$(C_1$-$C_6)$alkyl, unsubstituted or substituted -heteroara$(C_1$-$C_6)$alkyl, where the substituents on said substituted ara$(C_1$-$C_6)$alkyl and substituted heteroara $(C_1$-$C_6)$alkyl are selected from the group consisting of halogen, —CN, —$NO_2$, —$NH_2$, —NH$(C_1$-$C_6)$alkyl, —N[$(C_1$-$C_6)$alkyl]2, —OH, halo$(C_1$-$C_6)$alkyl, —$(C_1$-$C_6)$ alkoxy, halo($C_1$-$C_6$)alkoxy, —SH, thio($C_1$-$C_6$)alkyl, —SONH$_2$, —SO$_2$NH$_2$, —SO—($C_1$-$C_6$)alkyl, —SO$_2$—($C_1$-$C_6$)alkyl, —NHSO$_2$($C_1$-$C_6$)alkyl, and —NHSO$_2$NH$_2$;

$R^2$ is selected from the group consisting of hydrogen, —($C_1$-$C_8$)alkyl, —($C_1$-$C_8$)alkenyl, —($C_1$-$C_8$)alkynyl, unsubstituted or substituted -ara($C_1$-$C_6$)alkyl, unsubstituted or substituted -heteroara($C_1$-$C_6$)alkyl, where the substituents on said substituted ara($C_1$-$C_6$)alkyl and substituted heteroara($C_1$-$C_6$)alkyl are selected from the group consisting of halogen, —CN, —NO$_2$, —NH$_2$, —OH, halo($C_1$-$C_6$)alkyl, —($C_1$-$C_6$)alkoxy, halo($C_1$-$C_6$)alkoxy, —SH, thio($C_1$-$C_6$)alkyl, —SONH$_2$, —SO$_2$NH$_2$, —SO—($C_1$-$C_6$)alkyl, —SO$_2$—($C_1$-$C_6$)alkyl, —NHSO$_2$($C_1$-$C_6$)alkyl, and —NHSO$_2$NH$_2$;

$R^3$, $R^4$, $R^7$, $R^8$, $R^9$, $R^{10}$, $R^{13}$, and $R^{14}$ are independently selected from the group consisting of hydrogen and —($C_1$-$C_6$)alkyl;

$R^5$ and $R^6$ are independently selected from the group consisting of hydrogen, —($C_1$-$C_6$)alkyl and —OH, provided that both $R^5$ and $R^6$ cannot be —OH;

$R^{11}$ and $R^{12}$ are independently selected from the group consisting of hydrogen, —($C_1$-$C_6$)alkyl and —OH, provided that both $R^{11}$ and $R^{12}$ cannot be —OH;

m is 1, 2, 3 or 4;
n is 0, 1, 2, 3 or 4;
o is 0, 1, 2, 3 or 4;
p is 1, 2, 3 or 4;
q is 0, 1, 2, 3 or 4; and
r is 0, 1, 2, 3 or 4.

In certain embodiments, halo($C_1$-$C_6$)alkyl and/or halo($C_1$-$C_6$)alkoxy comprising $R^1$ and/or $R^2$ are selected from perhalo($C_1$-$C_6$)alkyl and perhalo($C_1$-$C_6$).

In certain embodiments, $R^1$ is selected from hydrogen and —($C_1$-$C_8$)alkyl. In certain embodiments, $R^2$ is selected from hydrogen or —($C_1$-$C_8$)alkyl. In certain embodiments, $R^1$ and $R^2$ are independently selected from hydrogen and —($C_1$-$C_8$)alkyl. In the aforementioned embodiments, the —($C_1$-$C_8$)alkyl is preferably —($C_1$-$C_6$)alkyl, more preferably —($C_1$-$C_3$)alkyl, more preferably methyl or ethyl. In certain embodiments, $R^1$ and $R^2$ are hydrogen.

In certain embodiments, each of $R^3$, $R^4$, $R^5$, $R^6$, $R^7$, and $R^8$ is independently selected from hydrogen and —($C_1$-$C_8$)alkyl. The —($C_1$-$C_8$)alkyl is preferably —($C_1$-$C_6$)alkyl, more preferably —($C_1$-$C_3$)alkyl, more preferably methyl or ethyl. In certain embodiments, $R^3$, $R^4$, $R^5$, $R^6$, $R^7$, and $R^8$ are hydrogen.

In certain embodiments, each of $R^9$, $R^{10}$, $R^{11}$, $R^{12}$, $R^{13}$, and $R^{14}$ is independently selected from hydrogen and —($C_1$-$C_8$)alkyl. The —($C_1$-$C_8$)alkyl is preferably —($C_1$-$C_6$)alkyl, more preferably —($C_1$-$C_3$)alkyl, more preferably methyl or ethyl. In certain embodiments, $R^9$, $R^{10}$, $R^{11}$, $R^{12}$, $R^{13}$, and $R^{14}$ are hydrogen.

In certain embodiments, each of $R^3$ through $R^{14}$ are independently selected from hydrogen and —($C_1$-$C_8$)alkyl, according to the above schemes. In certain embodiments, $R^3$ through $R^{14}$ are hydrogen.

In some embodiments of compounds of Formula I, the sum of m+n+o is in the range of from 2 to 10, 9, 8, 7, 6, 5, 4 or 3; in the range of from 3 to 10, 9, 8, 7, 6, 5 or 4; or in the range of from 4 to 10, 9, 8, 7, 6 or 5. In some embodiments, the sum of m+n+o is 12, 11, 10, 9, 8, 7, 6, 5, 4, 3 or 2.

In some embodiments of compounds of Formula I, the sum of p+q+r is in the range of from 1 to 10, 9, 8, 7, 6, 5, 4, 3 or 2; in the range of from 2 to 10, 9, 8, 7, 6, 5, 4 or 3; in the range of from 3 to 10, 9, 8, 7, 6, 5 or 4; or in the range of from 4 to 10, 9, 8, 7, 6 or 5. In some embodiments, the sum of p+q+r is 12, 11, 10, 9, 8, 7, 6, 5, 4, 3, 2 or 1.

In some embodiments of the aforesaid embodiments defining sums of m+n+o and/or defining sums of p+q+r, each of $R^3$ through $R^{14}$ are independently selected from hydrogen and —($C_1$-$C_8$)alkyl. In certain embodiments, $R^3$ through $R^{14}$ are hydrogen.

In certain preferred embodiments of a compound of Formula I, m is 3; p is 4; and each of n, o, q and r is zero. In certain such embodiments, $R^3$, $R^4$, $R^9$, and $R^{10}$ are independently selected from hydrogen and —($C_1$-$C_8$)alkyl, preferably hydrogen. In certain such embodiments, $R^1$ and $R^2$ may be independently selected from hydrogen and —($C_1$-$C_8$)alkyl, preferably hydrogen.

In another embodiment, novel compounds and pharmaceutically effective salts thereof are provided according to Formula I'

Formula I'

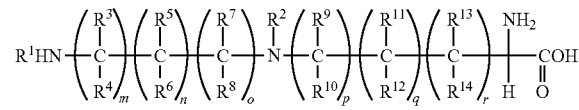

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m, n, o, p, q, and r defined as above for Formula I, provided:

(i) when the sum of p+q+r is 1, then sum of m+n+o is 5 or greater;
(ii) when the sum of p+q+r is 2, the sum of m+n+o is 5 or greater;
(iii) when the sum of p+q+r is 3, the sum of m+n+o is 3, or is greater; and
(iv) when the sum of p+q+r is 4, the sum of m+n+o is either 3, or is 6 or greater.

In certain embodiments, when the sum of p+q+r is 2, the sum of m+n+o is 6 or greater, 7 or greater, 8 or greater, 9 or greater or 10 or greater.

In certain embodiments, when the sum of p+q+r is 3, the sum of m+n+o is 5 or greater, 6 or greater, 7 or greater, 8 or greater, 9 or greater or 10 or greater.

In certain embodiments, when the sum of p+q+r is 4, the sum of m+n+o is 7 or greater, 8 or greater, 9 or greater or 10 or greater.

In preferred embodiments, when the sum of p+q+r is 4, the sum of m+n+o is 3.

In certain embodiments, where the sum of p+q+r is 1, then the sum of m+n+o is 5 or greater, 6 or greater, 7 or greater, 8 or greater, 9 or greater or 10 or greater.

In certain embodiments of the novel compounds of Formula I', $R^1$ is selected from hydrogen and —($C_1$-$C_8$)alkyl. In certain embodiments, $R^2$ is selected from hydrogen or —($C_1$-$C_8$)alkyl. In certain embodiments, $R^1$ and $R^2$ are independently selected from hydrogen and —($C_1$-$C_8$)alkyl. In the aforementioned embodiments, the —($C_1$-$C_8$)alkyl is preferably —($C_1$-$C_6$)alkyl, more preferably —($C_1$-$C_3$)alkyl, more preferably methyl or ethyl. In certain embodiments, $R^1$ and $R^2$ are hydrogen.

In certain embodiments of the novel compounds of Formula I', each of $R^3$, $R^4$, $R^5$, $R^6$, $R^7$, and $R^8$ is independently selected from hydrogen and —($C_1$-$C_8$)alkyl. The —($C_1$-$C_8$)alkyl is preferably —($C_1$-$C_6$)alkyl, more preferably —($C_1$-$C_3$)alkyl, more preferably methyl or ethyl. In certain embodiments, $R^3$, $R^4$, $R^5$, $R^6$, $R^7$, and $R^8$ are hydrogen.

In certain embodiments of the novel compounds of Formula I', each of $R^9$, $R^{10}$, $R^{11}$, $R^{12}$, $R^{13}$, and $R^{14}$ is independently selected from hydrogen and —($C_1$-$C_8$)alkyl. The —$(C_1-C_8)$alkyl is preferably —$(C_1-C_6)$alkyl, more preferably —$(C_1-C_3)$alkyl, more preferably methyl or ethyl. In certain embodiments, $R^9$, $R^{10}$, $R^{11}$, $R^{12}$, $R^{13}$, and $R^{14}$ are hydrogen.

In certain embodiments of the novel compounds of Formula I', each of $R^3$ through $R^{14}$ are independently selected from hydrogen and —$(C_1-C_8)$alkyl, according to the above schemes. In certain embodiments, $R^3$ through $R^{14}$ are hydrogen.

In some embodiments of the novel compounds of Formula I', the sum of m+n+o is in the range of from 2 to 10, 9, 8, 7, 6, 5, 4 or 3; in the range of from 3 to 10, 9, 8, 7, 6, 5 or 4; or in the range of from 4 to 10, 9, 8, 7, 6 or 5. In some embodiments, the sum of m+n+o is 12, 11, 10, 9, 8, 7, 6, 5, 4, 3 or 2. The selection of the sum of m+n+o is subject to provisos (i), (ii), (iii) and (iv) above, for Formula I'.

In some embodiments of compounds of Formula I', the sum of p+q+r is in the range of from 1 to 10, 9, 8, 7, 6, 5, 4 or 2; in the range of from 2 to 10, 9, 8, 7, 6, 5, 4 or 3; in the range of from 3 to 10, 9, 8, 7, 6, 5 or 4; or in the range of from 4 to 10, 9, 8, 7, 6 or 5. In some embodiments, the sum of p+q+r is 12, 11, 10, 9, 8, 7, 6, 5, 4, 3 or 2. The selection of the sum of p+q+r is subject to provisos (i), (ii), (iii) and (iv), above.

In some of the aforesaid embodiments defining sums of m+n+o and/or defining sums of p+q+r, each of $R^3$ through $R^{14}$ are independently selected from hydrogen and —$(C_1-C_8)$alkyl. In certain embodiments, $R^3$ through $R^{14}$ are hydrogen.

In certain preferred embodiments of a compound of Formula I', m is 3; p is 4; and each of n, o, q and r is zero. The compounds accordingly have the structure of Formula Ic,

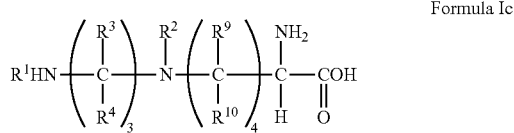

Formula Ic wherein each $R^3$, each $R^4$, each $R^9$, and each $R^{12}$ is independently selected from hydrogen and —$(C_1-C_8)$alkyl. In certain embodiments, $R^3$, $R^4$, $R^9$, and $R^{10}$ are hydrogen. In certain embodiments of compounds of Formula Ic, $R^1$ and $R^2$ are independently selected from the group consisting of hydrogen and —$(C_1-C_8)$alkyl, and are preferably hydrogen. Particularly preferred is the compound (S)-2-amino-6-((3-aminopropyl)amino)hexanoic acid, or a pharmaceutically effective salt thereof. A preferred salt thereof is (S)-2-amino-6-((3-aminopropyl)amino)hexanoic acid dihydrochloride.

In certain preferred embodiments of a compound of Formula I', m is 4; n is 2; p is 3; and each of o, q and r is zero. Particularly preferred is the compound (S)-2-amino-5-((6-aminohexyl)amino)pentanoic acid, or a pharmaceutically effective salt thereof. A preferred salt thereof is (S)-2-amino-5-((6-aminohexyl)amino)pentanoic acid trihydrochloride.

In certain preferred embodiments of a compound of Formula I', m is 4; n is 1; p is 3; and each of o, q and r is zero. Particularly preferred is the compound (S)-2-amino-5-((5-aminopentyl)amino)pentanoic acid, or a pharmaceutically effective salt thereof. A preferred salt thereof is (S)-2-amino-5-((5-aminopentyl)amino)pentanoic acid trihydrochloride.

Synthesis Schemes

Compounds of Formula I may be prepared according to Schemes 1-16 wherein:

A is

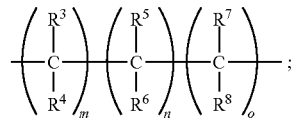

B is

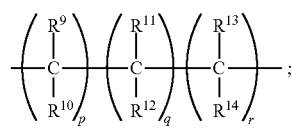

and $R^1$ and $R_2$ are defined as for Formula I.

Compounds of Formula I may be prepared according to the general methods of Schemes 4-8 and 14-16. Certain compounds of Formula I, identified as having the structure of Formula Ia, may be prepared using the general methods shown in Schemes 1-3. Similarly, certain compounds of Formula I, identified as having the structure of Formula Ib, may be prepared using the general methods shown in Schemes 9-13. It may be appreciated that compounds of Formula Ia and Ib are compounds of Formula I wherein m is 1, and $R^3$ and $R^4$ are each hydrogen.

Scheme 1

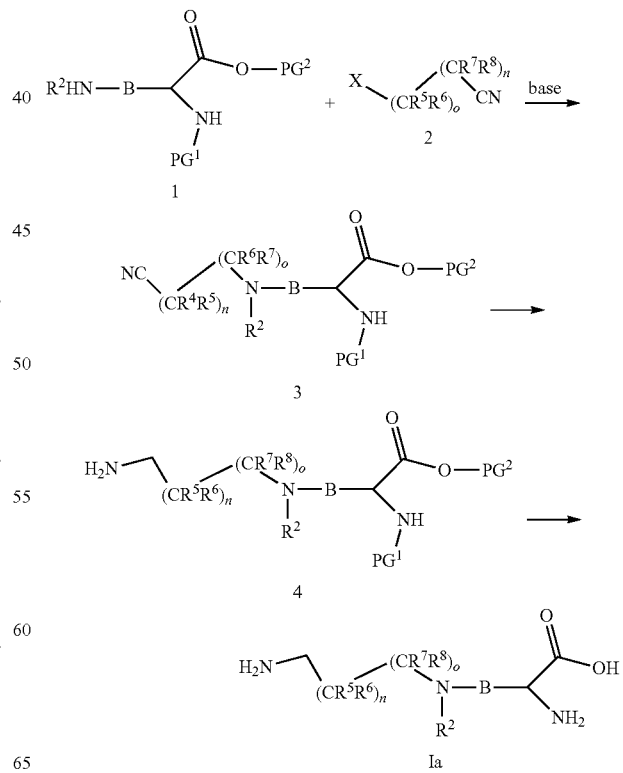

According to Scheme 1, a compound of the formula (1), a known compound or a compound prepared by known means wherein $PG^1$ is a protecting group selected, for example, from the group consisting of triphenylmethyl (trityl), tert-butyloxycarbonyl (BOC), 9-fluorenylmethyloxycarbonyl (FMOC), and carbobenzyloxy (Cbz) and $PG^2$ is selected, for example, from the group consisting of 9-fluorenylmethyl (Fm), $C_{1-6}$ alkyl and $C_{3-7}$ branched alkyl, is reacted with a compound of the formula (2), a known compound or compound prepared by known methods wherein X is a leaving group such as bromine, chlorine, iodine, methanesulfonate, tolylsulfonate, and the like, in the presence of a base such as trimethylamine, diisopropylethylamine, pyridine, potassium carbonate, cesium carbonate, sodium hydroxide, potassium hydroxide, sodium hydride, potassium hydride, lithium diisopropylamide, sodium hexamethyldisilazide, lithium hexamethyldisilazide, potassium t-butoxide, or sodium t-butoxide, and the like, in a solvent such as tetrahydrofuran, 1,4-dioxane, methylene chloride, methanol, ethanol, t-butanol, and the like, optionally with heating, optionally with microwave irradiation, to provide a compound of the formula (3).

According to Scheme 1, a compound of the formula (3) is then reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium, [1,1'-bis(diphenylphosphino) ferrocene]dichloropalladium, platinum on carbon, platinum on barium sulfate, platinum on celite, platinum on calcium carbonate, platinum on barium carbonate, platinum on silica, platinum on alumina, rhodium on carbon, rhodium on barium sulfate, rhodium on celite, rhodium on calcium carbonate, rhodium on barium carbonate, rhodium on silica, rhodium on alumina, and the like, in a solvent such as ethanol, methanol, tetrahydrofuran, 1,4-dioxane, ethyl acetate, benzene, toluene, cyclohexane, N,N-dimethylformamide, and the like, optionally with heating, optionally with microwave irradiation, to provide a compound of the formula (4).

According to Scheme 1, a compound of the formula (4) is then reacted with an acid such as acetic acid, trifluoroacetic acid, hydrochloric acid, sulfuric acid, trifluoromethanesulfonic acid, and the like, optionally in a solvent such as methylene chloride, tetrahydrofuran, 1,4-dioxane, ethanol, or methanol, and the like, optionally with heating, optionally with microwave irradiation, to provide a compound of the formula (Ia). Alternatively, a compound of the formula (4) is reacted with a base such as lithium hydroxide, sodium hydroxide, sodium carbonate, lithium carbonate, piperidine, pyridine, 2,6-lutidine, and the like, in a solvent such as methylene chloride, tetrahydrofuran, 1,4-dioxane, ethanol, or methanol, and the like, optionally with heating, optionally with microwave irradiation, to provide a compound of the formula (Ia). Alternatively, a compound of the formula (4) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, or methanol, and the like, optionally with heating, optionally with microwave irradiation, to provide a compound of the formula (Ia).

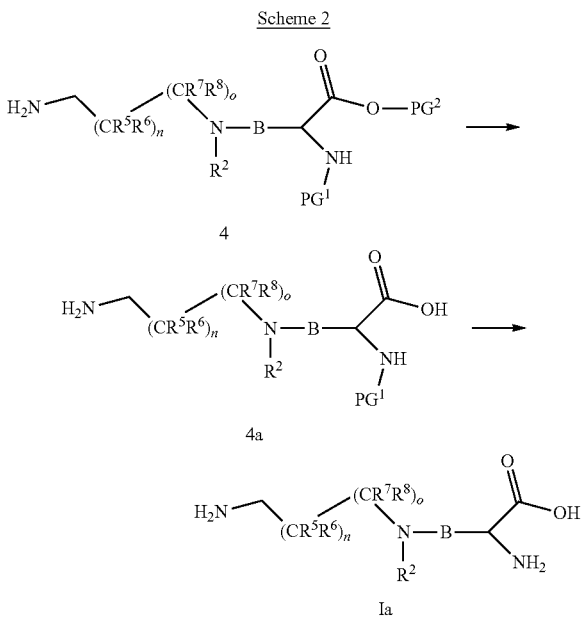

Scheme 2

Alternatively, according to Scheme 2, a compound of the formula (4) is reacted with an acid such as acetic acid, trifluoroacetic acid, hydrochloric acid, sulfuric acid trifluoromethanesulfonic acid, and the like, optionally in a solvent such as methylene chloride, tetrahydrofuran, 1,4-dioxane, ethanol or methanol, and the like, optionally with heating, optionally with microwave irradiation to provide a compound of the formula (4a). Alternatively, according to Scheme 2, a compound of the formula (4) is reacted with a base such as lithium hydroxide, sodium hydroxide, sodium carbonate or lithium carbonate, and the like, in a solvent such as methylene chloride, tetrahydrofuran, 1,4-dioxane, ethanol or methanol, and the like, optionally with heating, optionally with microwave irradiation to provide a compound of the formula (4a).

According to Scheme 2, a compound of the formula (4a) is then reacted with abase such as piperidine, pyridine or 2,6-lutidine, and the like, in a solvent such as methylene chloride, tetrahydrofuran, 1,4-dioxane, ethanol or methanol, and the like, optionally with heating, optionally with microwave irradiation to provide a compound of the formula (Ia). Alternatively, a compound of the formula (4a) is reacted, according to Scheme 2, with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (Ia). Alternatively, a compound of the formula (4a) is reacted with an acid such as acetic acid, trifluoroacetic acid, hydrochloric acid, sulfuric acid, and the like, optionally in a solvent such as methylene chloride, tetrahydrofuran, 1,4-dioxane, ethanol, methanol, and the like, optionally with heating, optionally with microwave irradiation to provide a compound of the formula (Ia).

like, optionally with heating, optionally with microwave irradiation to provide a compound of the formula (Ia).

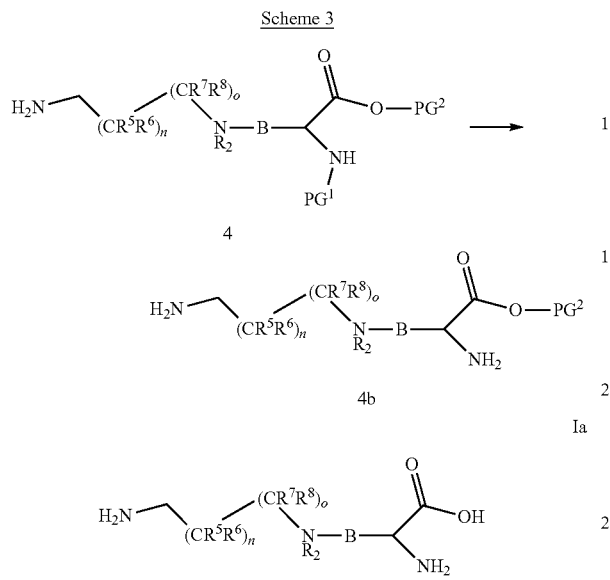

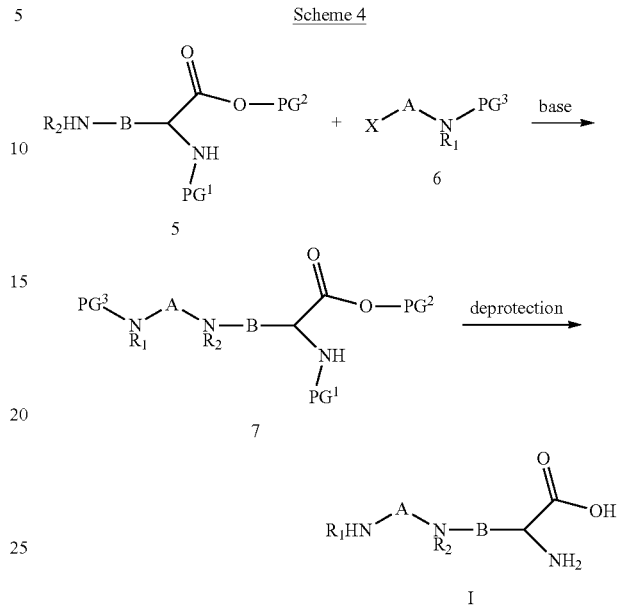

According to Scheme 3, a compound of the formula (4) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (4b). Alternatively, according to Scheme 3, a compound of the formula (4) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (4b).

According to Scheme 3, a compound of the formula (4b) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (Ia). Alternatively, according to Scheme 3, a compound of the formula (4b) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (I). Alternatively, according to Scheme 3, a compound of the formula (4b) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the According to Scheme 4, a compound of the formula (5), a known compound or a compound prepared by known means wherein $PG^1$ is a protecting group selected, for example, from the group consisting of triphenylmethyl (trityl), tert-butyloxycarbonyl (BOC), 9-fluorenylmethyloxycarbonyl (FMOC), and carbobenzyloxy (Cbz), and $PG^2$ is selected, for example, from the group consisting of 9-fluorenylmethyl (Fm), C1-6 alkyl and C3-7 branched alkyl, is reacted with a compound of the formula (6), a known compound or compound prepared by known methods wherein X is a leaving group such as bromine, chlorine, iodine, methanesulfonate, tolylsulfonate, and the like, and $PG^3$ is a protecting group selected from the group consisting of, for example, tert-butyloxycarbonyl (BOC), 9-fluorenylmethyloxycarbonyl (FMOC), and carbobenzyloxy (Cbz), in the presence of a base such as trimethylamine, diisopropylethylamine, pyridine, potassium carbonate, cesium carbonate, sodium hydroxide, potassium hydroxide, sodium hydride, potassium hydride, lithium diisopropylamide, sodium hexamethyldisilazide, lithium hexamethyldisilazide, potassium t-butoxide, sodium t-butoxide, and the like, in a solvent such as tetrahydrofuran, 1,4-dioxane, methylene chloride, methanol, ethanol, t-butanol, and the like, optionally with heating, optionally with microwave irradiation to provide a compound of the formula (7).

According to Scheme 4, a compound of the formula (7) is then reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (I). Alternatively a compound of the formula (7) is reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I).

Alternatively, according to Scheme 4, a compound of the formula (7) is then reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (I).

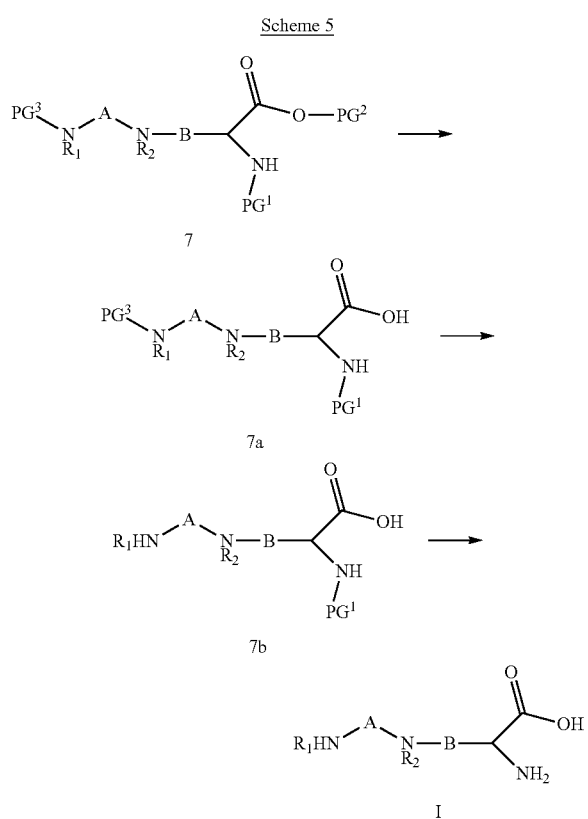

According to Scheme 5, a compound of the formula (7) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7a). Alternatively, a compound of the formula (7) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (7a).

According to Scheme 5, a compound of the formula (7a) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (7b).

Alternatively, a compound of the formula (7a) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (7b). Alternatively, a compound of the formula (7a) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7b). A compound of the formula (7b) is reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (7b) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (I). Alternatively, a compound of the formula (7b) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (I).

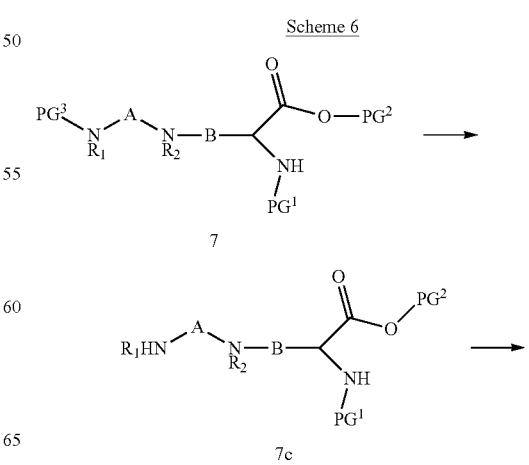

-continued

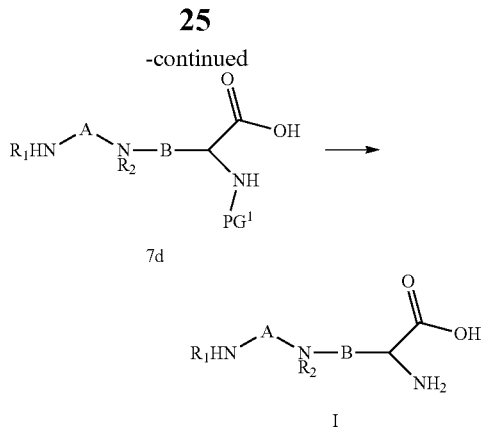

According to Scheme 6, a compound of the formula (7) is reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (7c). Alternatively, a compound of the formula (7) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (7c). Alternatively, a compound of the formula (7) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7c).

According to Scheme 6, a compound of the formula (7c) is then reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7d). Alternatively, a compound of the formula (7c) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (7d).

According to Scheme 6, a compound of the formula (7d) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (7d) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as, tetrahydrofuran, 1,4-dioxane, ethanol, methanol, and the like, optionally with heating, optionally with microwave irradiation to provide a compound of the formula (I). Alternatively, a compound of the formula (7d) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (I).

Scheme 7

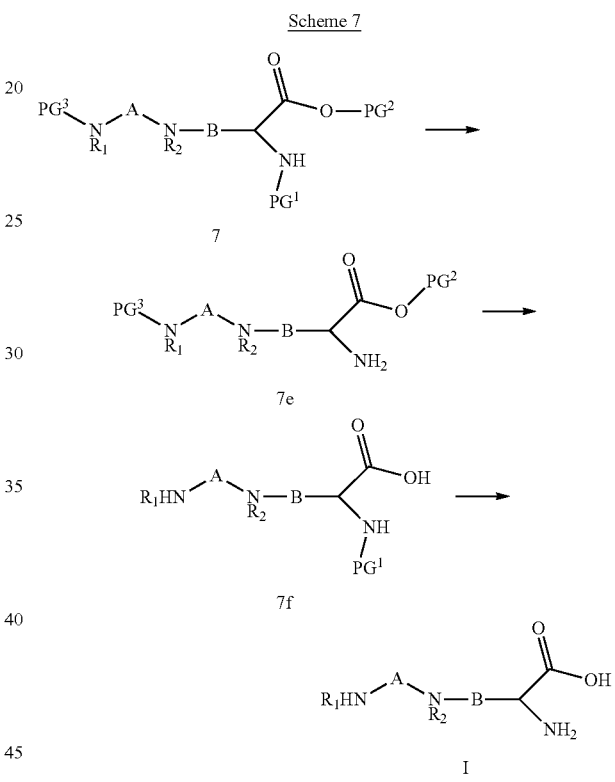

According to Scheme 7, a compound of the formula (7) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (7e). Alternatively, a compound of the formula (7) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (7e). Alternatively, a compound of the formula (7) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7e).

According to Scheme 7, a compound of the formula (7e) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7f). Alternatively, a compound of the formula (7e) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (7f).

According to Scheme 7, a compound of the formula (7f) is then reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (7f) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile)dichloropalladium[1,1'-bis(diphenylphosphino) ferrocene]dichloropalladium, and the like, in the presence of a solvent such as, tetrahydrofuran, 1,4-dioxane, ethanol, methanol, and the like, optionally with heating, optionally with microwave irradiation to provide a compound of the formula (I). Alternatively, a compound of the formula (7f) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (I).

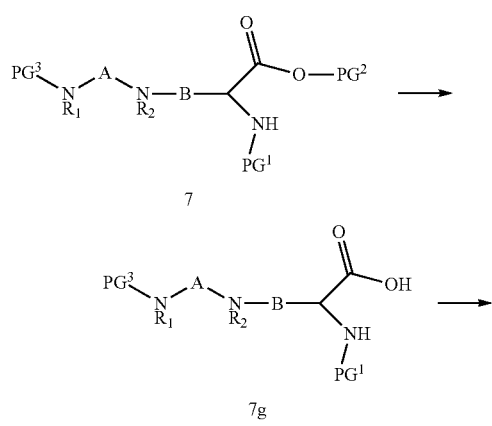

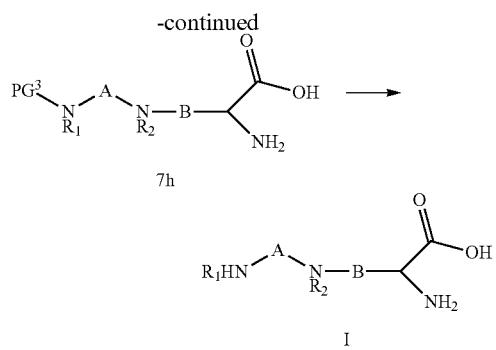

According to Scheme 8, a compound of the formula (7) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7g). Alternatively, a compound of the formula (7) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (7g).

According to Scheme 8, a compound of the formula (7g) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (7h). Alternatively, a compound of the formula (7g) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as, tetrahydrofuran, 1,4-dioxane, ethanol, methanol, and the like, optionally with heating, optionally with microwave irradiation to provide a compound of the formula (7h). Alternatively, a compound of the formula (7g) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (7h).

According to Scheme 8, a compound of the formula (7h) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (7h) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile)

dichloropalladium [1,1'-bis(diphenylphosphino) ferrocene] dichloropalladium, and the like, in the presence of a solvent such as, tetrahydrofuran, 1,4-dioxane, ethanol, methanol, and the like, optionally with heating, optionally with microwave irradiation to provide a compound of the formula (I). Alternatively, a compound of the formula (7h) is reacted with an acid such as acetic acid, trifluoroacetic acid, hydrochloric acid, sulfuric acid, and the like, optionally in a solvent such as methylene chloride, tetrahydrofuran, 1,4-dioxane, ethanol, methanol, and the like, optionally with heating, optionally with microwave irradiation to provide a compound of the formula (I).

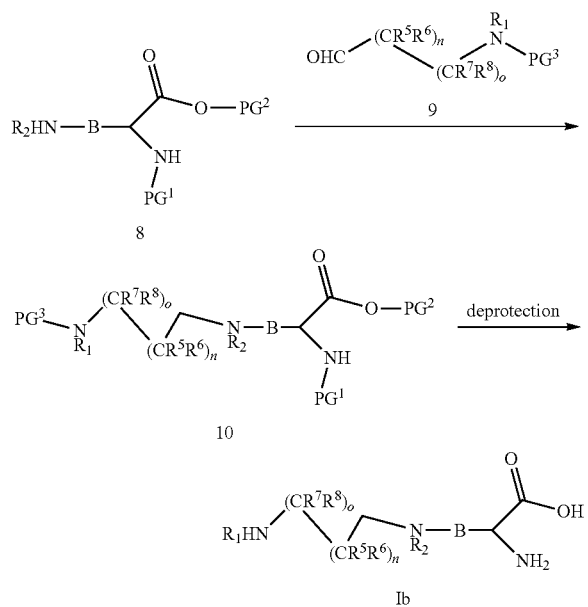

Scheme 9

According to Scheme 9, a compound of the formula (9), a known compound or a compound prepared by known means wherein $PG^1$ is a protecting group selected from the group consisting of, for example, triphenylmethyl (trityl), tert-butyloxycarbonyl (BOC), 9-fluorenylmethyloxycarbonyl (FMOC), and carbobenzyloxy (Cbz) and $PG^2$ is selected from the group consisting of, for example, 9-fluorenylmethyl (Fm), C1-6 alkyl and C3-7 branched alkyl, is reacted with a compound of the formula (9), a known compound or a compound prepared by known methods wherein $PG^3$ is a protecting group selected from the group consisting of, for example, triphenylmethyl (trityl), tert-butyloxycarbonyl (BOC), 9-fluorenylmethyloxycarbonyl (FMOC), and carbobenzyloxy (Cbz), in the presence of a reducing agent such as sodium borohydride, lithium borohydride, sodium borohydride, sodium cyanoborohydride, sodium triacetoxy borohydride, lithium triacetoxy borohydride, and the like, optionally in the presence an acid such as acetic acid, formic acid, trifluoroacetic acid, hydrochloric acid, and the like, optionally in the presence of a Lewis acid such as boron trifluoride, aluminum trichloride, titanium tetrachloride, tin chloride, and the like, in the presence of a solvent such as methanol, ethanol, isopropanol, tetrahydrofuran, 1,4-dioxane, methylene chloride, and the like, optionally with heating, optionally with microwave irradiation to provide a compound of the formula (10).

According to Scheme 9, a compound of the formula (8) is then reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (10) is reacted with a base such as lithium hydroxide, sodium hydroxide, sodium carbonate, lithium carbonate, piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (10) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (Ib).

Scheme 10

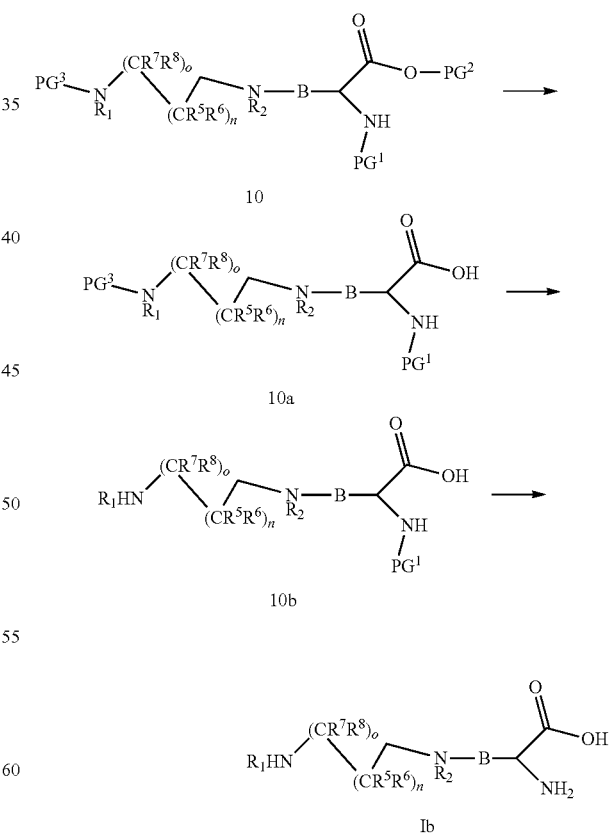

According to Scheme 10, a compound of the formula (10) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10a). Alternatively, a compound of the formula (10) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (10a).

According to Scheme 10, a compound of the formula (10a) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (10b). Alternatively, a compound of the formula (10a) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (10b). Alternatively, a compound of the formula (10a) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10b).

According to Scheme 10, a compound of the formula (10b) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (I). Alternatively, a compound of the formula (10b) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (Ib). Alternatively, a compound of the formula (10b) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (Ib).

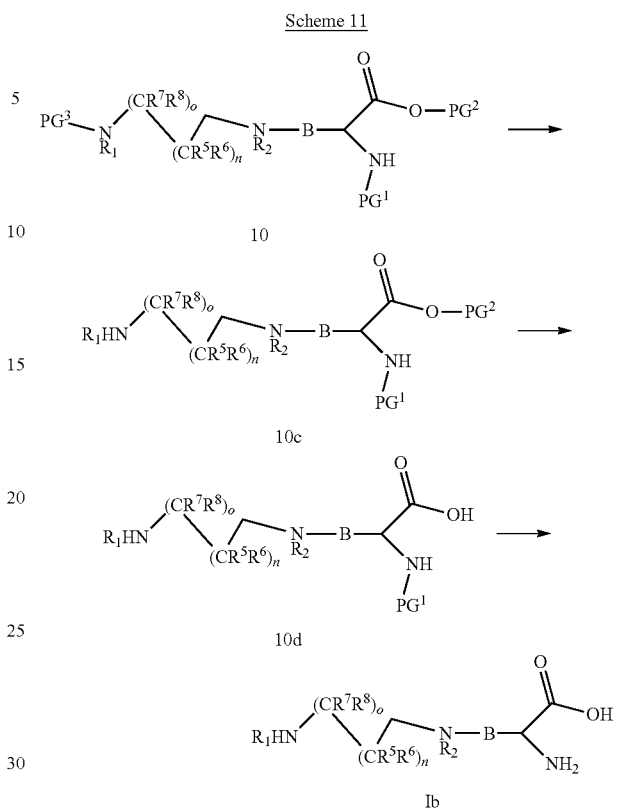

According to Scheme 11, a compound of the formula (10) is reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (10c). Alternatively, a compound of the formula (10) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (10c). Alternatively, a compound of the formula (10) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10c).

According to Scheme 11, a compound of the formula (10c) is then reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10d). Alternatively, a compound of the formula (10c) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (10d).

A compound of the formula (10d) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (Ib). Alternatively, a compound of the formula (10d) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (Ib). Alternatively, a compound of the formula (10d) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (Ib).

Scheme 12

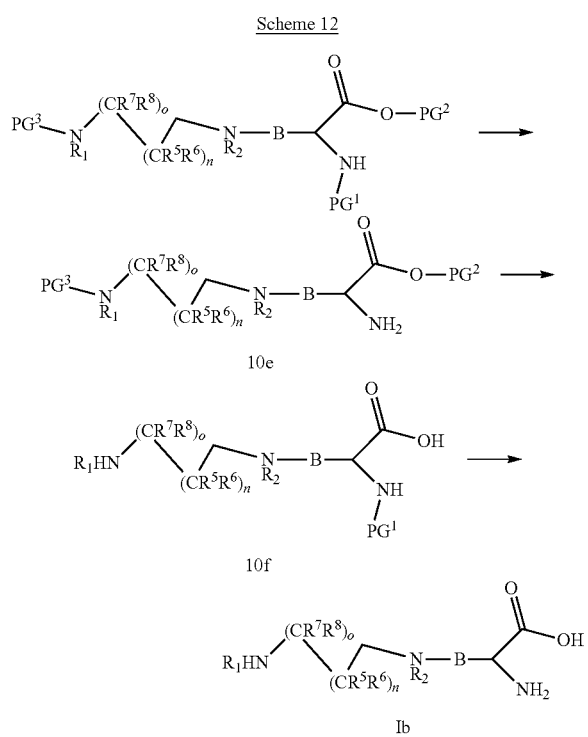

According to Scheme 12, a compound of the formula (10) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (10e). Alternatively, a compound of the formula (10) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene]dichloropalladium, and the like, in the presence of a solvent such as tetrahydrofuran, 1,4-dioxane, ethanol, methanol, and the like, optionally with heating, optionally with microwave irradiation to provide a compound of the formula (10e). Alternatively, a compound of the formula (10) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10e).

According to Scheme 12, a compound of the formula (10e) is then reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10f). Alternatively, a compound of the formula (10e) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (10f).

According to Scheme 12, a compound of the formula (10f) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (Ib). Alternatively, a compound of the formula (10f) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (Ib). Alternatively, a compound of the formula (10f) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (Ib).

Scheme 13

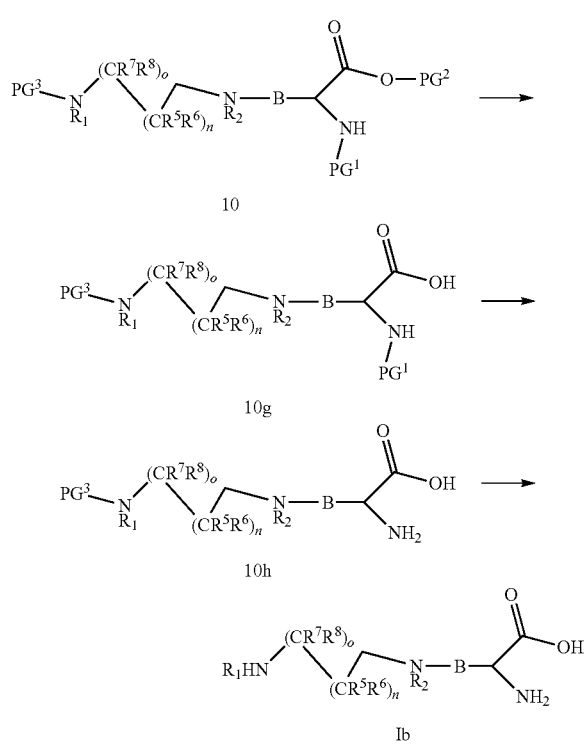

According to Scheme 13, a compound of the formula (10) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10g). Alternatively, a compound of the formula (10) is reacted with a base such as lithium hydroxide, sodium hydroxide, sodium carbonate, lithium carbonate, and the like in a solvent such as methylene chloride, tetrahydrofuran, 1,4-dioxane, ethanol, methanol, and the like, optionally with heating, optionally with microwave irradiation to provide a compound of the formula (10g).

According to Scheme 13, a compound of the formula (10g) is then reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (10h). Alternatively, a compound of the formula (10g) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (10h). Alternatively, a compound of the formula (10g) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (10h).

According to Scheme 13, a compound of the formula (10h) is then reacted with a base such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (Ib). Alternatively, a compound of the formula (10h) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (Ib). Alternatively, a compound of the formula (10h) is reacted with an acid such as acetic acid, trifluoroacetic acid, hydrochloric acid, sulfuric acid, and the like, optionally in a solvent such as methylene chloride, tetrahydrofuran, 1,4-dioxane, ethanol, methanol, and the like, optionally with heating, optionally with microwave irradiation to provide a compound of the formula (Ib).

Scheme 14

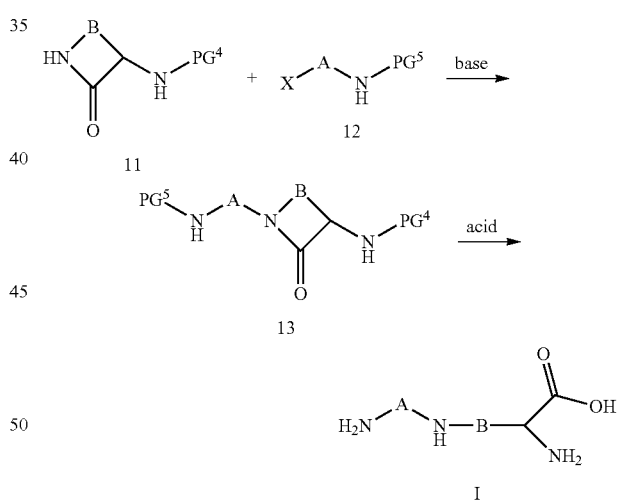

According to Scheme 14, a compound of the formula (11), a known compound or a compound prepared by known methods wherein $PG^4$ is a protecting group selected from the group consisting of, for example, triphenylmethyl (trityl), tert-butyloxycarbonyl (BOC), 9-fluorenylmethyloxycarbonyl (FMOC), and carbobenzyloxy (Cbz) is reacted with a compound of the formula (12), a known compound or a compound prepared by known methods wherein X is a leaving group such as bromine, chlorine, iodine, methanesulfonate, tolylsulfonate, and the like and $PG^5$ is a protecting group selected from the group consisting of, for example, triphenylmethyl (trityl), tert-butyloxycarbonyl (BOC), 9-fluorenylmethyloxycarbonyl (FMOC), and carbobenzyloxy (Cbz) in the presence of a base such as sodium hydride, potassium hydride, lithium diisopropylamide, sodium hexamethyldisilazide, lithium hexamethyldisilazide, potassium t-butoxide, sodium t-butoxide and the like, in a solvent such as tetrahydrofuran, 1,4-dioxane, methylene chloride, methanol, ethanol, t-butanol, and the like, optionally with heating, optionally with microwave irradiation to provide a compound of the formula (13).

According to Scheme 14, a compound of the formula (13) is then reacted with an acid such as hydrochloric acid, sulfuric acid, phosphoric acid and the like, optionally in the presence of water, optionally with heating, optionally with microwave irradiation to provide a compound of formula I.

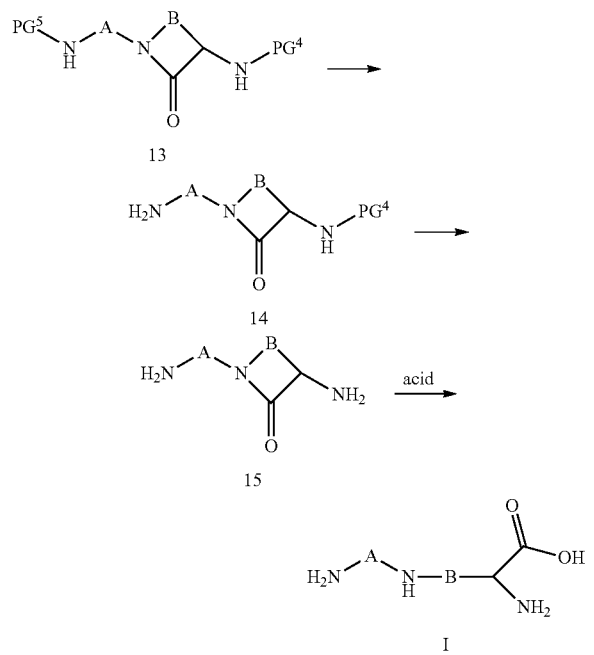

According to Scheme 15, compound of the formula (13) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (14). Alternatively, a compound of the formula (13) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (14). Alternatively, a compound of the formula (13) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (14).

According to Scheme 15, a compound of the formula (14) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (15). Alternatively, a compound of the formula (14) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (15). Alternatively, a compound of the formula (14) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (15).

According to Scheme 15, a compound of the formula (15) is then reacted with an acid such as hydrochloric acid, sulfuric acid, phosphoric acid and the like, optionally in the presence of water, optionally with heating, optionally with microwave irradiation to provide a compound of formula I.

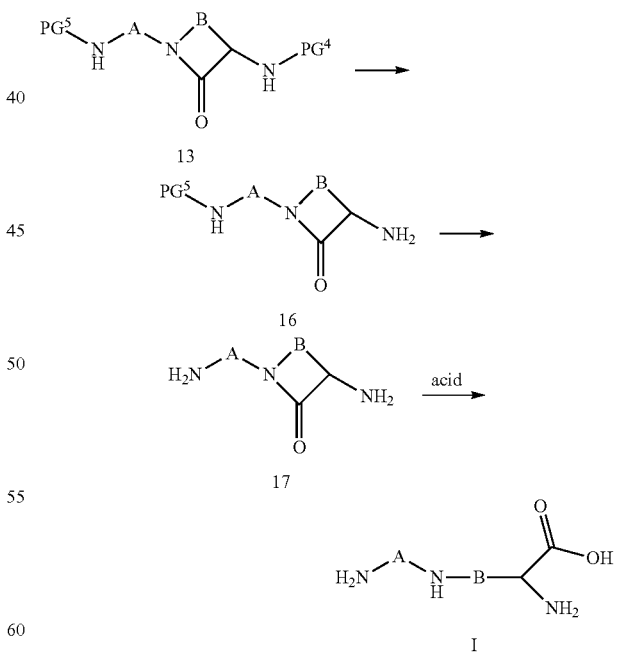

According to Scheme 16, a compound of the formula (13) is reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (16). Alternatively, a compound of the formula (13) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (16). Alternatively, a compound of the formula (13) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (16).

According to Scheme 16, a compound of the formula (16) is then reacted with abase such as piperidine, pyridine, 2,6-lutidine, and the like, in a solvent such as methylene chloride, tetrahydrofuran, 1,4-dioxane, ethanol, methanol, and the like, optionally with heating, optionally with microwave irradiation to provide a compound of the formula (17). Alternatively, a compound of the formula (16) is reacted with hydrogen in the presence of a catalyst such as palladium on carbon, palladium on barium sulfate, palladium on celite, palladium on calcium carbonate, palladium on barium carbonate, palladium on silica, palladium on alumina, palladium acetate, palladium bis(triphenylphosphine) dichloride, palladium tetrakis(triphenylphospine), bis(acetonitrile) dichloropalladium [1,1'-bis(diphenylphosphino) ferrocene] dichloropalladium, and the like, in the presence of a solvent such as tetrahydrofuran, 1,4-dioxane, ethanol, methanol, and the like, optionally with heating, optionally with microwave irradiation to provide a compound of the formula (17). Alternatively, a compound of the formula (16) is reacted with an acid such as acetic acid, trifluoroacetic acid, hydrochloric acid, sulfuric acid, trifluoromethanesulfonic acid and the like, optionally in a solvent such as methylene chloride, tetrahydrofuran, 1,4-dioxane, ethanol, methanol, and the like, optionally with heating, optionally with microwave irradiation to provide a compound of the formula (17).

According to Scheme 16, a compound of the formula (17) is then reacted with an acid such as hydrochloric acid, sulfuric acid, phosphoric acid and the like, optionally in the presence of water, optionally with heating, optionally with microwave irradiation to provide a compound of formula (I).

In the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected". Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts, John Wiley & Sons Ltd., the entire disclosure of which is incorporated herein by reference.

It will be appreciated by one skilled in the art that the processes described are not the exclusive means by which compounds of Formula I may be synthesized and that a repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, $2^{nd}$ Edition, 2004), *Comprehensive Heterocyclic Chemistry*, Ed. A. R. Katritzky and C. W. Rees (Pergamon Press, 1984), and *Comprehensive Heterocyclic Chemistry II*, Ed. A. R. Katritzky, C. W. Rees, and E. F. V. Scriven (Pergamon Press, 1996).

The compounds of Formula I and intermediates may be isolated from their reaction mixtures and purified by standard techniques such as filtration, liquid-liquid extraction, solid phase extraction, distillation, recrystallization or chromatography.

It will be understood that when compounds of Formula I the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention which are biologically active in the treatment of insulin resistance.

A chiral center occurs in the α-carbon of the α-amino acid functionality of the compounds of Formula I. The compounds of Formula I are characterized by the (S) absolute configuration about the α-carbon of the contained α-amino acid functionality, according to the Cahn-Ingold-Prelog rules,

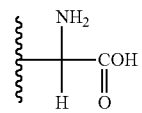

as exampled by the compound (S)-2-amino-6-((3-aminopropyl)amino)hexanoic acid, a compound of Formula I

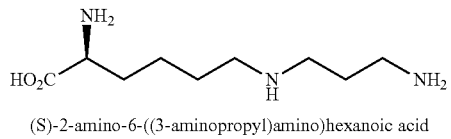 [SMILES: NCCCNCCCC[C@H](N)C(=O)O]

(S)-2-amino-6-((3-aminopropyl)amino)hexanoic acid

According to certain embodiments, a compound of Formula I is an isolated (S) optical isomer with respect to the configuration about the α-carbon of the contained α-amino acid functionality. By an "isolated optical isomer" means a compound which has been substantially purified from the corresponding optical isomer(s) of the same formula. Preferably, the isolated isomer is at least about 80%, more preferably at least 85% pure, more preferably at least 90% pure, more preferably at least 95% pure, even more preferably at least 98% pure, most preferably at least about 99% pure, by weight, the balance being made up of the corresponding (R) enantiomer. In some embodiments, the isolated (S) enantiomer is free of the corresponding (R) enantiomer, except for trance amounts of the (R) enantiomer.

Salts

The compounds of Formula I may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, pivalic, propionic, furoic, mucic, isethionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, camphorsulfonic, and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, tromethamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* by P. H. Stahl and C. G. Wermuth (Wiley-VCH 2002).

Pharmaceutical Compositions and Therapeutic Administration

A pharmaceutical composition comprises a pharmaceutically acceptable carrier and a compound, or a pharmaceutically acceptable salt thereof, according to Formula I.

The compounds may be administered in the form of a pharmaceutical composition, in combination with a pharmaceutically acceptable carrier. The active ingredient or agent in such formulations (i.e. a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorobutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The compounds of Formula I may be administered in a convenient manner. Suitable topical routes include oral, rectal, inhaled (including nasal), topical (including buccal and sublingual), transdermal and vaginal, preferably across the epidermis. The compound of Formula I can also be used for parenteral administration (including subcutaneous, intravenous, intramuscular, intradermal, intraarterial, intrathecal and epidural), and the like. It will be appreciated that the preferred route may vary with for example the condition of the recipient.

A physician will determine the dosage of the active agent which will be most suitable and it will vary with the form of administration and the particular compound chosen, and furthermore, it will vary depending upon various factors, including but not limited to the patient under treatment and the age of the patient, the severity of the condition being treated, the rout of administration, and the like. A physician will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 1000 mg, more typically from about 1 to about 500 mg, more typically, from about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The treatment may be carried out for as long a period as necessary, either in a single, uninterrupted session, or in discrete sessions. The treating physician will know how to increase, decrease, or interrupt treatment based on patient response. The treatment schedule may be repeated as required. According to one embodiment, compound of Formula I is administered once daily.

Treatment efficacy is generally determined by improvement in insulin resistance, i.e., an increase in insulin sensitivity. Insulin resistance may be assessed before, during and after treatment by use of the homeostasis model assessment of insulin resistance (HOMA-IR) index. The HOMA-IR value is calculated as level of fasting glucose (millimoles/liter) times the level of fasting insulin (microunits/milliliter) divided by 22.5. The value of 3.0 identifies the highest quartile among populations without diabetes (Ascaso et al., Diabetes Care, 2003, 26: 3320).

Treatment efficacy may also be assessed by the A1C test, which indicates the average of an individual's blood glucose level over the prior 3 months. See, Nathan, Diabetes Care, 32(12):e160 (2009).

The practice of the disclosed subject matter is illustrated by the following non-limiting examples.

EXAMPLES

Example 1

The following study demonstrates a direct link between function impairment due to GLUT4 carbonylation and insulin resistance. A GLUT4-SNAP fusion construct was generated. 3T3-L1 adipocytes were then retrovirally transduced with the construct to overexpress the GLUT4-SNAP protein. Twenty-four hours after the transduction, the cells were treated with and without 20 µM of 4-HNE for an additional 4 hours. This 4-HNE dose was chosen because it was similar to the physiological levels and was non-toxic. In order to identify and quantitate GLUT4 carbonylation (K264 NHE-adduct or R265 and R246 glutamic semialdehyde adducts), a mass spectroscopy-based multiple reaction monitoring (MRM) method was developed and validated. This high throughput method does not require antibodies, is robust and is sensitive at sub-picomole levels.

The results are shown in FIG. 1A-1B, indicating that 4-HNE, 20 µM for 4 hour induced the formation of the K264-HNE adduct in 3T3-L1 cells overexpressing GLUT4. The MRM data presented in FIG. 1A shows an increase in the transition of HNE-induced K264-HNE adducts. The data was then used to calculate the amounts of carbonylated GLUT4 presented in FIG. 1B. Fourier transition of the GLUT4 peptide found in humans were used for quantitation.

Example 2

The following study demonstrates the effect on of 4-HNE and $H_2O_2$ on glucose transport. 3T3-L1 adipocytes ($1 \times 10^6$) were treated with either 500 µM of 4-HNE or $H_2O_2$ or combination of both for 4 hour and were then stimulated with 100 nM insulin for 60 minutes. The glucose uptake was measured by a specific MRM method. The data, presented in FIG. 2, shows that glucose uptake by 3T3-L1 adipocytes was reduced by 32% and 66% with 4-HNE and $H_2O_2$ treatment, respectively.

Example 3

The following study demonstrates that GLUT4 carbonylation (adduction by 4HNE) is present in the fat tissue of insulin resistant, pre-diabetic and diabetic human individuals.

A. Fat Tissue Sample Preparation

Proteins were extracted from the fat tissue (~200 mg) using a Mem-PER Plus Membrane Protein Extraction Kit (Thermo Scientific #89842) and 1× protease inhibitor (Pierce Halt Protease Inhibitor Cocktail 100×). Tissue was incubated on ice for 10 min, then the homogenized for 2 min at 1000 rpm and proteins were separated by centrifugation at 10,000 g for 15 min.

B. Digestion

Thirty microliters of each of the samples were denatured with 10 µl of DL-dithiothreitol (5 mg/ml) at 37° C. for 20 min and alkylated with 10 µL of iodoacetamide (12.5 mg/ml) at 37° C. for 20 min. Samples were diluted with 25 mM $NH_4HCO_3$ (450 µl) and 10 µL of trypsin was added for protein digestion. Formic acid 1% final concentration was used to stop the digestion and ionize the peptides.

C. STAGE TIPS Treatment

Digested peptides were desalted and cleaned up by STAGE TIPS (Thermo Scientific, West Palm Beach, Fla.) using chromatographic C18 beads for immobilization. In brief, a solid phase C18 column was activated with acetonitrile 100% and equilibrated on buffer A (water-0.1% formic acid) the samples were passed two times through the tips, samples were desalted by washing twice with buffer A and eluted with 50 µL of elution buffer (85% acetonitrile, 0.1% formic acid) and 50 µL of acetonitrile. Samples were dried in speed vacuum for 30 minutes and resuspended in the MRM analysis with 50 µl of 85% acetonitrile, 15% formic acid 0.1% and 115 µL of buffer A.

D. Multiple Reaction Monitoring (MRM)

MRM-MS is a quantitative mass spectrometry-based target technology that generates unique fragment ions associated with their corresponding precursor ions. These ions can be detected and quantified in complex matrix samples. The quantitation of peptides is obtained measuring the intensity of the fragment ions. To detect carbonylated GLUT4, specific peptides were selected. The parent ion for the carbonylated GLUT4 sequence LTGWADVSGVLAELKDEK-4HNE (SEQ ID NO:2) with triple charge mass is 696.381 m/z. After fragmentation of the parent ion, relative daughter ions: 1101.94, 788.4758, 917.5138, 988.5555, 722.4186, and 481.9482 m/z were identified and used for the quantification of the carbonylated Glut 4 peptide. Also, MRM methods for the GLUT4 unmodified sequence of the same peptide were also developed. Relative carbonylated GLUT4 was estimated as a percentage of the carbonylated peptide respect to the total of all GLUT4 peptide signal. An independent peptide from the heat shock 70 kDa protein A/1B (a protein not related to GLUT4) was selected as an internal standard. This internal standard peptide allows a relative quantification because it is used for normalization of the intensity of each GLUT4 peptide within the same sample.

MRM analyses were performed with a DIONEX Ulti-Mate™ 3000 SRLCnano HPLC system (Thermo Scientific) coupled to a TSQ QUANTUM™ ULTRA (Thermo Scientific) triple quadrupole. PINPOINT™ software was used for method development and the optimization of the mass spectrometer parameters, as well as for peptide quantification. Peptides were separated by liquid chromatography, 5 µL of samples were injected in the nanoHPLC system and separation was carried out on a C18 column (ACCLAIM PepMap® RSLC, Thermo Scientific). Elution was performed with a gradient of at a flow rate of 0.300 µl/min with buffer A (0.1% (v/v) formic acid) and Buffer B (acetonitrile containing 0.1% (v/v) formic acid). A linear gradient was performed from 5% B to 30% B in 22.5 min followed by the washing step with 90% B for 7 min and the column re-equilibration for 14 min, with a 50 min long total cycle. The mass spectroscopy analysis was carried out in a positive ionization mode, using an ion spray voltage of 2,000V and a temperature of 200 C. Nebulizer and gas flow was set at 30 psi.

The aforementioned MRM protocol was utilized to compare GLUT4 modifications in fat samples from the following groups: (i) lean insulin resistant; (ii) lean insulin resistant on overnutrition; (iii) obese non-diabetic; (iv) obese pre-diabetic and (v) obese diabetic. Comparing the adipose tissue of lean and lean-on-overnutrition insulin resistant individuals revealed that the levels of GLUT4-K264-NHE-adduct were increased by at-least 2.5 folds in subjects that were lean but insulin resistant and on a hypercaloric diet (FIG. 3A). Comparing the adipose tissue GLUT4 K264 NHE-adduct level in obese non-diabetic, obese pre-diabetic, and obese diabetic subjects revealed that the GLUT4 carbonylation was increased in the pre-diabetic and diabetic individuals (FIG. 3B).

To determine the percentage of GLUT4 that is carbonylated in the 5 study groups, an MRM method was employed to detect total GLUT4. The results in FIG. 3C show that increased levels of GLUT4 carbonylations occur in subjects that are insulin resistant, i.e., pre-diabetic and diabetic. About 50% GLUT4 carbonylation is identical to the reported 50% decrease in insulin-stimulated glucose uptake (GIR) after 7 days of overnutrition.

Figure 3D:
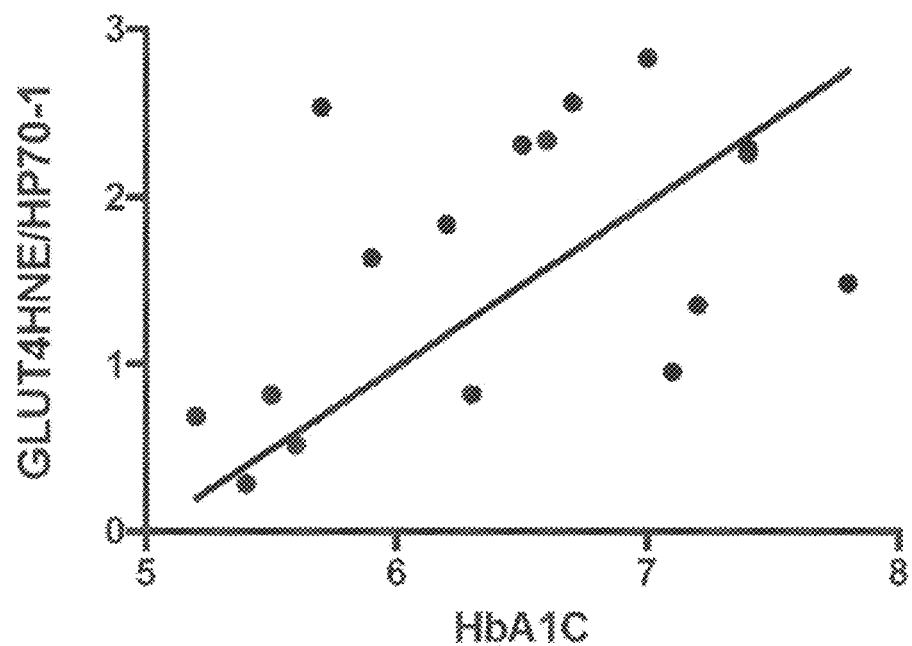
FIG. 3D is a graph of GLUT4 carbonylation as determined by detection of the adducted GLUT4 fragment LTGWADVSGVLAELKDEK-4HNE (SEQ ID NO:2) versus the level of the insulin resistance marker HOMA-IR.

The results in FIG. 3D confirm that the GLUT4 carbonylations linearly increase with the insulin resistance marker HbA1C (glycated haemoglobin) marker for insulin resistance.

Example 4

(S)-2-amino-6-((3-aminopropyl)amino)hexanoic Acid Dihydrochloride

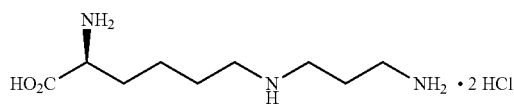

(S)-2-amino-6-((3-aminopropyl)amino)hexanoic acid was prepared as follows.

A. Preparation of tert-butyl-(S)-(2-oxoazepan-3-yl)carbamate

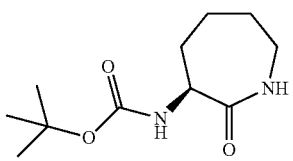 [SMILES: CC(C)(C)OC(=O)N[C@H]1CCCCNC1=O]

Di-tert-butyl-dicarbonate (733 μL, 3.189 mmol) was added to a suspension of L-(−)-α-amino-ε-caprolactam hydrochloride (500 mg, 3.037 mmol) and triethylamine (847 μL, 6.074 mmol) in anhydrous tetrahydrofuran (4 mL). The resulting suspension was stirred at room temperature overnight and concentrated down. The residual white solid was partitioned between ethyl acetate and water. The aqueous layer was removed. The organic layer was washed twice with 1N aqueous hydrochloric acid, twice with saturated aqueous sodium bicarbonate, once with brine, dried over anhydrous sodium sulfate and concentrated. Pure titled compound was obtained as a white solid. $^1$H NMR (400 MHz, CD$_3$OD) δ 6.45 (bd, J=5.8 Hz, 1H), 4.18-4.30 (m, 1H), 3.17-3.30 (m, 2H), 1.70-2.03 (m, 4H), 1.48-1.57 (m, 1H), 1.45 (s, 9H), 1.28-1.42 (m, 1H); MS (ESI): m/z 250.8 (M+Na)$^+$.

B. Preparation of tert-butyl-(S)-(1-(3-((tert-butoxycarbonyl)amino)propyl)-2-oxoazepan-3-yl)carbamate

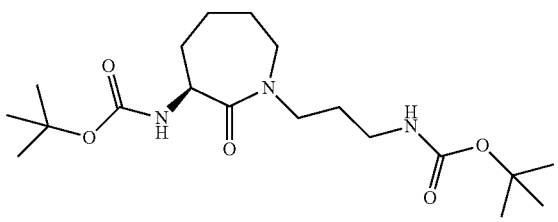 [SMILES: CC(C)(C)OC(=O)NCCCN1CCCC[C@H](NC(=O)OC(C)(C)C)C1=O]

Sodium bis(trimethylsilyl)amide (2.524 mmol; 2.5 mL of a 1.0 M solution in tetrahydrofuran) was added to a solution of tert-butyl (S)-(2-oxoazepan-3-yl)carbamate (288 mg, 1.262 mmol) in anhydrous tetrahydrofuran (12 mL).

The resulting suspension was stirred at room temperature for thirty minutes. 3-(Boc-amino)propyl bromide (2.524 mmol; 470 μl) was added all at once and the reaction was stirred at room temperature for 28 hours.

The reaction mixture was concentrated on a rotary evaporator and the residue was partitioned between ethyl acetate and water. The aqueous layer was removed. The organic layer was washed with brine, dried over anhydrous sodium sulfate and concentrated. The crude product was purified by column chromatography on silica gel using a gradient solvent system of 0 to 100% of ethyl acetate in hexanes to afford the titled compound as a colorless oil. $^1$H NMR (400 MHz, CDCl$_3$) δ 5.96 (bd, J=5.0 Hz, 1H), 5.32 (bs, 1H), 4.36 (m, 1H), 3.45-3.62 (m, 2H), 3.33-3.41 (m, 1H), 3.08-3.22 (m, 2H), 2.97-3.06 (m, 1H), 2.02-2.09 (m, 1H), 1.92-2.00 (m, 1H), 1.76-1.87 (m, 2H), 1.61-1.70 (m, 2H), 1.40-1.50 (m, 19H), 1.31-1.38 (m, 1H); MS (ESI): m/z 407.8 (M+Na)$^+$.

C. Preparation of (S)-2-Amino-6-((3-aminopropyl)amino)hexanoic Acid Dihydrochloride

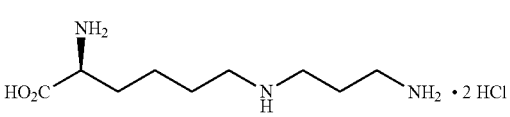

Tert-butyl-(S)-(1-(3-((tert-butoxycarbonyl)amino)propyl)-2-oxoazepan-3-yl)carbamate (100 mg, 0.2596 mmol) was dissolved in 12 N aqueous hydrochloric acid (4 mL). The resulting solution was stirred at room temperature until all of the bubbling had ceased. It was transferred to a microwave reaction vial and heated at 160° C. for ninety minutes. Upon concentration, pure titled compound was afforded as a light yellowish tan solid. $^1$H NMR (400 MHz, D$_2$O) δ 4.00 (t, J=6.3 Hz, 1H), 3.08-3.20 (m, 6H), 1.90-2.15 (m, 4H), 1.72-1.83 (m, 2H), 1.43-1.62 (m, 2H); MS (ESI): m/z 203.9 (M+H)$^+$.

Example 5

(S)-2-amino-6-((3-aminopropyl)amino)hexanoic Acid Dihydrochloride In Vitro and Stability Study The following studies demonstrate the solubility and solution stability of (S)-2-amino-6-((3-aminopropyl)amino) hexanoic acid dihydrochloride.

A. Solubility

The title compound was determined to be soluble in water or DMSO at a concentration of at least 10 mM. In phosphate buffered saline (PBS) solubility assay (PBS: 136.9 mM NaCl, 2.68 mM KCl, 8.1 mM Na$_2$HPO$_4$; 1.47 mM KH$_2$PO$_4$; +/−0.9 mM CaCl$_2$; +/−0.49 mM MgCl$_2$; pH 7.4), without Ca or Mg (Ca/Mg interfere with the assay), the title compound had a solubility >200 μM (maximum concentration tested in a standard protocol).

B. Liver Microsome Stability

The stability of the title compound in the presence of liver microsomes was tested at 1 μM compound and 0.5 mg/ml rat or human microsomal protein, at 37° C. with 2 mM NADPH (standard in vitro screening concentrations). The results are as follows: (a) Rat (pooled Sprague Dawley; male): t$_{1/2}$>60 min; Clint <23 μL/min/mg protein; (b) Human (pooled male and female): $t_{1/2}$>60 min; Clint <23 µL/min/mg protein. The "$t_{1/2}$" values are the maximum time employed for the respective assays. No significant loss of this compound was seen at any time point in these assays.

C. Solution Stability

The stability of the title compound was tested in the following media, in the following concentrations: (i) 1 µM in mouse (male C57BL/6) plasma, (ii) 1 µM in PBS (with Ca and Mg) (control treatment); (iii) 5 µM in stimulated gastric fluid (SGF; 0.2% NaCl; 84 mM HCl; 0.32% pepsin; pH 1.2); (iv) 5 µM in stimulated intestinal fluid (SIF; 50 mM KP, pH 6.8; 10 mg/ml pancreatin); and (v) 5 µM in PBS (+Ca and Mg) (control treatment). The results are as follows: (i) 1 µM in mouse plasma, $t_{1/2}$>6 hr at 37° C.; (ii) 1 µM in PBS, $t_{1/2}$>6 hr at 37° C.; (iii) 5 µM in SGF, $t_{1/2}$>3 hrs at 37° C.; (iv) 5 µM in SIF, $t_{1/2}$>3 hrs at 37° C.; and (v) 5 µM in PBS, $t_{1/2}$>3 hr at 37° C. The "$t_{1/2}$" values are the maximum time employed for the respective assays. No significant loss of this compound was seen at any time point in these assays.

Example 6

(S)-2-amino-6-((3-aminopropyl)amino)hexanoic Acid Dihydrochloride Intravenous and Oral Pharmacokinetic Studies The following studies demonstrate the intravenous and oral pharmacokinetic behavior of (S)-2-amino-6-((3-aminopropyl)amino)hexanoic acid dihydrochloride.

A. Methods

A pharmacokinetic study was conducted with mice (Charles river) (N=3). The animals had free access to water and standard laboratory chow under a controlled 12 hour light-dark cycle. After at least one week of an acclimation period, the mice were administrated a dose of 5 mg/kg of the title compound ((S))-2-amino-6-((3-aminopropyl)amino) hexanoic acid dihydrochloride) intravenously or 10 mg/kg orally. For both intravenous and oral administration, the compound was dissolved in saline. After intravenous administration, blood samples were collected at 10 min, 30 min, 1, 2, 4, 8 and 24 hours. For oral gavage, blood samples were collected at 15 min, 30 min 1, 2, 4, 8 and 24 hours. The blood samples were collected in polythene tubes with heparin sodium 100 unit/mL and centrifuged at 6000×g for 10 min to obtain plasma, which was stored at −20° C. until analysis.

The title compound concentration in mouse plasma was quantitated using an LC/MS/MS (API 4000, AB SCIEX). Briefly, 50 µl mouse plasma was added to 100 µl acetonitrile with internal standard (Diltiazem 10 ng/ml). The mixture was vortexed and centrifuged, and 5 µl supernatant was injected into LC/MS/MS for analysis. The separation was performed on a Waters C18 column (2.1×50 mm, 3.5 µM particle size). The mobile phase consisted of 0.2% pentafluoropropionic acid in water:acetonitrile by gradient elution. A Sciex API 4000 mass spectroscopy system equipped with an electrospray source in the positive-ion multiple reaction monitoring (MRM) mode was used for detection. The MRM transitions monitored for the title compound and diltiazem were m/z 204.4/84.2 and m/z 415/178, respectively. The retention time is 12.5 min for (S)-2-amino-6-((3-aminopropyl)amino)hexanoic acid and 14 min for diltiazem. The quantitation ranged from 25 to 1000 ng/ml.

B. Results—Intravenous Pharmacokinetics

Intravenous pharmacokinetics data for ((S))-2-amino-6-((3-aminopropyl)amino)hexanoic acid are summarized in Table 1. The title compound has a volume of distribution (Vss) of 0.414 L/Kg and a half life ($T_{1/2}$) of 2.53 hrs.

TABLE 1

| | | | | | | | | |
|---|---|---|---|---|---|---|---|---|
| | | | | In vivo pharmacokinetic properties | | | | |
| Route | Dose (mg/ml) | Cmax (µg/mL) | Tmax (hr) | $AUC_{tot}$ (µg*hr/m) | $T_{1/2}$ (hr) | CL (L/hr) | $V_{SS}$ (L/kg) | F % |
| IV | 5 | 8.36 | | 4.72 | 2.53 | 0.31 | 0.414 | |
| PO | 10 | 1.44 | 3.33 | 10.45 | 3.25 | 0.285 | 2.12 | 100 |

C. Results—Oral Pharmacokinetics

Oral pharmacokinetic data for ((S))-2-amino-6-((3-aminopropyl)amino)hexanoic acid are summarized in Table 1. Upon oral dosing, bioavailability (F) of the title compound was approximately 100%. Clearance (CL) and half-life were similar to the intravenous study but Vss was higher (2.1 L/Kg vs. 0.4 L/Kg).

D. Projected Dose for Oral Dosing in Drinking Water

Figure 4:
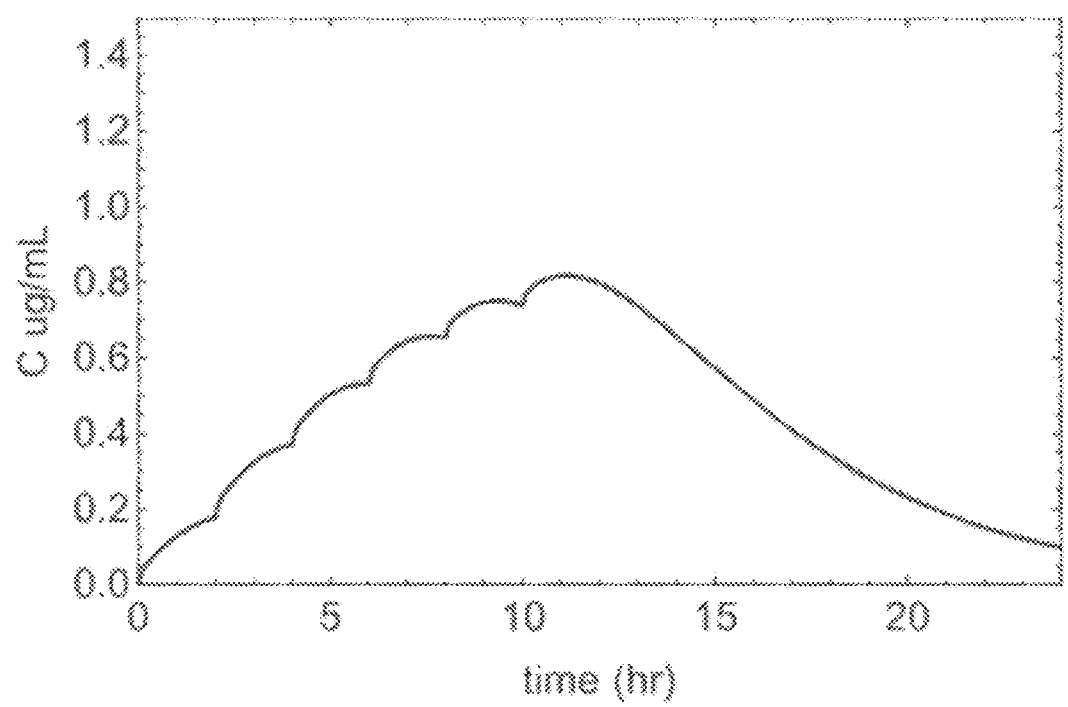
FIG. 4 shows the predicted concentration-time profile of (S)-2-amino-6-((3-aminopropyl)amino)hexanoic acid dihydrochloride in plasma following oral administration of 10 mg/kg/day, modeled as six oral doses over 12 hours.

The predicted C-t profile for 10 mg/kg, day in drinking water (modeled as six oral doses over 12 hrs) is shown in FIG. 4. The maximum predicted concentration is 0.82 µg/mL and the minimum concentration 0.1 µg/mL. The dose can be adjusted proportionally to achieve the desired concentrations.

Example 7

(S)-2-amino-6-((3-aminopropyl)amino)hexanoic Acid Dihydrochloride Inhibition of Glucose Uptake in 3T3-L1 Adipocytes The effect of (S)-2-amino-6-((3-aminopropyl)amino) hexanoic acid dihydrochloride on glucose uptake impairment in adipocytes was determined as follows.

a. 3T3-L1 Cell Culture

3T3-L1 Mouse Embryonic Fibroblasts, ATCC® CL-173™ were differentiated to adipocytes using chemically-induced differentiation according to the ATCC guidelines. Differentiated 3T3-L1 Adipocyte $4e^6$ cell were incubated overnight in glucose free media (RPMI ref. #11879 Gibco) containing 1% dialyzed fetal bovine serum (ref. #26400 Gibco) at 37° C. Cells were washed with and incubated for 1 h with glucose free media before compound exposure. Cells were incubated with and without increasing concentration (0.1, 1, 10 and 100 μM) of (S)-2-amino-6-((3-aminopropyl)amino)hexanoic acid dihydrochloride (title compound) for 2 h at 37° C., followed by 3 wash steps in glucose free phosphate buffer. Cells were then exposed to oxidative stress by incubating with 4HNE/$H_2O_2$ at 100 μM each for 1 h in glucose free media at 37° C. After incubation, the cells were washed steps and $^{13}C_6$-glucose uptake assay was performed as previously reported (Datta et al., *Cell Cycle*. 2016 September; 15(17):2288-98. doi: 10.1080/15384101.2016.1190054. (Epub 2016 May 31)).

B. Glucose Uptake

Cells were washed with PBS, followed by addition of glucose free DMEM medium containing 20 mM of $^{13}C_6$ glucose, 10 mM, 2-fluorodeoxyglucose (2-FDG) and insulin 10 pM (Sigma I5500) incubated for 1 hour at 37° C. 2-FDG is an inhibitor of glucose metabolism, thus preventing glucose breakdown and allowing its accumulation to further be measure and quantified. Cells were harvested, washed three times with 1×PBS and the cell pellet was lysed in 10 μl-PER buffer incubated 10 min at 4° C. and 90 μl of buffer A (20 mM ammonium hydroxide and 20 mM ammonium acetate) was added for extraction of metabolites and further analysis.

C. Metabolite Extraction

Proteins from the supernatant cell media or from the cell lysates were precipitated with 3 volumes of acetonitrile, and the liquid phase was concentrated in a speed-vacuum (Dietmair et al., *Anal Biochem*. 2010, 404:155-64). The dry pellet containing the metabolites was resuspended in buffer A and used to measure the metabolites.

D. Multiple Reaction Monitoring (MRM)

The detection of the $^{13}C_6$ glucose, was carried out using a Waters Xevo™ triple quadrupole tandem mass spectrometer (Waters Corp., Manchester, UK). IntelliStart software was used for method development of $^{13}C_6$ glucose metabolite and the optimization of the mass spectrometer parameters for best metabolite transitions detection condition. The UPLC/MS/MS method for the detection of $^{13}C_6$ glucose metabolite was developed for a complete separation and identification of the metabolic extracts for in less than 6 minutes per sample including a rapid elution of compounds and subsequent MRM. This method was confirmed using the metabolite standards in an ACQUITY UPLC® (100 mm×2.1 mm, 1.7 μm) BEH Amide C18 column heated to 40° C. employing a flow rate of 0.4 mL/min and mobile phases A and B, 20 mM ammonium hydroxide and 20 mM ammonium acetate in acetonitrile, respectively, and with the following gradient: 0% B, 0-1 min; 0% B-50% B, 1-2.5 min; 50% B-90% B, 2.5-3.2 min; 90% B to 0% B, 3.2-4 min; total run time 5 min. Chromatographic and mass spectrum data were collected and analyzed with Waters MassLynx v4.1 software. Quantification was obtained using linear regression analysis of the peak area ratio analyte versus concentration. The ratios of the precursor and fragment ions allow an accurate quantification of all the target metabolites. Standard calibration curves was performed using for $^{13}C_6$ glucose metabolite at concentrations of 0.01, 0.05, 0.1, 0.5, 1, 5, 10, 50, and 100 μM.

E. Results

Figure 5:
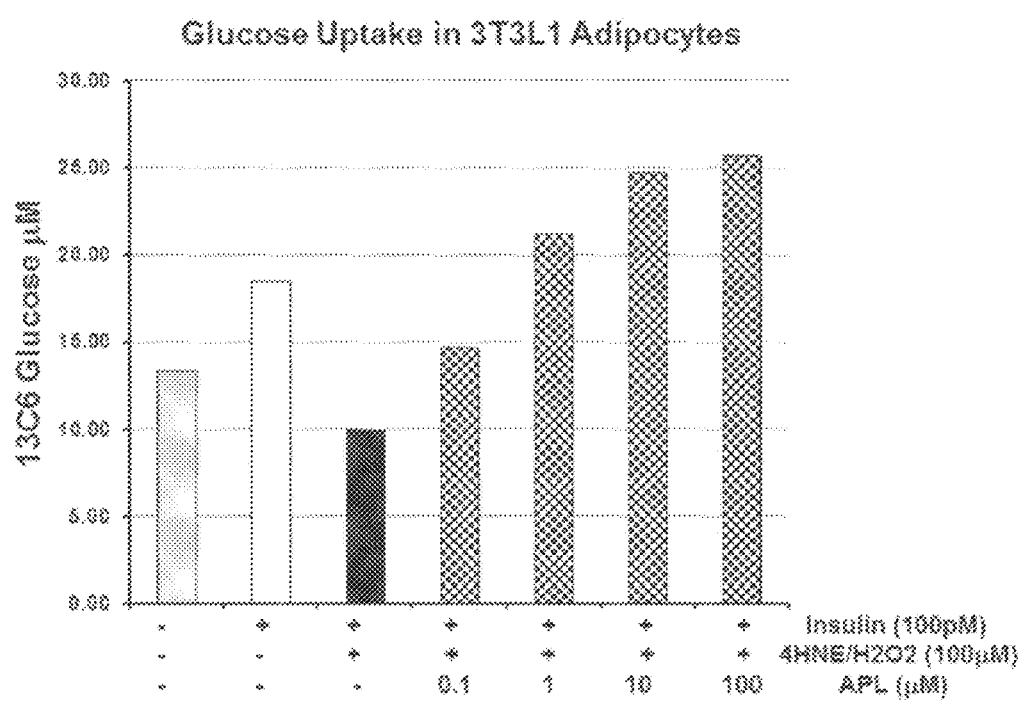
FIG. 5 is a plot of the glucose uptake of 3T3L1 adipocytes. Cells were treated with the indicated concentrations of the drug (S)-2-amino-6-((3-aminopropyl)amino)hexanoic acid dihydrochloride ("APL") and exposed to oxidative stress by incubating with 4HNE/$H_2O_2$ at 100 μM, followed by $^{13}C_6$-glucose uptake assay. The drug prevented glucose uptake-impairing effect of 4-HNE and $H_2O_2$, in a dose-dependent fashion.

The results are shown in FIG. 5. The title compound ("APL") was able to prevent the glucose uptake impairment induced by 4-HNE and $H_2O_2$, in a dose-dependent fashion.

Example 8

(S)-2-amino-6-((6-aminohexyl)amino)hexanoic Acid Trihydrochloride

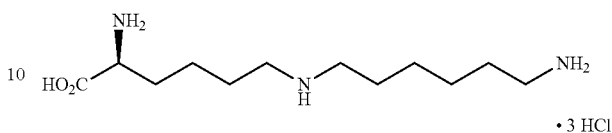

(S)-2-amino-6-((6-aminohexyl)amino)hexanoic acid trihydrochloride was prepared as follows:

i. Preparation of tert-butyl-(S)-(1-(3-((tert-butoxycarbonyl)amino)hexyl)-2-oxoazepan-3-yl)carbamate

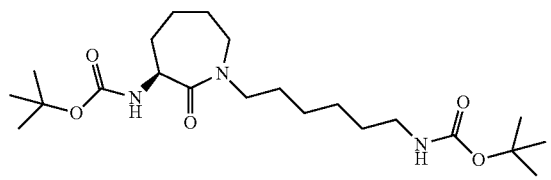 [SMILES: CC(C)(C)OC(=O)NCCCCCCN1CCCC[C@H](NC(=O)OC(C)(C)C)C1=O]

Lithium bis(trimethylsilyl)amide (0.8760 mmol; 876 μL of a 1.0 M solution in THF) was added to a solution of tert-butyl (S)-(2-oxoazepan-3-yl)carbamate (0.4380 mmol; 100 mg) in anhydrous tetrahydrofuran (1 mL). The resulting suspension was stirred at room temperature for thirty minutes. N-Boc-6-bromohexylamine (0.8760 mmol; 245 mg) was added all at once. The reaction was stirred at room temperature for 48 hours and then at 60° C. for 18 hours. It was concentrated down and the residue was partitioned between ethyl acetate and water. The aqueous layer was removed. The organic layer was washed with brine, dried over anhydrous sodium sulfate and concentrated. The crude product was purified by column chromatography on silica gel using a gradient solvent system of 0 to 40% of ethyl acetate in hexanes to afford the titled compound as a colorless oil. $^1$H NMR (400 MHz, $CDCl_3$) δ 6.00 (bd, J=5.8 Hz, 1H), 4.56 (bs, 1H), 4.33 (m, 1H), 3.43-3.52 (m, 2H), 3.36-3.41 (m, 1H), 3.25-3.33 (m, 1H), 3.15-3.23 (m, 1H), 3.05-3.13 (m, 2H), 1.89-1.98 (m, 1H), 1.74-1.88 (m, 3H), 1.41-1.54 (m, 22H), 1.27-1.36 (m, 5H); MS (ESI): m/z 428.3 [(M+H)$^+$].

(B) Preparation of (S)-2-amino-6-((6-aminohexyl)amino)hexanoic Acid Trihydrochloride

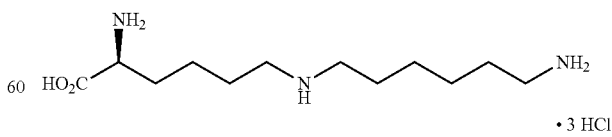

Tert-butyl (S)-(1-(6-((tert-butoxycarbonyl)amino)hexyl)-2-oxoazepan-3-yl)carbamate (0.0215 mmol; 9.2 mg) was dissolved into 12 N aqueous hydrochloric acid (1 mL). This solution was stirred at room temperature until all of the bubbling had ceased. It was transferred to a microwave reaction vial and heated at 160° C. for ninety minutes. Upon concentration, pure titled compound was afforded as a pale yellow oil. $^1$H NMR (400 MHz, D$_2$O) δ 4.08 (t, J=6.4 Hz, 1H), 2.98-3.10 (m, 6H), 1.92-2.06 (m, 2H), 1.64-1.81 (m, 6H), 1.40-1.57 (m, 6H); MS (ESI): m/z 246.2 [(M+H)+].

Example 9

(S)-2-amino-6-((3-aminopropyl)amino)hexanoic Acid Dihydrochloride Forms Adducts with 4-HNE The following study demonstrates that a compound of the invention, (S)-2-amino-6-((3-aminopropyl)amino)hexanoic acid dihydrochloride forms an adduct with 4-HNE, thereby diverting 4-HNE from damaging GLUT-4 by carbonylation. The experimental design was to incubate equimolar amounts (10 μM) of APL (dihydrochloride) with 4-HNE and measure adduct formation by mass spectroscopy before and after 1 hr incubation at 37° C.

The results are shown in FIGS. 6A and 6B. As shown in FIG. 6A, APL is detected prior to addition of 4-HINE. As shown in FIG. 6B, APL forms an adduct with 4-HNE after 1 hr of incubation.

Example 10

Reversal of Glucose Uptake Impairment in Overnourished Animals

The effect of (S)-2-amino-6-((3-aminopropyl)amino) hexanoic acid dihydrochloride in reversing overnutrition-induced glucose uptake impairment was demonstrated as follows.

Twenty-four C$_{57}$BL/6J mice 8-weeks old were fed with either regular CHOW diet or high fat diet (HFD, 60% of fat content). Eight animals received CHOW diet for one week, 8 animals had been fed already with HFD for two weeks and were continuously fed with the same diet for one more week (for a total of 3 weeks feeding) and 8 animals started HFD at the time of the animal selection (2 weeks feeding). Each group was divided in half, 4 animals received regular water and the other 4 received the (S)-2-amino-6-((3-aminopropyl)amino)hexanoic acid dihydrochloride (10 μg/mL) dissolved in the water. Animals were fasted for 5 hours, weighed, and blood glucose measured by tail clipping. In addition, glucose (1 mg/g of body weight) was administered intraperitoneally. Additional glucose levels were measured at 20, 40 and 80 minutes after glucose administration. Heavy glucose was also administered intraperitoneally to further measure glucose uptake from tissues. Glucose level was taken again at 140 minutes. Animals were euthanized under anesthesia (isoflurane), and blood, liver, fat and muscle were collected.

Figure 7:
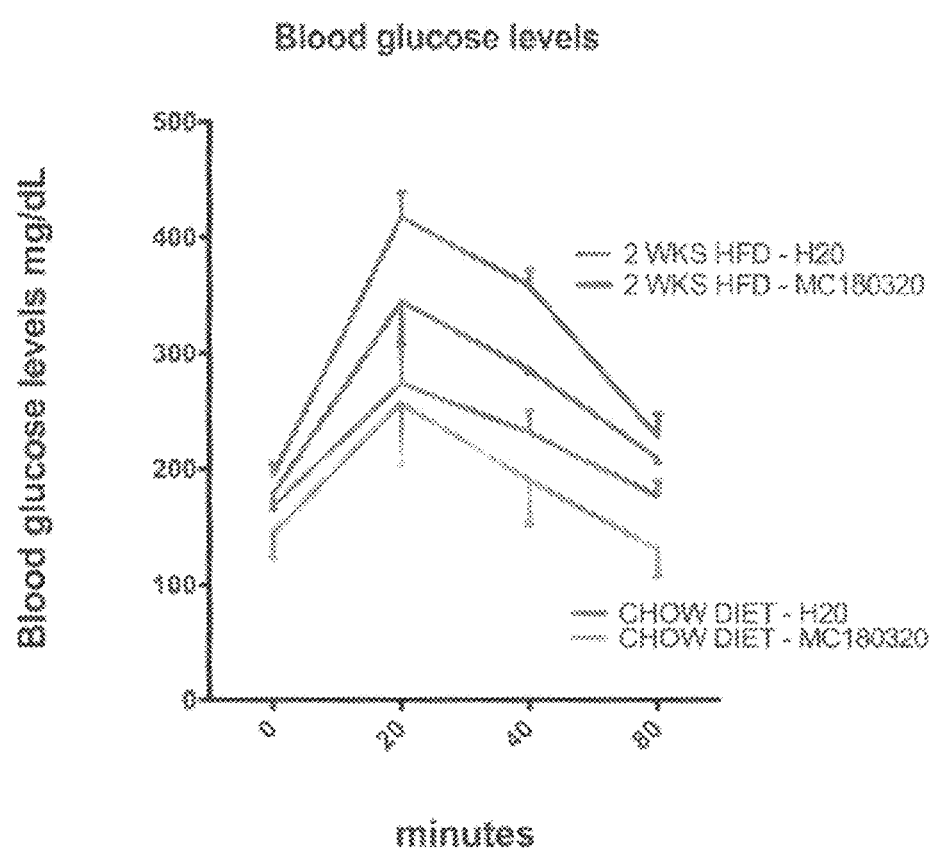
FIG. 7 is a plot of blood glucose levels in mice fed with either a regular CHOW diet or high fat diet (HFD), followed by water without or with (S)-2-amino-6-((3-aminopropyl) amino)hexanoic acid dihydrochloride (10 μg/ml) ("APL").

The results in FIG. 7 demonstrate that the active agent (S)-2-amino-6-((3-aminopropyl)amino)hexanoic acid dihydrochloride was effective in counteracting glucose uptake impairment induced by overnutrition in cells.

Example 11

Reduction of GLUT4 Carbonylation in Overnourished Animals—Further Study

The following further study demonstrates the effect of (S)-2-amino-6-((3-aminopropyl)amino)hexanoic acid dihydrochloride in reducing GLUT4 carbonylation in the adipose tissue of mice fed on a high fat diet.

A. Methods

Thirty-two C57BL/6J mice 8-weeks old were selected and randomly separated. The mice (n=8) were fed ad libitum for two weeks with either CHOW diet or high fat diet (HFD, 60% of fat content). Each group was divided in half 8 animals received regular water and the other 8 received (S)-2-amino-6-((3-aminopropyl)amino)hexanoic acid dihydrochloride dissolved in water so as to administer about 10 mg/kg of the drug body weight per mouse, per day. As an additional experimental control (n=8), a group of mice receiving HFD also received pioglitazone (10 mg/kg). Poglitazone is a well-known anti-diabetic agent. It has the ability to increase glucose uptake into the cells. Poglitazone has also been shown to reduce protein carbonylations (Xu, Q., Hahn, W. S. & Bernlohr, D. A. (2014) Detecting protein carbonylation in adipose tissue and in cultured adipocytes. *Methods in enzymology* 538, 249-261, doi:10.1016/B978-0-12-800280-3.00014-1). At the end of the two weeks, animals were fasted for 5 hours, weighed, and their tails were clipped to measure fasting blood glucose levels. Immediately after, glucose was administered intraperitoneally (1 mg/g of body weight). Glucose levels were measured at 20, 40, 80 and 140 minutes after glucose administration in a glucose time test (GTT). Animals were euthanized under anesthesia (isoflurane). Blood, liver, fat and muscle tissues were collected and flash frozen for the studies.

The levels of GLUT4 carbonylations in adipose tissue in the HFD-fed control animals and the HFD animals receiving (S)-2-amino-6-((3-aminopropyl)amino)hexanoic acid dihydrochloride were measured by the MRM method described above.

The body weights of diet-induced (HFD) mice with and without (S)-2-amino-6-((3-aminopropyl)amino)hexanoic acid dihydrochloride (10 mg/kg/day) were measured over 14 days.

B. Results: Levels of GLUT4 Carbonylations

As shown in FIG. 8A (n=8; P<0.02), the active agent (S)-2-amino-6-((3-aminopropyl)amino)hexanoic acid dihydrochloride ("APL") was again effective in reducing overnutrition-induced GLUT4 carbonylation in adipose tissue of treated individuals. The drug was effective in reducing GLUT4 carbonylations by about 50% (FIG. 8A).

C. Results: Glucose Tolerance Test

To determine the effects of the compound (S)-2-amino-6-((3-aminopropyl)amino)hexanoic acid dihydrochloride on glucose tolerance, mice that received (i) HFD+poglitazone, (ii) HFD+vehicle, (iii) HFD+(S)-2-amino-6-((3-aminopropyl)amino)hexanoic acid dihydrochloride and (iv) Chow diet (control) were subjected to a glucose tolerance test (GTT). As indicated in FIG. 8B, the drug (S)-2-amino-6-((3-aminopropyl)amino)hexanoic acid dihydrochloride ("APL") reduced fasting glucose levels.

FIG. 8C shows the results of the glucose time test for animal groups (i) through (iv). Glucose tolerance was impaired in HFD as compared to chow controls. Interestingly, the glucose tolerance test was drastically improved in mice treated with (S)-2-amino-6-((3-aminopropyl)amino) hexanoic acid dihydrochloride. Pioglitazone showed only moderate glucose tolerance improvement. The pioglitazone results are consistent with the published data (Xu, Q., Hahn, W. S. & Bernlohr, D. A. (2014) Detecting protein carbonylation in adipose tissue and in cultured adipocytes. *Methods in enzymology* 538, 249-261, doi:10.1016/B978-0-12-800280-3.00014-1).

Similar results were obtained when the areas under the curves of the glucose tolerance test data of FIG. 8C were calculated. The areas under the curves of FIG. 8C are represented as bar graphs in FIG. 8D.

In FIGS. 8A-8D, all data points and error bars represent mean±s.e.m. The statistics were performed using two-tail Student's t-test and the significance levels are *p<0.05; **p<0.02.

D. Results: Body Weight

FIG. 9 shows the body weight of diet-induced (HFD) obese mice over two weeks during treatment with 10 mg/kg/day (S)-2-amino-6-((3-aminopropyl)amino)hexanoic acid dihydrochloride ("APL") and without APL ("Control"). The drug had no effect on body weight. In contrast, poglitazone is known to cause water retention and weight gain. Also, the fact that body weight did not decrease is evidence of lack of significant toxicity.

Example 12

Reduction of Impaired Glucose Tolerance in Pre-Diabetes and Diabetes Stages in Leptin Obese (db/db) Mice The following study demonstrates the effect of (S)-2-amino-6-((3-aminopropyl)amino)hexanoic acid dihydrochloride in reducing impaired glucose tolerance in a pre-diabetic stage.

Leptin receptor knock-out (db/db) mice have severe, rapid, spontaneous and early-onset obesity and insulin resistance that is first recognizable at 4 weeks of age. These animals (5 for each group) were used to determine the effect of (S)-2-amino-6-((3-aminopropyl)amino)hexanoic acid dihydrochloride on impaired glucose tolerance at pre-diabetes level. The groups consisted of (i) db/db mice administered 50 mg/kg b.i.d. p.o. (S)-2-amino-6-((3-aminopropyl)amino)hexanoic acid dihydrochloride; (ii) db/db vehicle control-treated mice; and (iii) heterozygous littermate control mice. The treatment period was for 7 days. Glucose tolerance tests were performed as described above. The results shown in FIG. 10 demonstrate that (S)-2-amino-6-((3-aminopropyl)amino)hexanoic acid dihydrochloride ("APL") normalizes impaired glucose tolerance in in pre-diabetic db/db mice.

To determine the effect of (S)-2-amino-6-((3-aminopropyl)amino)hexanoic acid dihydrochloride on impaired glucose tolerance after diabetes is established, 6 week old db/db mice were treated with the drug (50 mg/kg b.i.d. p.o.) for 14 days. The positive control group was treated with metformin at the same dose. The results in FIG. 11 indicate that (S)-2-amino-6-((3-aminopropyl)amino)hexanoic acid dihydrochloride ("APL") is better in reducing impaired glucose tolerance than metformin, the first-line medication for the treatment of type 2 diabetes. The results establish that the drug can be used to treat both pre-diabetes, and diabetes wherein the diabetic phenotype has been established.

Example 13

Delay of Disease Progression in Leptin Obese (Db/Db) Mice

To assess whether (S)-2-amino-6-((3-aminopropyl)amino)hexanoic acid dihydrochloride delays progression to diabetes or only masks diabetes during treatment period, (i) db/db mice (ii) db/db vehicle control-treated mice; and (iii) heterozygous littermate control mice were treated with and without (S)-2-amino-6-((3-aminopropyl)amino)hexanoic acid dihydrochloride or metformin (50 mg/kg b.i.d. p.o.) for 14 days. The 14 day treatment period was followed by another 14 day period ("wash out period") in which no treatment was given. The results in FIG. 12 show that (S)-2-amino-6-((3-aminopropyl)amino)hexanoic acid dihydrochloride ("APL") is still effective in reducing impaired glucose tolerance even after 14 days following treatment removal. The results indicate that the drug is diabetes-modulating. It does not just mask the disease.

Example 14

The following study demonstrates the ability of (S)-2-amino-6-((3-aminopropyl)amino)hexanoic acid dihydrochloride to reduce GLUT4 carbonylations and prevent glucose uptake impairment induced by 4-HNE and $H_2O_2$. Insulin-stimulated 3T3-L1 adipocytes were pretreated with the drug (S)-2-amino-6-((3-aminopropyl)amino)hexanoic acid dihydrochloride (10 μM) for 12 hours followed by exposure to 4HNE and $H_2O_2$ for an additional 4 hours. The amounts of glucose taken up by the 3T3-L1 adipocytes were measured by the MRM methods described above. The results in FIG. 13 show the effect of the drug in restoring glucose uptake in insulin-stimulated 3T3-L1 cells exposed to 4-HNE and $H_2O_2$: Control cells, no insulin (C− No Ins); control cells, with insulin (C+ Ins); 4HNE+$H_2O_2$-treated cells (4HNE/H2O2) and cells treated with drug+4HNE+$H_2O_2$ ("APL").

Example 15

(S)-2-amino-5-((6-aminohexyl)amino)pentanoic Acid Trihydrochloride

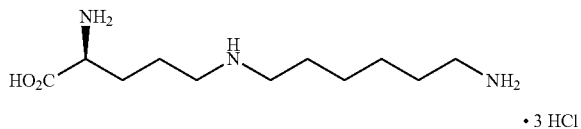 [SMILES: NCCCCCCNCCC[C@H](N)C(=O)O]

(S)-2-amino-5-((6-aminohexyl)amino)pentanoic acid trihydrochloride was prepared as follows.

a. Preparation of tert-butyl (6-oxohexyl)carbamate

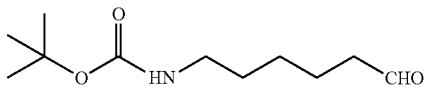

Anhydrous dimethyl sulfoxide (83 uL) was added dropwise to a stirred solution of oxalyl chloride (50 uL) in anhydrous dichloromethane (2 mL) at −78° C. After stirring for 15 minutes, a solution of 6-(tert-butoxy-carbonylamino)-1-hexanol (115 mg, 0.53 mmol) in anhydrous dichloromethane (1 mL) was added dropwise. The resulting mixture was stirred at −78° C. for 45 minutes. Triethylamine (368 uL) was added and the reaction was allowed to warm to room temperature. This solution was concentrated on a rotary evaporator to afford the titled compound as an off-white solid (86 mg, 75% yield) which was used without further purification.

B. Preparation of (S)-2-(((benzyloxy)carbonyl)amino)-5-((6-((tert-butoxycarbonyl)amino)hexyl)amino)-pentanoic Acid

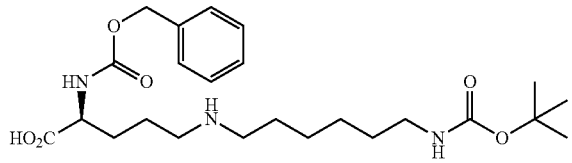 [SMILES: CC(C)(C)OC(=O)NCCCCCCNCCC[C@H](NC(=O)OCc1ccccc1)C(=O)O]

To a stirred suspension of N-alpha-benzyloxycarbonyl-L-ornithine 94 mg, (0.352 mmol) in anhydrous methanol (2 mL) containing acetic acid (100 uL) was added a solution of tert-butyl (6-oxohexyl)carbamate (114 mg, 0.528 mmol) in anhydrous methanol (1.9 mL). The resulting mixture was stirred at room temperature for 30 minutes. Sodium cyanoborohydride (66 mg, 1.057 mmol) was then added and the reaction was stirred at room temperature overnight. After concentration on a rotary evaporator, the residue was partitioned between ethyl acetate and 1M aqueous potassium bisulfate. The aqueous layer was removed. The organic phase was washed with water and brine, dried over anhydrous sodium sulfate and concentrated on a rotary evaporator. The resulting residue was purified by reversed phase chromatography (C18 column) using a gradient of 10 to 100% acetonitrile in water with 0.1% formic acid modifier. The titled compound (87 mg, 53% yield) was obtained as a pale yellow oil. $^1$H NMR (400 MHz, D$_2$O) δ 3.94 (t, J=5.92 Hz, 0.5H), 3.63 (m, 0.5H), 2.99-3.13 (m, 6H), 1.65-2.04 (m, 8H), 1.43 (m, 4H); MS (ESI): m/z 466.2 [(M+H)$^+$].

(C) Preparation of (S)-2-Amino-5-((6-aminohexyl)amino)pentanoic Acid Trihydrochloride

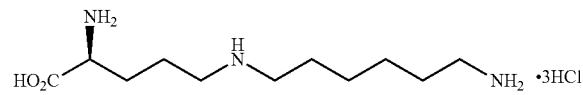 [SMILES: NCCCCCCNCCC[C@H](N)C(=O)O]

A solution of (S)-2-(((benzyloxy)carbonyl)amino)-5-((6-((tert-butoxycarbonyl)amino)hexyl)amino)pentanoic acid (18 mg, 0.039 mmol)) in 6N aqueous hydrochloric acid (4 mL) was refluxed for two hours. This solution was concentrated on a rotary evaporator to afford the titled compound (12 mg, 90% yield) as a pale yellow oil. $^1$H NMR (400 MHz, D$_2$O) δ 4.27 (m, 0.5H), 3.95 (m, 0.5H), 3.33-3.48 (m, 6H), 2.00-2.37 (m, 8H), 1.77 (m, 4H); MS (ESI): m/z 232.2 [(M+H)$^+$].

D. Effect of (S)-2-amino-5-((6-aminohexyl)amino)pentanoic Acid Trihydrochloride in Restoring Glucose Uptake in Insulin-Stimulated 3T3-L1 Cells Exposed to 4-HNE and H$_2$O$_2$ Insulin-stimulated 3T3-L1 adipocytes were pretreated with the drug (S)-2-amino-5-((6-aminohexyl)amino)pentanoic acid dihydrochloride (10 μM) for 12 hours followed by exposure to 4HNE and H$_2$O$_2$ for an additional 4 hours. The amounts of glucose taken up by the 3T3-L1 adipocytes were measured by the MRM methods described above. FIG. 13 includes the results: cells treated with (S)-2-amino-5-((6-aminohexyl)amino)pentanoic acid trihydrochloride (MC-180351). The data shows demonstrates the ability of (S)-2-amino-5-((6-aminohexyl)amino)pentanoic acid trihydrochloride to reduce GLUT4 carbonylations and prevent glucose uptake impairment induced by 4-HNE and H$_2$O$_2$.

Example 16

(S)-2-amino-5-((5-aminopentyl)amino)pentanoic Acid Trihydrochloride

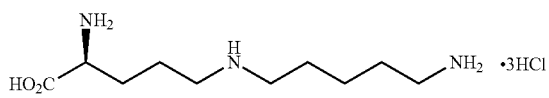

(S)-2-amino-5-((5-aminopentyl)amino)pentanoic acid trihydrochloride was prepared as follows.

A. Preparation of tert-butyl (5-oxopentyl)carbamate

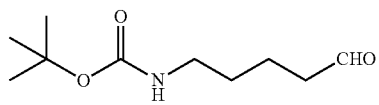

Anhydrous dimethyl sulfoxide (58 uL) was added dropwise to a stirred solution of oxalyl chloride (35 uL) in anhydrous dichloromethane (1.5 mL) at −78° C. After stirring for 15 minutes, a solution of 6-(tert-butoxy-carbonylamino)-1-pentanol (75 mg, 0.37 mmol) in anhydrous dichloromethane (0.75 mL) was added dropwise. The resulting mixture was stirred at −78° C. for 45 minutes. Triethylamine (257 uL) was added and the reaction was allowed to warm to room temperature. This solution was concentrated on a rotary evaporator to afford the titled compound as an off-white solid (52 mg, 70% yield) which was used without further purification.

B. Preparation of (S)-2-(((benzyloxy)carbonyl)amino)-5-((5-((tert-butoxycarbonyl)amino)pentyl)amino)-pentanoic Acid

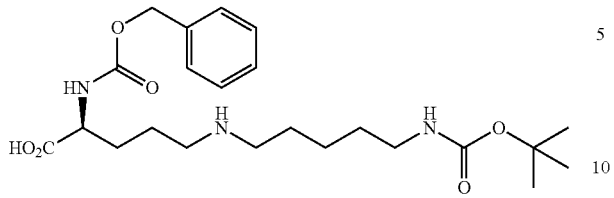

To a stirred suspension of N-alpha-benzyloxycarbonyl-L-ornithine 35 mg, (0.13 mmol) in anhydrous methanol (1 mL) containing acetic acid (38 uL) was added a solution of tert-butyl (5-oxopentyl)carbamate (40 mg, 0.20 mmol) in anhydrous methanol (1.0 mL). The resulting mixture was stirred at room temperature for 30 minutes. Sodium cyanoborohydride (25 mg, 0.40 mmol) was then added and the reaction was stirred at room temperature overnight. After concentration on a rotary evaporator, the residue was partitioned between ethyl acetate and 1M aqueous potassium bisulfate. The aqueous layer was removed. The organic phase was washed with water and brine, dried over anhydrous sodium sulfate and concentrated on a rotary evaporator. The resulting residue was purified by reversed phase chromatography (C18 column) using a gradient of 10 to 100% acetonitrile in water with 0.1% formic acid modifier. The titled compound (34 mg, 58% yield) was obtained as a colorless oil. $^1$H NMR (400 MHz, CD$_3$OD) δ 7.26-7.38 (m, 5H), 5.08 (s, 2H), 4.03 (m, 1H), 2.90-3.07 (m, 6H), 1.87 (m, 1H), 1.65-1.79 (m, 5H), 1.34-1.54 (m, 13H); MS (ESI): m/z 452.30 [(M+H)$^+$].

C. Preparation of (S)-2-amino-5-((5-aminopentyl)amino)pentanoic Acid Trihydrochloride

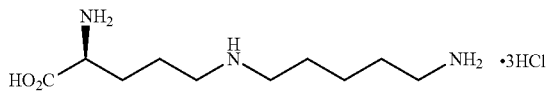 [SMILES: NCCCCCNCCC[C@H](N)C(=O)O]

A solution of (S)-2-(((benzyloxy)carbonyl)amino)-5-((5-((tert-butoxycarbonyl)amino)pentyl)amino)pentanoic acid (20 mg, 0.044 mmol)) in 6N aqueous hydrochloric acid (4 mL) was refluxed for two hours. This solution was concentrated on a rotary evaporator to afford the titled compound (12 mg, 88% yield) as a pale yellow oil. $^1$H NMR (400 MHz, CD$_3$OD) δ 4.06 (t, J=5.36 Hz, 1H), 3.06 (m, 4H), 2.96 (t, J=7.52 Hz, 2H), 1.88-2.10 (m, 4H), 1.68-1.83 (m, 4H), 1.47-1.55 (m, 2H); MS (ESI): m/z 218.2 [(M+H)$^+$].

D. Effect of (S)-2-amino-5-((5-aminopentyl)amino) pentanoic Acid Trihydrochloride in Restoring Glucose Uptake in Insulin-Stimulated 3T3-L1 Cells Exposed to 4-HNE and H$_2$O$_2$ Insulin-stimulated 3T3-L1 adipocytes were pretreated with the drug (S)-2-amino-5-((5-aminoheptyl)amino)pentanoic acid dihydrochloride (10 μM) for 12 hours followed by exposure to 4HNE and H$_2$O$_2$ for an additional 4 hours. The amounts of glucose taken up by the 3T3-L1 adipocytes were measured by the MRM methods described above. FIG. 13 includes the results: cells treated with (S)-2-amino-5-((5-aminopentyl)amino)pentanoic acid trihydrochloride (MC-180352). The data shows demonstrates the ability of (S)-2-amino-5-((5-aminoheptyl)amino)pentanoic acid dihydrochloride to reduce GLUT4 carbonylations and prevent glucose uptake impairment induced by 4-HNE and H$_2$O$_2$.

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

We claim:

1. A method of reducing impaired glucose tolerance in a subject in need thereof, comprising administering to the subject an effective amount of a compound according to Formula I:

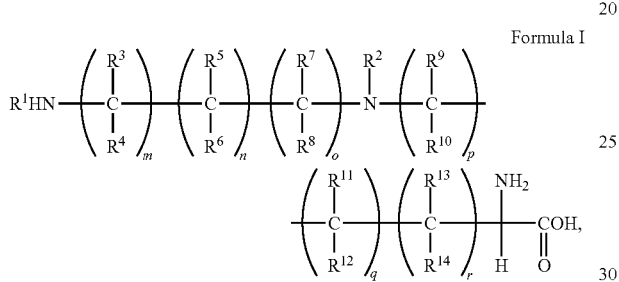

Formula I or a pharmaceutically acceptable salt thereof, wherein:

$R^1$ is selected from the group consisting of hydrogen, —($C_1$-$C_8$)alkyl, —($C_1$-$C_8$)alkenyl, —($C_1$-$C_8$)alkynyl, unsubstituted or substituted -ara($C_1$-$C_6$)alkyl, unsubstituted or substituted -heteroara($C_1$-$C_6$)alkyl, where the substituents on said substituted ara($C_1$-$C_6$)alkyl and substituted heteroara($C_1$-$C_6$)alkyl are selected from the group consisting of halogen, —CN, —$NO_2$, —$NH_2$, —NH($C_1$-$C_6$)alkyl, —N[($C_1$-$C_6$)alkyl)]$_2$, —OH, halo($C_1$-$C_6$)alkyl, —($C_1$-$C_6$)alkoxy, halo($C_1$-$C_6$)alkoxy, —SH, thio($C_1$-$C_6$)alkyl, —$SONH_2$, —$SO_2NH_2$, —SO—($C_1$-$C_6$)alkyl, —$SO_2$—($C_1$-$C_6$)alkyl, —$NHSO_2$($C_1$-$C_6$)alkyl, and —$NHSO_2NH_2$;

$R^2$ is selected from the group consisting of hydrogen, —($C_1$-$C_8$)alkyl, —($C_1$-$C_8$)alkenyl, —($C_1$-$C_8$)alkynyl, unsubstituted or substituted -ara($C_1$-$C_6$)alkyl, unsubstituted or substituted -heteroara($C_1$-$C_6$)alkyl, where the substituents on said substituted ara($C_1$-$C_6$)alkyl and substituted heteroara($C_1$-$C_6$)alkyl are selected from the group consisting of halogen, —CN, —$NO_2$, —$NH_2$, —OH, halo($C_1$-$C_6$)alkyl, —($C_1$-$C_6$)alkoxy, halo($C_1$-$C_6$)alkoxy, —SH, thio($C_1$-$C_6$)alkyl, —$SONH_2$, —$SO_2NH_2$, —SO—($C_1$-$C_6$)alkyl, —$SO_2$—($C_1$-$C_6$)alkyl, —$NHSO_2$($C_1$-$C_6$)alkyl, and —$NHSO_2NH_2$;

$R^3$, $R^4$, $R^7$, $R^8$, $R^9$, $R^{10}$, $R^{13}$ and $R^{14}$ are independently selected from the group consisting of hydrogen and —($C_1$-$C_6$)alkyl;

$R^5$ and $R^6$ are independently selected from the group consisting of hydrogen, —($C_1$-$C_6$)alkyl and —OH, provided that both $R^5$ and $R^6$ cannot be —OH;

$R^{11}$ and $R^{12}$ are independently selected from the group consisting of hydrogen, —($C_1$-$C_6$)alkyl and —OH, provided that both $R^{11}$ and $R^{12}$ cannot be —OH;

m is 1, 2, 3, or 4;
n is 0, 1, 2, 3, or 4;
o is 0, 1, 2, 3, or 4;
p is 1, 2, 3, or 4;
q is 0, 1, 2, 3, or 4; and
r is 0, 1, 2, 3, or 4.

2. The method of claim 1, wherein each of $R^3$, $R^4$, $R^5$, $R^6$, $R^7$, $R^8$, $R^9$, $R^{10}$, $R^{11}$, $R^{12}$, $R^{13}$ and $R^{14}$ is hydrogen.

3. The method of claim 2, wherein each of $R^1$ and $R^2$ is hydrogen.

4. The method of claim 2, wherein
m is 3; p is 4; and each of n, o, q and r is zero;
m is 4; n is 2; p is 3; and each of o, q and r is zero; or
m is 4; n is 1; p is 3; and each of o, q and r is zero.

5. The method of claim 1, wherein the compound is (S)-2-amino-6-((3-aminopropyl)amino)hexanoic acid, or a pharmaceutically acceptable salt thereof.

6. The method of claim 1, wherein the compound is selected from the group consisting of:
(S)-2-amino-6-((6-aminohexyl)amino)hexanoic acid;
(S)-2-amino-5-((6-aminohexyl)amino)pentanoic acid; and
(S)-2-amino-5-((5-aminopentyl)amino)pentanoic acid,
or a pharmaceutically acceptable salt thereof.

7. The method of claim 1, wherein the subject is diabetic or pre-diabetic.

8. The method of claim 1, wherein the subject is obese.

9. A method of treating or preventing diabetes in a subject in need thereof, comprising administering to the subject an effective amount of a compound according to Formula I:

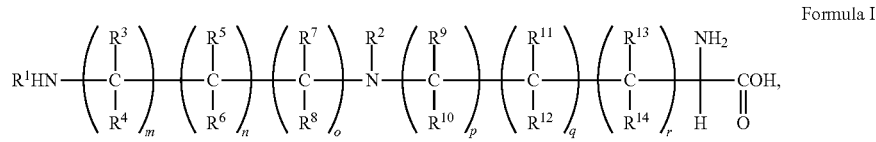

Formula I or a pharmaceutically acceptable salt thereof, wherein:

R$^1$ is selected from the group consisting of hydrogen, —(C$_1$-C$_8$)alkyl, —(C$_1$-C$_8$)alkenyl, —(C$_1$-C$_8$)alkynyl, unsubstituted or substituted -ara(C$_1$-C$_6$)alkyl, unsubstituted or substituted -heteroara(C$_1$-C$_6$)alkyl, where the substituents on said substituted ara(C$_1$-C$_6$)alkyl and substituted heteroara(C$_1$-C$_6$)alkyl are selected from the group consisting of halogen, —CN, —NO$_2$, —NH$_2$, —NH(C$_1$-C$_6$)alkyl, —N[(C$_1$-C$_6$)alkyl]$_2$, —OH, halo(C$_1$-C$_6$)alkyl, —(C$_1$-C$_6$)alkoxy, halo(C$_1$-C$_6$)alkoxy, —SH, thio(C$_1$-C$_6$)alkyl, —SONH$_2$, —SO$_2$NH$_2$, —SO—(C$_1$-C$_6$)alkyl, —SO$_2$—(C$_1$-C$_6$)alkyl, —NHSO$_2$(C$_1$-C$_6$)alkyl, and —NHSO$_2$NH$_2$;

R$^2$ is selected from the group consisting of hydrogen, —(C$_1$-C$_8$)alkyl, —(C$_1$-C$_8$)alkenyl, —(C$_1$-C$_8$)alkynyl, unsubstituted or substituted -ara(C$_1$-C$_6$)alkyl, unsubstituted or substituted -heteroara(C$_1$-C$_6$)alkyl, where the substituents on said substituted ara(C$_1$-C$_6$)alkyl and substituted heteroara(C$_1$-C$_6$)alkyl are selected from the group consisting of halogen, —CN, —NO$_2$, —NH$_2$, —OH, halo(C$_1$-C$_6$)alkyl, —(C$_1$-C$_6$)alkoxy, halo(C$_1$-C$_6$)alkoxy, —SH, thio(C$_1$-C$_6$)alkyl, —SONH$_2$, —SO$_2$NH$_2$, —SO—(C$_1$-C$_6$)alkyl, —SO$_2$—(C$_1$-C$_6$)alkyl, —NHSO$_2$(C$_1$-C$_6$)alkyl, and —NHSO$_2$NH$_2$;

R$^3$, R$^4$, R$^7$, R$^8$, R$^9$, R$^{10}$, R$^{13}$ and R$^{14}$ are independently selected from the group consisting of hydrogen and —(C$_1$-C$_6$)alkyl;

R$^5$ and R$^6$ are independently selected from the group consisting of hydrogen, —(C$_1$-C$_6$)alkyl and —OH, provided that both R$^5$ and R$^6$ cannot be —OH;

R$^{11}$ and R$^{12}$ are independently selected from the group consisting of hydrogen, —(C$_1$-C$_6$)alkyl and —OH, provided that both R$^{11}$ and R$^{12}$ cannot be —OH;

m is 1, 2, 3, or 4;
n is 0, 1, 2, 3, or 4;
o is 0, 1, 2, 3, or 4;
p is 1, 2, 3, or 4;
q is 0, 1, 2, 3, or 4; and
r is 0, 1, 2, 3, or 4.

10. The method of claim 9, wherein each of R$^3$, R$^4$, R$^5$, R$^6$, R$^7$, R$^8$, R$^9$, R$^{10}$, R$^{11}$, R$^{12}$, R$^{13}$ and R$^{14}$ is hydrogen.

11. The method of claim 10, wherein each of R$^1$ and R$^2$ is hydrogen.

12. The method of claim 10, wherein
m is 3; p is 4; and each of n, o, q and r is zero;
m is 4; n is 2; p is 3; and each of o, q and r is zero; or
m is 4; n is 1; p is 3; and each of o, q and r is zero.

13. The method of claim 9, wherein the compound is (S)-2-amino-6-((3-aminopropyl)amino)hexanoic acid, or a pharmaceutically acceptable salt thereof.

14. The method of claim 9, wherein the compound is selected from the group consisting of:
(S)-2-amino-6-((6-aminohexyl)amino)hexanoic acid;
(S)-2-amino-5-((6-aminohexyl)amino)pentanoic acid; and
(S)-2-amino-5-((5-aminopentyl)amino)pentanoic acid,
or a pharmaceutically acceptable salt thereof.

15. The method of claim 9, wherein the subject is pre-diabetic.

16. The method of claim 15, wherein the subject is obese.
17. The method of claim 9, wherein the subject is diabetic.
18. The method of claim 17, wherein the subject is obese.
19. The method of claim 17, wherein the subject has type 2 diabetes.
20. The method of claim 19, wherein the subject has hyperglycemia and/or hyperlipidemia.

21. The method of claim 20, wherein the subject has hyperglycemia and hyperlipidemia.

22. The method of claim 5, wherein the pharmaceutically acceptable salt is a hydrochloride salt.

23. The method of claim 22, wherein the compound is (S)-2-amino-6-((3-aminopropyl)amino)hexanoic acid dihydrochloride,

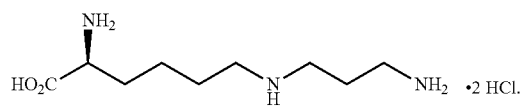 [SMILES: NCCCNCCCC[C@H](N)C(=O)O]

24. The method of claim 6, wherein the pharmaceutically acceptable salt is a hydrochloride salt.

25. The method of claim 24, wherein the compound is selected from the group consisting of:
(S)-2-amino-6-((6-aminohexyl)amino)hexanoic acid trihydrochloride,

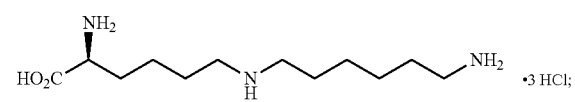 [SMILES: NCCCCCCNCCCC[C@H](N)C(=O)O]

(S)-2-amino-5-((6-aminohexyl)amino)pentanoic acid trihydrochloride

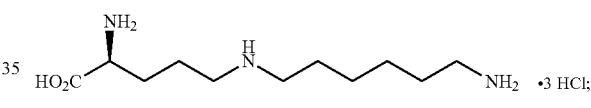

and (S)-2-amino-5-((5-aminopentyl)amino)pentanoic acid trihydrochloride

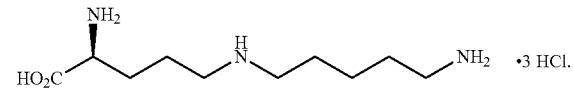

26. The method of claim 13, wherein the pharmaceutically acceptable salt is a hydrochloride salt.

27. The method of claim 24, wherein the compound is (S)-2-amino-6-((3-aminopropyl)amino)hexanoic acid dihydrochloride,

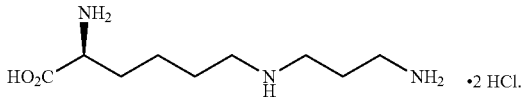 [SMILES: NCCCNCCCC[C@H](N)C(=O)O]

28. The method of claim 14, wherein the pharmaceutically acceptable salt is a hydrochloride salt.

29. The method of claim 28, wherein the compound is selected from the group consisting of:
(S)-2-amino-6-((6-aminohexyl)amino)hexanoic acid trihydrochloride,

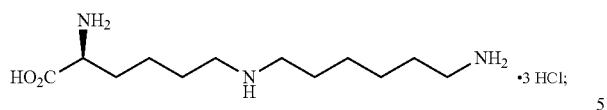
(S)-2-amino-5-((6-aminohexyl)amino)pentanoic acid trihydrochloride
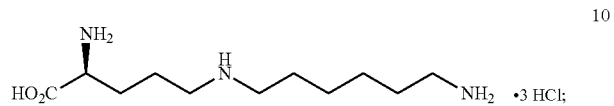
and
(S)-2-amino-5-((5-aminopentyl)amino)pentanoic acid trihydrochloride
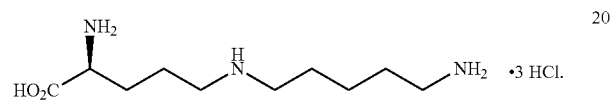
\* \* \* \* \*

UNITED STATES PATENT AND TRADEMARK OFFICE
CERTIFICATE OF CORRECTION

| | | |
|---|---|---|
| PATENT NO. | : 11,596,615 B2 | Page 1 of 1 |
| APPLICATION NO. | : 16/932236 | |
| DATED | : March 7, 2023 | |
| INVENTOR(S) | : Salim Merali et al. | |

It is certified that error appears in the above-identified patent and that said Letters Patent is hereby corrected as shown below:

In the Specification

On Column 1, Line 16, please replace the paragraph titled "REFERENCE TO GOVERNMENT GRANT" with the following paragraph:
--STATEMENT REGARDING FEDERALLY SPONSORED RESEARCH OR DEVELOPMENT
This invention was made with government support under R01 DK090588 awarded by the National Institutes of Health. The government has certain rights in the invention.--

Signed and Sealed this
Ninth Day of July, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: fragment of GLUT4 (amino acids 247-264)

<400> SEQUENCE: 1

Leu Thr Gly Trp Ala Asp Val Ser Gly Val Leu Ala Glu Leu Lys Asp
1               5                   10                  15

Glu Lys

<210> SEQ ID NO 2
<211> LENGTH: 18
<212> TYPE: PRT
<213> ORGANISM: Artificial Sequence
<220> FEATURE:
<223> OTHER INFORMATION: Adduct synthetically prepared
<220> FEATURE:
```

```
<221> NAME/KEY: MOD_RES
<222> LOCATION: (18)..(18)
<223> OTHER INFORMATION: GLUT4-K264-NHE-adduct: 4-NHE adduct linked to
      terminal lysine (corresponds to lysine 264 of GLUT4)

<400> SEQUENCE: 2

Leu Thr Gly Trp Ala Asp Val Ser Gly Val Leu Ala Glu Leu Lys Asp
1               5                   10                  15

Glu Lys
```